US010968451B2

(12) United States Patent
Wu et al.

(10) Patent No.: US 10,968,451 B2
(45) Date of Patent: Apr. 6, 2021

(54) MULTIPLEXED SHRNAS AND USES THEREOF

(71) Applicant: Texas Tech University System, Lubbock, TX (US)

(72) Inventors: Haoquan Wu, El Paso, TX (US); Jang-gi Choi, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 15/519,359

(22) PCT Filed: Oct. 14, 2015

(86) PCT No.: PCT/US2015/055537

§ 371 (c)(1),
(2) Date: Apr. 14, 2017

(87) PCT Pub. No.: WO2016/061232

PCT Pub. Date: Apr. 21, 2016

(65) Prior Publication Data

US 2017/0240899 A1 Aug. 24, 2017

Related U.S. Application Data

(60) Provisional application No. 62/240,709, filed on Oct. 13, 2015, provisional application No. 62/063,583, filed on Oct. 14, 2014.

(51) Int. Cl.
*C12N 15/113* (2010.01)
*A61K 48/00* (2006.01)

(52) U.S. Cl.
CPC ........ *C12N 15/1132* (2013.01); *A61K 48/005* (2013.01); *C12N 15/1138* (2013.01); *C12N 2310/14* (2013.01); *C12N 2310/141* (2013.01); *C12N 2310/31* (2013.01); *C12N 2310/3519* (2013.01); *C12N 2310/51* (2013.01); *C12N 2310/531* (2013.01); *C12N 2330/51* (2013.01); *C12N 2740/15042* (2013.01); *C12N 2750/14142* (2013.01)

(58) Field of Classification Search
None
See application file for complete search history.

(56) References Cited

U.S. PATENT DOCUMENTS

2006/0035344 A1* 2/2006 Pachuk .................. A61K 48/00 435/91.1
2006/0130176 A1* 6/2006 Reyes-Taboada ........................... C12N 15/8216 800/279
2010/0209440 A1* 8/2010 Shankar .................. A61P 31/12 424/178.1
2012/0208267 A1 8/2012 Friedman et al.
2013/0030042 A1* 1/2013 Couto ................ A61K 31/7088 514/44 R
2013/0179999 A1 7/2013 Hannon et al.

FOREIGN PATENT DOCUMENTS

WO WO-2010120969 A1 * 10/2010 ........... A61K 31/712
WO 2012159120 A2 11/2012
WO 2014117050 A2 7/2014

OTHER PUBLICATIONS

Zhang et al. (Virology Journal 2012, 9:118) (Year: 2012).*
Felekkis et al (Hippocratia 14(4): 236-240, 2010) (Year: 2010).*
Supplementary Material for Zhang et al. (Virology Journal 2012, 9:118) (Year: 2012).*
Choi, J.-G. et al., Multiplexing Seven miRNA-Based shRNAs to Suppress HIV Replication, Molecular Therapy (2015) 23(2):310-320.
Liu, Y. P. et al., Inhibition of HIV-1 by multiple siRNAs expressed from a single microRNA polycistron, Nucleic Acids Research (2008) 36(9):2811-2824.
McIntyre, G. J. et al., Multiple shRNA combinations for near-complete coverage of all HIV-1 strains, AIDS Research and Therapy (2011) 8, 15 pages.

* cited by examiner

*Primary Examiner* — Richard A Schnizer
(74) *Attorney, Agent, or Firm* — Loza & Loza LLP; Kevin L. Soules

(57) ABSTRACT

Nucleic acid molecules such as shRNA clusters and artificial miRNA clusters are disclosed, Also disclosed are methods of use, compositions, cells, viral particles, and kits relating to the nucleic acid molecules disclosed herein. The disclosure provides, at least in part nucleic acid molecules such as shRNA clusters encoding shRNA-like molecules and artificial miRNA clusters encoding modified pri-miRNA-like molecules. The shRNA clusters and artificial miRNA clusters disclosed herein can be used, for example, to produce artificial RNA molecules, e.g., RNAi molecules. Cells, viral particles, compositions (e.g., pharmaceutical compositions), kits, and methods relating to the nucleic acid molecules, e.g., shRNA clusters and artificial miRNA clusters, are also disclosed. The nucleic acid molecules (e.g., shRNA clusters and artificial miRNA clusters), artificial RNA molecules (e.g., RNAi molecules), cells, viral particles, compositions (e.g., pharmaceutical compositions), and kits and methods disclosed herein can be used to treat or prevent a disease, e.g., HIV infection and/or AIDS.

12 Claims, 27 Drawing Sheets

Specification includes a Sequence Listing.

| | Tat–shRNA target |
|---|---|
| HIV-1wt | CUAUGGCAGGAAGAAGCGGA |
| Mock | CUAUGGCAGGAAGAAGCGGA |
| Tat shRNA (Donor 2) | CUAUGGCAGGAAGAAGCAGA |
| Tat shRNA (Donor 4) | CUACGGCAGGAAGAAGCGGA |

FIG. 5C

Donor 1 (ART)

Donor 4 (Naive)

TABLE 1 Dominant small RNA reads in transfected cells

| Mature sequences | Vector alone | CCR5 shRNA | Gag shRNA | Env shRNA | Tat shRNA | Pol2 shRNA | Pol1 ShRNA | Vif shRNA | 2 shRNA | 4 shRNA | 7 shRNA |
|---|---|---|---|---|---|---|---|---|---|---|---|
| CCR5 | 0 | 141914 | 0 | 0 | 0 | 0 | 0 | 0 | 51630 | 27053 | 9891 |
| Gag | 0 | 0 | 19925 | 0 | 0 | 0 | 0 | 0 | 0 | 0 | 889 |
| Env | 0 | 0 | 0 | 38766 | 0 | 0 | 0 | 0 | 0 | 0 | 1979 |
| Tat | 0 | 0 | 0 | 0 | 100301 | 0 | 0 | 0 | 0 | 0 | 5351 |
| Pol2 | 0 | 0 | 0 | 0 | 0 | 45911 | 0 | 0 | 0 | 0 | 1991 |
| Pol2 | 0 | 0 | 0 | 0 | 0 | 0 | 33988 | 0 | 0 | 0 | 738 |
| Vif | 0 | 0 | 0 | 0 | 0 | 0 | 0 | 24859 | 13596 | 5757 | 1289 |
| Inner reference | 1627 | 2046 | 1556 | 1917 | 2235 | 2306 | 2589 | 1558 | 1594 | 1134 | 449 |

FIG. 13

TABLE 2. Oligonucleotide sequences used to insert target sites in the 3′ UTR of R-luc in psiCheck2 vector

| Oligonucleotides | 5′-3′ Sequence |
|---|---|
| psiCHECK-miR-30 | AGCTTCCAGTCGAGGATGTTTACAGCTACAGTACTGAGCTTCCAGTCGAGGATG |
| psiCHECK-miR-150 | TCGACTGGTACAACGGTTGGGAGAAGTCACGTGTACCACTGGTACAACGGTTGGGAGA |
| psiCHECK-Vif | AGTTCAGAAGTACACATCCCGCTACAGTACTAGTTCAGAAGTACACATCCC |
| psiCHECK-CCR5 | AACGAGCGCTCAGTTTACACCGCTACAGTACTGGCGAGCAAGCTCAGTTTACACCGC |
| psiCHECK-Gag | AGGGGAAGTGACATAGCAGGATGCTCAGAGGGGAAGTGACATAGCAGGC |
| psiCHECK-Env | ATGGCAGTCTAGCAGAAGAAATGCTCAGATGGCAGTCTAGCAGAAGAAGC |
| psiCHECK-Tat | CTATGGCAGGAAGAAGCGGAATGCTCAGCTATGGCAGGAAGAAGCGGAGC |
| psiCHECK-Pol1 | CCCTACAATCCCCAAAGTCAATGCTCAGCCCTACAATCCCCAAAGTCAGC |
| psiCHECK-Pol2 | AGATACAGGAGCAGATGATAATGCTCAGAGATACAGGAGCAGATGATAGC |

FIG. 14

TABLE 3. Sequences of the oligonucleotides used in the generation shRNAs

| Oligonucleotide | 5′-3′ Sequence |
|---|---|
| miR-30a 150nt | GACATTTTCTAGAATATTGCTGTTTGAATGAGGCTTCAGTACTTTACAGAATCGTTGCCTGCACATCTTG<br>GAAACACTTGCTGGGATTACTTCTTCAGGTTAACCCAACAGAAGGCTAAAGAAGGTATATTGCTGTTGA<br>CAGTGAGCGACTGTAACATCCTCGACTGGAAGCTGTGAAGCCACAGATGGGCTTTCAGTCGGATGTTT<br>GCAGCTGCCTACTGCCTCGGACTTCAAGGGGCTACTTTAGGAGCAATTATCTTGTTTACTAAAACTGAA<br>TACCTTGCTATCTCTTTGATACATTTTTA |
| miR-30a 30nt | GAAGGTATATTGCTGTTGACAGTGAGCGACTGTAAACATCCTCGACTGGAAGCTGTGAAGCCACAGAT<br>GGGCTTTCAGTCGGATGTTTGCAGCTGCCTACTGCCTCGGACTTCAAGGGGCTAC |
| miR-30a 20nt | TGCTGTTGACAGTGAGCGACTGTAAACATCCTGACTGGAATTGGCCACAGATGGGCTTTCAGTCGGATG<br>TTTGCAGCTGCCTACTGCCTCGGACTTC |
| miR-30a 15nt | TTGACAGTGAGCGACTGTAAACATCCTCGACTGGAAGCTGTGAAGCCACAGATGGGCTTTCAGTCGGA<br>TGTTTGCAGCTGCCTACTGCCTCGG |
| miR-150 60nt | CGGGGAGGCAGCGTCCCCGAGGCAGCAGCGGCAGCGGCGGCTCCTCTCCCCATGGCCCTGTCTCCCAA<br>CCCTTGTACCAGTGCTGGGCTCAGACCCTGGTACAGGCCTGGGGGACAGGGACCTGGGGACCCCGGCA<br>CCGGCAGGCCCCAAGGGGTGAGGTGAGCGGGCATTGGGAC |
| miR-150 30nt | GCAGCAGGCGGCTCCTCTCCCCATGGCCCTGTCTCCCAACCCTTGTACCAGTGCTGGGCTCAGACCCTG<br>GGTACAG GCCTGGGGGACAGGGACCTGGGGACCCCGGCACCGGCAGGCC |
| miR-150 20nt | CTCCTCTCCCCATGGCCCTGTCTCCCAACCCTTGTACCAGTGCTGGGCTCAGACCCTGGTACAGGCCTG<br>GGGGACAGGGACCTGGGGACCCCGGCA |
| miR-150 15nt | CTCCCCATGGCCCTGTCTCCCAACCCTTGTACCAGTGCTGGGCTCAGACCCTGGTACAGGCCTGGGGGA<br>CAGGGACCTGGGGACCC |

FIG. 15

SEQUENCE LISTING

<160> NUMBER OF SEQ ID NOS: 101

<210> SEQ ID NO 1
<211> LENGTH: 8035
<212> TYPE: DNA
<213> ORGANISM: Homo sapiens

<400> SEQUENCE: 1

```
ctgtttaaag acaaaaaggc cccaaaaagg agggatggca cgaaacaccc tccaatatgg     60
gcatggagtc tagagtgaca aagtgatcaa aagttcattt cctatggggt gtccgaatgt    120
acttaataat aaaaagagaa caagagccat gcaaactgag agggacaaag tagaaagagt    180
agcagacacc aagcaactaa gtcacagcat gataagctgc tagcttgttg tcattattgt    240
atccagaaca acatttcatt taaatgctga agaatttccc atgggtcccc actttcttgt    300
gaatccttgg gctgaacccc cccgtcctga gtggttacta gaacacacct ctggaccaga    360
aacacaagag tggagtaaca cacactgcaa agctgtgctt ccttgtttca gcctgtgaat    420
cctcaccttg tttcccatct agcctatatt tttcaaacta acttggccat agaatcatgt    480
cgtatttagg gtggaagctg ccccaggtct agcgcgtcat ttaacagatg aggaaatgga    540
agcttgggca gtggaagtat cttgccgagg tcacacagca agtcagcagc acagcgtgtg    600
tgactccgag cctgctccgc tagcccacat tgccctctgg gggtgagtat gtcttcacat    660
cctccaatac ccctaatgac agacaaacag aacatggcaa agcctcagct ctgcatggtg    720
aaagtaagaa ccagcaattg ccacaaacag aaatacagtg ttggtccggc agcctccggg    780
ggttctgcac aagtggatta ccagtgaata caaggctatc tatcttccga aaaaccaaag    840
ttgtatttat gctatctatt ttctataaaa ttttatatta atttacttgt cctatttttg    900
aactctttca aaagcacact ttatatttcc cctgcttaaa cagtcccccg agggtgggtg    960
cccaaaaggc tctacacttg ttatcattcc ctctccacca caggcatatt gagtaagttt   1020
gtatttgggt ttttttaaaa cctccactct acagttaaga aaactaaggc acagagcttc   1080
aataatttgg tcagagccaa gtagcagtaa tgaagctgga ggttaaaccc agcagcatga   1140
ctgcagttct taatcaatgc cttttgaatt gcacatatgg gatgaactag aacattttct   1200
cgatgattcg ctgtccttgt tatgattatg ttactgagct ctgttgtagc acagacatat   1260
gtccctatat ggggcggggg tgggggtgtc ttgatcgctg ggctatttct atactgttct   1320
ggcttttccc aagcagtcat ttctttctat cctccaagca ccagcaatta gctttacctt   1380
ttcagcttct agtttgctga aactaatctg ctatagacag agactccggt gaaccaattt   1440
tattaggatt tgatcaaata aactctctct gacaaaggac tgctgaaaga gtaactaaga   1500
gtttgatgtt tactgagtgc atagtatgtg ctagatgctg gccgtggatg cctcatagaa   1560
tcctcccaac aactcatgaa atgactactg tcattcagcc caatacccag acgagaaagc   1620
tgagggtaag acaggtttca agcttggcag tctgactaca gaggccactg gcttagcccc   1680
tgggttagtc tgcctctgta ggattggggg cacgtaattt tgctgtttgg ggtctcattt   1740
gccttcttag agatcacaag ccaaagcttt ttattctaga gccaaggtca cggaagccca   1800
gaggacatct tgtggctcgg gagtagctct ctgctgtctt ctcagctctg ctgacaatac   1860
ttgagatttt cagatgtcac caaccgccaa gagagcttga tatgactgta tatagtatag   1920
tcataaagaa cctgaacttg accatatact tatgtcatgt ggaaaatttc tcatagcttc   1980
agatagatta tatctggagt gaaggatcct gccacctacg tatctggcat agtgtgagtc   2040
ctcataaatg cttactggtt tgaagggcaa caaaatagtg aacagagtga aaatccccac   2100
```

-continued taagatcctg ggtccagaaa aagatgggaa acctgtttag ctcacccgtg agcccatagt 2160
taaaactctt tagacaacag gttgtttccg tttacagaga acaataatat tgggtggtga 2220
gcatctgtgt gggggttggg gtgggatagg ggatacgggg agagtggaga aaaaggggac 2280
acagggttaa tgtgaagtcc aggatccccc tctacattta aagttggttt aagttggctt 2340
taattaatag caactcttaa gataatcaga attttcttaa ccttttagcc ttactgttga 2400
aaagccctgt gatcttgtac aaatcatttg cttcttggat agtaatttct tttactaaaa 2460
tgtgggcttt tgactagatg aatgtaaatg ttcttctagc tctgatatcc tttattcttt 2520
atattttcta acagattctg tgtagtggga tgagcagaga acaaaaacaa aataatccag 2580
tgagaaaagc ccgtaaataa accttcagac cagagatcta ttctccagct tattttaagc 2640
tcaacttaaa aagaagaact gttctctgat tcttttcgcc ttcaatacac ttaatgattt 2700
aactccaccc tccttcaaaa gaaacagcat ttcctacttt tatactgtct atatgattga 2760
tttgcacagc tcatctggcc agaagagctg agacatccgt tcccctacaa gaaactctcc 2820
ccggtaagta acctctcagc tgcttggcct gttagttagc ttctgagatg agtaaaagac 2880
tttacaggaa acccatagaa gacatttggc aaacaccaag tgctcataca attatcttaa 2940
aatataatct ttaagataag gaaagggtca cagtttggaa tgagtttcag acggttataa 3000
catcaaagat acaaaacatg attgtgagtg aaagacttta aagggagcaa tagtatttta 3060
ataactaaca atccttacct ctcaaaagaa agatttgcag agagatgagt cttagctgaa 3120
atcttgaaat cttatcttct gctaaggaga actaaaccct ctccagtgag atgccttctg 3180
aatatgtgcc cacaagaagt tgtgtctaag tctggttctc tttttctttt ttcctccaga 3240
caagagggaa gcctaaaaat ggtcaaaatt aatattaaat tacaaacgcc aaataaaatt 3300
ttcctctaat atatcagttt catggcacag ttagtatata attctttatg gttcaaaatt 3360
aaaaatgagc ttttctaggg gcttctctca gctgcctagt ctaaggtgca gggagtttga 3420
gactcacagg gtttaataag agaaaattct cagctagagc agctgaactt aaatagacta 3480
ggcaagacag ctggttataa gactaaacta cccagaatgc atgacattca tctgtggtgg 3540
cagacgaaac attttttatt atattatttc ttgggtatgt atgacaactc ttaattgtgg 3600
caactcagaa actacaaaca caaacttcac agaaaatgtg aggattttac aattggctgt 3660
tgtcatctat gaccttctct gggacttggg cacccggcca tttcactctg actacatcat 3720
gtcaccaaac atctgatggt cttgcctttt aattctcttt tcgaggactg agagggaggg 3780
tagcatggta gttaagagtg caggcttccc gcattcaaaa tcggttgctt actagctgtg 3840
tggctttgag caagttactc accctctctg tgcttcaagg tccttgtctg caaaatgtga 3900
aaaatatttc ctgcctcata aggttgccct aaggattaaa tgaatgaatg ggtatgatgc 3960
ttagaacagt gattggcatc cagtatgtgc cctcgaggcc tcttaattat tactggcttg 4020
ctcatagtgc atgttctttg tgggctaact ctagcgtcaa taaaaatgtt aagactgagt 4080
tgcagccggg catggtggct catgcctgta atcccagcat tctaggaggc tgaggcagga 4140
ggatcgcttg agcccaggag ttcgagacca gcctgggcaa catagtgtga tcttgtatct 4200
ataaaaataa acaaaattag cttggtgtgg tggcgcctgt agtccccagc cacttggagg 4260
ggtgaggtga gaggattgct tgagcccggg atggtccagg ctgcagtgag ccatgatcgt 4320
gccactgcac tccagcctgg gcgacagagt gagaccctgt ctcacaacaa caacaacaac 4380
aacaaaaagg ctgagctgca ccatgcttga cccagtttct taaaattgtt gtcaaagctt 4440

-continued

```
cattcactcc atggtgctat agagcacaag attttatttg gtgagatggt gctttcatga   4500
attcccccaa cagagccaag ctctccatct agtggacagg gaagctagca gcaaaccttc   4560
ccttcactac aaaacttcat tgcttggcca aaaagagagt taattcaatg tagacatcta   4620
tgtaggcaat taaaaaccta ttgatgtata aaacagtttg cattcatgga gggcaactaa   4680
atacattcta ggactttata aaagatcact ttttatttat gcacagggtg gaacaagatg   4740
gattatcaag tgtcaagtcc aatctatgac atcaattatt atacatcgga gccctgccaa   4800
aaaatcaatg tgaagcaaat cgcagcccgc ctcctgcctc cgctctactc actggtgttc   4860
atctttggtt ttgtgggcaa catgctggtc atcctcatcc tgataaactg caaaaggctg   4920
aagagcatga ctgacatcta cctgctcaac ctggccatct ctgacctgtt tttccttctt   4980
actgtcccct tctgggctca ctatgctgcc gcccagtggg actttggaaa tacaatgtgt   5040
caactcttga cagggctcta ttttataggc ttcttctctg gaatcttctt catcatcctc   5100
ctgacaatcg ataggtacct ggctgtcgtc catgctgtgt ttgctttaaa agccaggacg   5160
gtcacctttg gggtggtgac aagtgtgatc acttgggtgg tggctgtgtt tgcgtctctc   5220
ccaggaatca tctttaccag atctcaaaaa gaaggtcttc attacacctg cagctctcat   5280
tttccataca gtcagtatca attctggaag aatttccaga cattaaagat agtcatcttg   5340
gggctggtcc tgccgctgct tgtcatggtc atctgctact cgggaatcct aaaaactctg   5400
cttcggtgtc gaaatgagaa gaagaggcac agggctgtga ggcttatctt caccatcatg   5460
attgtttatt ttctcttctg ggctccctac aacattgtcc ttctcctgaa caccttccag   5520
gaattctttg gcctgaataa ttgcagtagc tctaacaggt tggaccaagc tatgcaggtg   5580
acagagactc ttgggatgac gcactgctgc atcaacccca tcatctatgc ctttgtcggg   5640
gagaagttca gaaactacct cttagtcttc ttccaaaagc acattgccaa acgcttctgc   5700
aaatgctgtt ctattttcca gcaagaggct cccgagcgag caagctcagt ttacacccga   5760
tccactgggg agcaggaaat atctgtgggc ttgtgacacg gactcaagtg ggctggtgac   5820
ccagtcagag ttgtgcacat ggcttagttt tcatacacag cctgggctgg gggtggggtg   5880
ggagaggtct tttttaaaag gaagttactg ttatagaggg tctaagattc atccatttat   5940
ttggcatctg tttaaagtag attagatctt ttaagcccat caattataga aagccaaatc   6000
aaaatatgtt gatgaaaaat agcaaccttt ttatctcccc ttcacatgca tcaagttatt   6060
gacaaactct cccttcactc cgaaagttcc ttatgtatat ttaaaagaaa gcctcagaga   6120
attgctgatt cttgagttta gtgatctgaa cagaaatacc aaaattattt cagaaatgta   6180
caacttttta cctagtacaa ggcaacatat aggttgtaaa tgtgtttaaa acaggtcttt   6240
gtcttgctat ggggagaaaa gacatgaata tgattagtaa agaaatgaca cttttcatgt   6300
gtgatttccc ctccaaggta tggttaataa gtttcactga cttagaacca ggcgagagac   6360
ttgtggcctg ggagagctgg ggaagcttct taaatgagaa ggaatttgag ttggatcatc   6420
tattgctggc aaagacagaa gcctcactgc aagcactgca tgggcaagct tggctgtaga   6480
aggagacaga gctggttggg aagacatggg gaggaaggac aaggctagat catgaagaac   6540
cttgacggca ttgctccgtc taagtcatga gctgagcagg gagatcctgg ttggtgttgc   6600
agaaggttta ctctgtggcc aaaggagggt caggaaggat gagcatttag ggcaaggaga   6660
ccaccaacag ccctcaggtc agggtgagga tggcctctgc taagctcaag gcgtgaggat   6720
gggaaggagg gaggtattcg taaggatggg aaggagggag gtattcgtgc agcatatgag   6780
gatgcagagt cagcagaact ggggtggatt tggtttggaa gtgagggtca gagaggagtc   6840
```

```
agagagaatc cctagtcttc aagcagattg gagaaaccct tgaaaagaca tcaagcacag   6900
aaggaggagg aggaggttta ggtcaagaag aagatggatt ggtgtaaaag gatgggtctg   6960
gtttgcagag cttgaacaca gtctcaccca gactccaggc tgtctttcac tgaatgcttc   7020
tgacttcata gatttccttc ccatcccagc tgaaatactg aggggtctcc aggaggagac   7080
tagatttatg aatacacgag gtatgaggtc taggaacata cttcagctca cacatgagat   7140
ctaggtgagg attgattacc tagtagtcat ttcatgggtt gttgggagga ttctatgagg   7200
caaccacagg cagcatttag cacatactac acattcaata agcatcaaac tcttagttac   7260
tcattcaggg atagcactga gcaaagcatt gagcaaaggg gtcccatata ggtgagggaa   7320
gcctgaaaaa ctaagatgct gcctgcccag tgcacacaag tgtaggtatc attttctgca   7380
tttaaccgtc aataggcaaa ggggggaagg gacatattca tttggaaata agctgccttg   7440
agccttaaaa cccacaaaag tacaatttac cagcctccgt atttcagact gaatgggggt   7500
ggggggggcg ccttaggtac ttattccaga tgccttctcc agacaaacca gaagcaacag   7560
aaaaaatcgt ctctccctcc ctttgaaatg aatatacccc ttagtgtttg ggtatattca   7620
tttcaaaggg agagagagag gtttttttct gttctttctc atatgattgt gcacatactt   7680
gagactgttt tgaatttggg ggatggctaa aaccatcata gtacaggtaa ggtgagggaa   7740
tagtaagtgg tgagaactac tcagggaatg aaggtgtcag aataataaga ggtgctactg   7800
actttctcag cctctgaata tgaacggtga gcattgtggc tgtcagcagg aagcaacgaa   7860
gggaaatgtc tttccttttg ctcttaagtt gtggagagtg caacagtagc ataggaccct   7920
accctctggg ccaagtcaaa gacattctga catcttagta tttgcatatt cttatgtatg   7980
tgaaagttac aaattgcttg aaagaaaata tgcatctaat aaaaaacacc ttcta        8035
```

<210> SEQ ID NO 2
<211> LENGTH: 1503
<212> TYPE: DNA
<213> ORGANISM: Human immunodeficiency virus type 1

<400> SEQUENCE: 2

```
atgggtgcga gagcgtcagt attaagcggg ggaaaattag atcgatggga aaaaattcgg     60
ttaaggccag ggggaaagaa aaaatataaa ttaaaacata tagtatgggc aagcagggag    120
ctagaacgat tcgcagttaa tcctggcctg ttagaaacat cagaaggctg tagacaaata    180
ctgggacagc tacaaccatc ccttcagaca ggatcagaag aacgtagatc attatataat    240
acagtagcaa ccctctattg tgtgcatcaa aggatagaga taaaagacac caaggaagct    300
ttagacaaga tagaggaaga gcaaaacaaa agtaagaaaa aagcacagca agcagcagct    360
gacacaggac acagcagcca ggtcagccaa aattacccta tagtgcagaa catccagggg    420
caaatggtac atcaggccat atcacctaga actttaaatg catgggtaaa agtagtagaa    480
gagaaggctt tcagcccaga agtgataccc atgttttcag cattatcaga aggagccacc    540
ccacaagatt taaacaccat gctaaacaca gtggggggac atcaagcagc catgcaaatg    600
ttaaaagaga ccatcaatga ggaagctgca gaatgggata gagtgcatcc agtgcatgca    660
gggcctattg caccaggcca gatgagagaa ccaaggggaa gtgacatagc aggaactact    720
agtacccttc aggaacaaat aggatggatg acacataatc cacctatccc agtaggagaa    780
atctataaaa gatggataat cctgggatta aataaaatag taagaatgta tagccctacc    840
agcattctgg acataagaca aggaccaaag gaacccttta gagactatgt agaccgattc    900
```

tataaaactc taagagccga gcaagcttca caagaggtaa aaaattggat gacagaaacc 960
ttgttggtcc aaaatgcgaa cccagattgt aagactattt taaaagcatt gggaccagga 1020
gcgacactag aagaaatgat gacagcatgt cagggagtgg ggggacccgg ccataaagca 1080
agagttttgg ctgaagcaat gagccaagta acaaatccag ctaccataat gatacagaaa 1140
ggcaatttta ggaaccaaag aaagactgtt aagtgtttca attgtggcaa agaagggcac 1200
atagccaaaa attgcagggc ccctaggaaa aagggctgtt ggaaatgtgg aaaggaagga 1260
caccaaatga aagattgtac tgagagacag gctaattttt tagggaagat ctggccttcc 1320
cacaagggaa ggccagggaa ttttcttcag agcagaccag agccaacagc cccaccagaa 1380
gagagcttca ggtttgggga agagacaaca actccctctc agaagcagga gccgatagac 1440
aaggaactgt atcctttagc ttccctcaga tcactctttg gcagcgaccc ctcgtcacaa 1500
taa 1503

<210> SEQ ID NO 3
<211> LENGTH: 3012
<212> TYPE: DNA
<213> ORGANISM: Human immunodeficiency virus type 1

<400> SEQUENCE: 3 tttttaggg aagatctggc cttcccacaa gggaaggcca gggaattttc ttcagagcag 60
accagagcca acagccccac cagaagagag cttcaggttt ggggaagaga caacaactcc 120
ctctcagaag caggagccga tagacaagga actgtatcct ttagcttccc tcagatcact 180
ctttggcagc gacccctcgt cacaataaag ataggggggc aattaaagga agctctatta 240
gatacaggag cagatgatac agtattagaa gaaatgaatt tgccaggaag atggaaacca 300
aaaatgatag ggggaattgg aggttttatc aaagtaagac agtatgatca gatactcata 360
gaaatctgcg gacataaagc tataggtaca gtattagtag gacctacacc tgtcaacata 420
attggaagaa atctgttgac tcagattggc tgcactttaa attttcccat tagtcctatt 480
gagactgtac cagtaaaatt aaagccagga atggatggcc caaaagttaa acaatggcca 540
ttgacagaag aaaaaataaa agcattagta gaaatttgta cagaaatgga aaaggaagga 600
aaaatttcaa aaattgggcc tgaaaatcca tacaatactc cagtatttgc cataaagaaa 660
aaagacagta ctaaatggag aaaattagta gatttcagag aacttaataa gagaactcaa 720
gatttctggg aagttcaatt aggaatacca catcctgcag ggttaaaaca gaaaaaatca 780
gtaacagtac tggatgtggg cgatgcatat ttttcagttc ccttagataa agacttcagg 840
aagtatactg catttaccat acctagtata aacaatgaga caccagggat tagatatcag 900
tacaatgtgc ttccacaggg atggaaagga tcaccagcaa tattccagtg tagcatgaca 960
aaaatcttag agccttttag aaaacaaaat ccagacatag tcatctatca atacatggat 1020
gatttgtatg taggatctga cttagaaata gggcagcata gaacaaaaat agaggaactg 1080
agacaacatc tgttgaggtg gggatttacc acaccagaca aaaaacatca gaaagaacct 1140
ccattccttt ggatgggtta tgaactccat cctgataaat ggacagtaca gcctatagtg 1200
ctgccagaaa aggacagctg gactgtcaat gacatacaga aattagtggg aaaattgaat 1260
tgggcaagtc agatttatgc agggattaaa gtaaggcaat tatgtaaact tcttagggga 1320
accaaagcac taacagaagt agtaccacta acagaagaag cagagctaga actggcagaa 1380
aacagggaga ttctaaaaga accggtacat ggagtgtatt atgacccatc aaaagactta 1440
atagcagaaa tacagaagca ggggcaaggc caatggacat atcaaattta tcaagagcca 1500

```
tttaaaaatc tgaaaacagg aaagtatgca agaatgaagg gtgcccacac taatgatgtg   1560
aaacaattaa cagaggcagt acaaaaaata gccacagaaa gcatagtaat atggggaaag   1620
actcctaaat ttaaattacc catacaaaag gaaacatggg aagcatggtg gacagagtat   1680
tggcaagcca cctggattcc tgagtgggag tttgtcaata cccctccctt agtgaagtta   1740
tggtaccagt tagagaaaga acccataata ggagcagaaa ctttctatgt agatggggca   1800
gccaataggg aaactaaatt aggaaaagca ggatatgtaa ctgacagagg aagacaaaaa   1860
gttgtccccc taacggacac aacaaatcag aagactgagt tacaagcaat tcatctagct   1920
ttgcaggatt cgggattaga agtaaacata gtgacagact cacaatatgc attgggaatc   1980
attcaagcac aaccagataa gagtgaatca gagttagtca gtcaaataat agagcagtta   2040
ataaaaaagg aaaaagtcta cctggcatgg gtaccagcac acaaaggaat tggaggaaat   2100
gaacaagtag ataaattggt cagtgctgga atcaggaaag tactattttt agatggaata   2160
gataaggccc aagaagaaca tgagaaatat cacagtaatt ggagagcaat ggctagtgat   2220
tttaacctac cacctgtagt agcaaaagaa atagtagcca gctgtgataa atgtcagcta   2280
aaaggggaag ccatgcatgg acaagtagac tgtagcccag gaatatggca gctagattgt   2340
acacatttag aaggaaaagt tatcttggta gcagttcatg tagccagtgg atatatagaa   2400
gcagaagtaa ttccagcaga gacagggcaa gaaacagcat acttcctctt aaaattagca   2460
ggaagatggc cagtaaaaac agtacataca gacaatggca gcaatttcac cagtactaca   2520
gttaaggccg cctgttggtg ggcggggatc aagcaggaat ttggcattcc ctacaatccc   2580
caaagtcaag gagtaataga atctatgaat aaagaattaa agaaaattat aggacaggta   2640
agagatcagg ctgaacatct taagacagca gtacaaatgg cagtattcat ccacaatttt   2700
aaaagaaaag gggggattgg ggggtacagt gcaggggaaa gaatagtaga cataatagca   2760
acagacatac aaactaaaga attacaaaaa caaattacaa aaattcaaaa ttttcgggtt   2820
tattacaggg acagcagaga tccagtttgg aaaggaccag caaagctcct ctggaaaggt   2880
gaaggggcag tagtaataca agataatagt gacataaaag tagtgccaag aagaaaagca   2940
aagatcatca gggattatgg aaaacagatg gcaggtgatg attgtgtggc aagtagacag   3000
gatgaggatt aa                                                       3012
```

<210> SEQ ID NO 4
<211> LENGTH: 261
<212> TYPE: DNA
<213> ORGANISM: Human immunodeficiency virus type 1

<400> SEQUENCE: 4

```
atggagccag tagatcctag actagagccc tggaagcatc caggaagtca gcctaaaact     60
gcttgtacca attgctattg taaaaagtgt tgctttcatt gccaagtttg tttcataaca    120
aaagccttag gcatctccta tggcaggaag aagcggagac agcgacgaag acctcctcaa    180
ggcagtcaga ctcatcaagt ttctctatca aagcaaccca cctcccaatc ccgaggggac    240
ccgacaggcc cgaaggaata g                                              261
```

<210> SEQ ID NO 5
<211> LENGTH: 579
<212> TYPE: DNA
<213> ORGANISM: Human immunodeficiency virus type 1

<400> SEQUENCE: 5

```
atggaaaaca gatggcaggt gatgattgtg tggcaagtag acaggatgag gattaacaca      60

tggaaaagat tagtaaaaca ccatatgtat atttcaagga aagctaagga ctggttttat     120

agacatcact atgaaagtac taatccaaaa ataagttcag aagtacacat cccactaggg     180

gatgctaaat tagtaataac aacatattgg ggtctgcata caggagaaag agactggcat     240

ttgggtcagg gagtctccat agaatggagg aaaaagagat atagcacaca agtagaccct     300

gacctagcag accaactaat tcatctgcac tattttgatt gtttttcaga atctgctata     360

agaaatacca tattaggacg tatagttagt cctaggtgtg aatatcaagc aggacataac     420

aaggtaggat ctctacagta cttggcacta gcagcattaa taaaaccaaa acagataaag     480

ccacctttgc ctagtgttag gaaactgaca gaggacagat ggaacaagcc ccagaagacc     540

aagggccaca gagggagcca tacaatgaat ggacactag                            579


<210> SEQ ID NO 6
<211> LENGTH: 2571
<212> TYPE: DNA
<213> ORGANISM: Human immunodeficiency virus type 1

<400> SEQUENCE: 6

atgagagtga aggagaaata tcagcacttg tggagatggg ggtggagatg gggcaccatg      60

ctccttggga tgttgatgat ctgtagtgct acagaaaaat tgtgggtcac agtctattat     120

ggggtacctg tgtggaagga agcaaccacc actctatttt gtgcatcaga tgctaaagca     180

tatgatacag aggtacataa tgtttgggcc acacatgcct gtgtacccac agaccccaac     240

ccacaagaag tagtattggt aaatgtgaca gaaaatttta acatgtggaa aaatgacatg     300

gtagaacaga tgcatgagga tataatcagt ttatgggatc aaagcctaaa gccatgtgta     360

aaattaaccc cactctgtgt tagtttaaag tgcactgatt tgaagaatga tactaatacc     420

aatagtagta gcgggagaat gataatggag aaaggagaga taaaaaactg ctctttcaat     480

atcagcacaa gcataagagg taaggtgcag aaagaatatg catttttta taaacttgat      540

ataataccaa tagataatga tactaccagc tatacgttga caagttgtaa cacctcagtc     600

attacacagg cctgtccaaa ggtatccttt gagccaattc ccatacatta ttgtgccccg     660

gctggttttg cgattctaaa atgtaataat aagacgttca atggaacagg accatgtaca     720

aatgtcagca cagtacaatg tacacatgga attaggccag tagtatcaac tcaactgctg     780

ttaaatggca gtctagcaga agaagaggta gtaattagat ctgtcaattt cacggacaat     840

gctaaaacca taatagtaca gctgaacaca tctgtagaaa ttaattgtac aagacccaac     900

aacaatacaa gaaaaaaaat ccgtatccag aggggaccag ggagagcatt tgttacaata     960

ggaaaaatag gaaatatgag acaagcacat tgtaacatta gtagagcaaa atggaatgcc    1020

actttaaaac agatagctag caaattaaga gaacaatttg gaaataataa aacaataatc    1080

tttaagcaat cctcaggagg ggacccagaa attgtaacgc acagttttaa ttgtggaggg    1140

gaatttttct actgtaattc aacacaactg tttaatagta cttggtttaa tagtacttgg    1200

agtactgaag ggtcaaataa cactgaagga agtgacacaa tcacactccc atgcagaata    1260

aaacaattta taaacatgtg gcaggaagta ggaaaagcaa tgtatgcccc tcccatcagc    1320

ggacaaatta gatgttcatc aaatattaca gggctgctat taacaagaga tggtggtaat    1380

aacaacaatg ggtccgagat cttcagacct ggaggaggag atatgaggga caattggaga    1440

agtgaattat ataaatataa agtagtaaaa attgaaccat taggagtagc acccaccaag    1500

gcaaagagaa gagtggtgca gagagaaaaa agagcagtgg gaataggagc tttgttcctt    1560
```

gggttcttgg gagcagcagg aagcactatg ggcgcagcgt caatgacgct gacggtacag 1620
gccagacaat tattgtctgg tatagtgcag cagcagaaca atttgctgag ggctattgag 1680
gcgcaacagc atctgttgca actcacagtc tggggcatca agcagctcca ggcaagaatc 1740
ctggctgtgg aaagatacct aaaggatcaa cagctcctgg ggatttgggg ttgctctgga 1800
aaactcattt gcaccactgc tgtgccttgg aatgctagtt ggagtaataa atctctggaa 1860
cagatttgga atcacacgac ctggatggag tgggacagag aaattaacaa ttacacaagc 1920
ttaatacact ccttaattga agaatcgcaa aaccagcaag aaaagaatga acaagaatta 1980
ttggaattag ataaatgggc aagtttgtgg aattggttta acataacaaa ttggctgtgg 2040
tatataaaat tattcataat gatagtagga ggcttggtag gtttaagaat agtttttgct 2100
gtactttctg tagtgaatag agttaggcag ggatattcac cattatcgtt tcagacccac 2160
ctcccaatcc cgaggggacc cgacaggccc gaaggaatag aagaagaagg tggagagaga 2220
gacagagaca gatccattcg attagtgaac ggatccttag cacttatctg ggacgatctg 2280
cggagcctgt gcctcttcag ctaccaccgc ttgagagact tactcttgat tgtaacgagg 2340
attgtggaac ttctgggacg cagggggtgg gaagccctca aatattggtg gaatctccta 2400
caatattgga gtcaggagct aaagaatagt gctgttagct tgctcaatgc cacagctata 2460
gcagtagctg aggggacaga tagggttata gaagtagtac aagaagctta tagagctatt 2520
cgccacatac ctagaagaat aggacagggc ttggaaagga ttttgctata a 2571

<210> SEQ ID NO 7
<211> LENGTH: 9263
<212> TYPE: DNA
<213> ORGANISM: Human immunodeficiency virus type 1

<400> SEQUENCE: 7
ggtctctctg gttagaccag atctgagcct gggagctctc tggctaacta gggaacccac 60
tgcttaagcc tcaataaagc ttgccttgag tgcttcaagt agtgtgtgcc cgtctgttgt 120
gtgactctgg taactagaga tccctcagac ccttttagtc agtgtggaaa atctctagca 180
gtggcgcccg aacagggaca tgaaagcgaa agggaaacca gaggagctct ctcgacgcag 240
gactcggctt gctgaagcgc gcacggcaag aggcgagggg cggcgactgg tgagtacgcc 300
aaaaattttg actagcggag gctagaagga gagagatggg tgcgagagcg tcagtattaa 360
gcgggggaaa attagatcga tgggaaaaaa ttcggttaag gccaggggga aagaaaaaat 420
ataaattaaa acatatagta tgggcaagca gggagctaga acgattcgca gttaatcctg 480
gcctgttaga aacatcagaa ggctgtagac aaatactggg acagctacaa ccatcccttc 540
agacaggatc agaagaacgt agatcattat ataatacagt agcaaccctc tattgtgtgc 600
atcaaaggat agagataaaa gacaccaagg aagctttaga caagatagag gaagagcaaa 660
acaaaagtaa gaaaaaagca cagcaagcag cagctgacac aggacacagc agccaggtca 720
gccaaaatta ccctatagtg cagaacatcc aggggcaaat ggtacatcag gccatatcac 780
ctagaacttt aaatgcatgg gtaaaagtag tagaagagaa ggctttcagc ccagaagtga 840
tacccatgtt ttcagcatta tcagaaggag ccaccccaca agatttaaac accatgctaa 900
acacagtggg gggacatcaa gcagccatgc aaatgttaaa agagaccatc aatgaggaag 960
ctgcagaatg ggatagagtg catccagtgc atgcagggcc tattgcacca ggccagatga 1020
gagaaccaag ggaagtgac atagcaggaa ctactagtac ccttcaggaa caaataggat 1080

-continued

```
ggatgacaca taatccacct atcccagtag gagaaatcta taaaagatgg ataatcctgg   1140
gattaaataa aatagtaaga atgtatagcc ctaccagcat tctggacata agacaaggac   1200
caaaggaacc ctttagagac tatgtagacc gattctataa aactctaaga gccgagcaag   1260
cttcacaaga ggtaaaaaat tggatgacag aaaccttgtt ggtccaaaat gcgaacccag   1320
attgtaagac tattttaaaa gcattgggac caggagcgac actagaagaa atgatgacag   1380
catgtcaggg agtgggggga cccggccata aagcaagagt tttggctgaa gcaatgagcc   1440
aagtaacaaa tccagctacc ataatgatac agaaaggcaa ttttaggaac caaagaaaga   1500
ctgttaagtg tttcaattgt ggcaaagaag ggcacatagc caaaaattgc agggccccta   1560
ggaaaaaggg ctgttggaaa tgtggaaagg aaggacacca aatgaaagat tgtactgaga   1620
gacaggctaa tttttaggg aagatctggc cttcccacaa gggaaggcca gggaattttc   1680
ttcagagcag accagagcca acagccccac cagaagagag cttcaggttt ggggaagaga   1740
caacaactcc ctctcagaag caggagccga tagacaagga actgtatcct ttagcttccc   1800
tcagatcact ctttggcagc gacccctcgt cacaataaag ataggggggc aattaaagga   1860
agctctatta gatacaggag cagatgatac agtattagaa gaaatgaatt tgccaggaag   1920
atggaaacca aaaatgatag ggggaattgg aggttttatc aaagtaagac agtatgatca   1980
gatactcata gaaatctgcg gacataaagc tataggtaca gtattagtag gacctacacc   2040
tgtcaacata attggaagaa atctgttgac tcagattggc tgcactttaa attttcccat   2100
tagtcctatt gagactgtac cagtaaaatt aaagccagga atggatggcc caaaagttaa   2160
acaatggcca ttgacagaag aaaaaataaa agcattagta gaaatttgta cagaaatgga   2220
aaaggaagga aaaatttcaa aaattgggcc tgaaaatcca tacaatactc cagtatttgc   2280
cataaagaaa aaagacagta ctaaatggag aaaattagta gatttcagag aacttaataa   2340
gagaactcaa gatttctggg aagttcaatt aggaatacca catcctgcag ggttaaaaca   2400
gaaaaaatca gtaacagtac tggatgtggg cgatgcatat ttttcagttc ccttagataa   2460
agacttcagg aagtatactg catttaccat acctagtata aacaatgaga caccagggat   2520
tagatatcag tacaatgtgc ttccacaggg atggaaagga tcaccagcaa tattccagtg   2580
tagcatgaca aaaatcttag agccttttag aaaacaaaat ccagacatag tcatctatca   2640
atacatggat gatttgtatg taggatctga cttagaaata gggcagcata gaacaaaaat   2700
agaggaactg agacaacatc tgttgaggtg gggatttacc acaccagaca aaaaacatca   2760
gaaagaacct ccattccttt ggatgggtta tgaactccat cctgataaat ggacagtaca   2820
gcctatagtg ctgccagaaa aggacagctg gactgtcaat gacatacaga aattagtggg   2880
aaaattgaat tgggcaagtc agatttatgc agggattaaa gtaaggcaat tatgtaaact   2940
tcttagggga accaaagcac taacagaagt agtaccacta acagaagaag cagagctaga   3000
actggcagaa aacagggaga ttctaaaaga accggtacat ggagtgtatt atgacccatc   3060
aaaagactta atagcagaaa tacagaagca ggggcaaggc caatggacat atcaaattta   3120
tcaagagcca tttaaaaatc tgaaaacagg aaagtatgca agaatgaagg gtgcccacac   3180
taatgatgtg aaacaattaa cagaggcagt acaaaaaata gccacagaaa gcatagtaat   3240
atggggaaag actcctaaat ttaaattacc catacaaaag gaaacatggg aagcatggtg   3300
gacagagtat tggcaagcca cctggattcc tgagtgggag tttgtcaata cccctccctt   3360
agtgaagtta tggtaccagt tagagaaaga acccataata ggagcagaaa ctttctatgt   3420
agatggggca gccaataggg aaactaaatt aggaaaagca ggatatgtaa ctgacagagg   3480
```

-continued

```
aagacaaaaa gttgtccccc taacggacac aacaaatcag aagactgagt tacaagcaat   3540
tcatctagct ttgcaggatt cgggattaga agtaaacata gtgacagact cacaatatgc   3600
attgggaatc attcaagcac aaccagataa gagtgaatca gagttagtca gtcaaataat   3660
agagcagtta ataaaaaagg aaaaagtcta cctggcatgg gtaccagcac acaaaggaat   3720
tggaggaaat gaacaagtag ataaattggt cagtgctgga atcaggaaag tactattttt   3780
agatggaata gataaggccc aagaagaaca tgagaaatat cacagtaatt ggagagcaat   3840
ggctagtgat tttaacctac cacctgtagt agcaaaagaa atagtagcca gctgtgataa   3900
atgtcagcta aaggggaag ccatgcatgg acaagtagac tgtagcccag gaatatggca   3960
gctagattgt acacatttag aaggaaaagt tatcttggta gcagttcatg tagccagtgg   4020
atatatagaa gcagaagtaa ttccagcaga gacagggcaa gaaacagcat acttcctctt   4080
aaaattagca ggaagatggc cagtaaaaac agtacataca gacaatggca gcaatttcac   4140
cagtactaca gttaaggccg cctgttggtg ggcggggatc aagcaggaat ttggcattcc   4200
ctacaatccc caaagtcaag gagtaataga atctatgaat aaagaattaa agaaaattat   4260
aggacaggta agagatcagg ctgaacatct taagacagca gtacaaatgg cagtattcat   4320
ccacaatttt aaaagaaaag gggggattgg ggggtacagt gcaggggaaa gaatagtaga   4380
cataatagca acagacatac aaactaaaga attacaaaaa caaattacaa aaattcaaaa   4440
ttttcgggtt tattacaggg acagcagaga tccagtttgg aaaggaccag caaagctcct   4500
ctggaaaggt gaaggggcag tagtaataca agataatagt gacataaaag tagtgccaag   4560
aagaaaagca aagatcatca gggattatgg aaaacagatg gcaggtgatg attgtgtggc   4620
aagtagacag gatgaggatt aacacatgga aaagattagt aaaacaccat atgtatattt   4680
caaggaaagc taaggactgg ttttatagac atcactatga aagtactaat ccaaaaataa   4740
gttcagaagt acacatccca ctaggggatg ctaaattagt aataacaaca tattggggtc   4800
tgcatacagg agaaagagac tggcatttgg gtcagggagt ctccatagaa tggaggaaaa   4860
agagatatag cacacaagta gaccctgacc tagcagacca actaattcat ctgcactatt   4920
ttgattgttt ttcagaatct gctataagaa ataccatatt aggacgtata gttagtccta   4980
ggtgtgaata tcaagcagga cataacaagg taggatctct acagtacttg gcactagcag   5040
cattaataaa accaaaacag ataaagccac ctttgcctag tgttaggaaa ctgacagagg   5100
acagatggaa caagccccag aagaccaagg gccacagagg gagccataca atgaatggac   5160
actagagctt ttagaggaac ttaagagtga agctgttaga cattttccta ggatatggct   5220
ccataactta ggacaacata tctatgaaac ttacggggat acttgggcag gagtggaagc   5280
cataataaga attctgcaac aactgctgtt tatccatttc agaattgggt gtcgacatag   5340
cagaataggc gttactcgac agaggagagc aagaaatgga gccagtagat cctagactag   5400
agccctggaa gcatccagga agtcagccta aaactgcttg taccaattgc tattgtaaaa   5460
agtgttgctt tcattgccaa gtttgtttca taacaaaagc cttaggcatc tcctatggca   5520
ggaagaagcg gagacagcga cgaagacctc ctcaaggcag tcagactcat caagtttctc   5580
tatcaaagca gtaagtaata catgtaatgc aacctataca aatagcaata gtagcattag   5640
tagtagcaat aataatagca atagttgtgt ggtccatagt aatcatagaa tataggaaaa   5700
tattaagaca aagaaaaata gacaggttaa ttgatagact aatagaaaga gcagaagaca   5760
gtggcaatga gagtgaagga gaaatatcag cacttgtgga gatgggggtg gagatggggc   5820
```

-continued

```
accatgctcc ttgggatgtt gatgatctgt agtgctacag aaaaattgtg ggtcacagtc   5880
tattatgggg tacctgtgtg gaaggaagca accaccactc tattttgtgc atcagatgct   5940
aaagcatatg atacagaggt acataatgtt tgggccacac atgcctgtgt acccacagac   6000
cccaacccac aagaagtagt attggtaaat gtgacagaaa attttaacat gtggaaaaat   6060
gacatggtag aacagatgca tgaggatata atcagtttat gggatcaaag cctaaagcca   6120
tgtgtaaaat taaccccact ctgtgttagt ttaaagtgca ctgatttgaa gaatgatact   6180
aataccaata gtagtagcgg gagaatgata atggagaaag gagagataaa aaactgctct   6240
ttcaatatca gcacaagcat aagaggtaag gtgcagaaag aatatgcatt tttttataaa   6300
cttgatataa taccaataga taatgatact accagctata cgttgacaag ttgtaacacc   6360
tcagtcatta cacaggcctg tccaaaggta tcctttgagc caattcccat acattattgt   6420
gccccggctg gttttgcgat tctaaaatgt aataataaga cgttcaatgg aacaggacca   6480
tgtacaaatg tcagcacagt acaatgtaca catggaatta ggccagtagt atcaactcaa   6540
ctgctgttaa atggcagtct agcagaagaa gaggtagtaa ttagatctgt caatttcacg   6600
gacaatgcta aaaccataat agtacagctg aacacatctg tagaaattaa ttgtacaaga   6660
cccaacaaca atacaagaaa aaaaatccgt atccagaggg gaccagggag agcatttgtt   6720
acaataggaa aaataggaaa tatgagacaa gcacattgta acattagtag agcaaaatgg   6780
aatgccactt taaaacagat agctagcaaa ttaagagaac aatttggaaa taataaaaca   6840
ataatcttta agcaatcctc aggaggggac ccagaaattg taacgcacag ttttaattgt   6900
ggaggggaat ttttctactg taattcaaca caactgttta atagtacttg gtttaatagt   6960
acttggagta ctgaagggtc aaataacact gaaggaagtg acacaatcac actcccatgc   7020
agaataaaac aatttataaa catgtggcag gaagtaggaa aagcaatgta tgcccctccc   7080
atcagcggac aaattagatg ttcatcaaat attacagggc tgctattaac aagagatggt   7140
ggtaataaca acaatgggtc cgagatcttc agacctggag gaggagatat gagggacaat   7200
tggagaagtg aattatataa atataaagta gtaaaaattg aaccattagg agtagcaccc   7260
accaaggcaa agagaagagt ggtgcagaga gaaaaaagag cagtgggaat aggagctttg   7320
ttccttgggt tcttgggagc agcaggaagc actatgggcg cagcgtcaat gacgctgacg   7380
gtacaggcca gacaattatt gtctggtata gtgcagcagc agaacaattt gctgagggct   7440
attgaggcgc aacagcatct gttgcaactc acagtctggg gcatcaagca gctccaggca   7500
agaatcctgg ctgtggaaag atacctaaag gatcaacagc tcctggggat ttggggttgc   7560
tctggaaaac tcatttgcac cactgctgtg ccttggaatg ctagttggag taataaatct   7620
ctggaacaga tttggaatca cacgacctgg atggagtggg acagagaaat taacaattac   7680
acaagcttaa tacactcctt aattgaagaa tcgcaaaacc agcaagaaaa gaatgaacaa   7740
gaattattgg aattagataa atgggcaagt ttgtggaatt ggtttaacat aacaaattgg   7800
ctgtggtata taaaattatt cataatgata gtaggaggct tggtaggttt aagaatagtt   7860
tttgctgtac tttctgtagt gaatagagtt aggcagggat attcaccatt atcgtttcag   7920
acccacctcc caatcccgag gggacccgac aggcccgaag gaatagaaga agaaggtgga   7980
gagagagaca gagacagatc cattcgatta gtgaacggat ccttagcact tatctgggac   8040
gatctgcgga gcctgtgcct cttcagctac caccgcttga gagacttact cttgattgta   8100
acgaggattg tggaacttct gggacgcagg gggtgggaag ccctcaaata ttggtggaat   8160
ctcctacaat attggagtca ggagctaaag aatagtgctg ttagcttgct caatgccaca   8220
```

gctatagcag tagctgaggg gacagatagg gttatagaag tagtacaaga agcttataga 8280
gctattcgcc acatacctag aagaatagga cagggcttgg aaaggatttt gctataagat 8340
gggtggcaag tggtcaaaaa gtagtgtggt tggatggcct gctgtaaggg aaagaatgag 8400
acgagctgag ccagcagcag atggggtggg agcagcatct cgagacctag aaaaacatgg 8460
agcaatcaca agtagcaaca cagcagctaa caatgctgct tgtgcctggc tagaagcaca 8520
agaggaggag aaggtgggtt ttccagtcac acctcaggta cctttaagac caatgactta 8580
caaggcagct gtagatctta gccacttttt aaaagaaaag gggggactgg aagggctaat 8640
tcactcccaa cgaagacaag atatccttga tctgtggatc taccacacac aaggctactt 8700
ccctgattgg cagaactaca caccaggacc agggatcaga tatccactga cctttggatg 8760
gcgctacaag ctagtaccag ttgagccaga gaagttagaa gaagccaaca aaggagagaa 8820
caccagcttg ttacaccctg tgagcctgca tggaatggat gacccggaga gagaagtgtt 8880
agagtggagg tttgacagcc gcctagcatt tcatcacgtg gcccgagagc tgcatccgga 8940
gtacttcaag aactgctgat atcgagcttg ctacaaggga ctttccgctg gggactttcc 9000
agggaggcgt ggcctgggcg ggactgggga gtggcgagcc ctcagatcct gcatataagc 9060
agctgctttt tgcctgtact gggtctctct ggttagacca gatctgagcc tgggagctct 9120
ctggctaact agggaaccca ctgcttaagc ctcaataaag cttgccttga gtgcttcaag 9180
tagtgtgtgc ccgtctgttg tgtgactctg gtaactagag atccctcaga cccttttagt 9240
cagtgtggaa aatctctagc agt 9263

<210> SEQ ID NO 8
<211> LENGTH: 126
<212> TYPE: RNA
<213> ORGANISM: Artificial Sequence
<220> FEATURE:
<223> OTHER INFORMATION: synthetic construct

<400> SEQUENCE: 8
agguauauug cuguugacag ugagcgacug uaaacugagc uugcucuacu gugaagccac 60 agaugguag agcaagcaca guuuaccgcu gccuacugcc ucggacuuca aggggcuugc 120
ggccgc 126

<210> SEQ ID NO 9
<211> LENGTH: 115
<212> TYPE: RNA
<213> ORGANISM: Artificial Sequence
<220> FEATURE:
<223> OTHER INFORMATION: synthetic construct

<400> SEQUENCE: 9
caucuccaug gcuguaccac cuugucggcc ugcuauguca cuuccccuac uguugaaucu 60
cauggagggg aagugccaua gcagcucuga cauuuuggua ucuuucaucu gacca 115

<210> SEQ ID NO 10
<211> LENGTH: 115
<212> TYPE: RNA
<213> ORGANISM: Artificial Sequence
<220> FEATURE:
<223> OTHER INFORMATION: synthetic construct

<400> SEQUENCE: 10
gggccuggcu cgagcagggg gcgagggauu gacuuugggg auuguagggg augguccccu 60 ccccccuac aaucgccaaa guccguccuu cccucccaau gaccgcgucu ucguc 115

<210> SEQ ID NO 11
<211> LENGTH: 116
<212> TYPE: RNA
<213> ORGANISM: Artificial Sequence
<220> FEATURE:
<223> OTHER INFORMATION: synthetic construct

<400> SEQUENCE: 11
cagcggcggc uccucucccc auggcccugg ggauguguac uucugaacuu gcugggcuca 60
gaccaguuca gaagaacaca uccgcaggga ccuggggacc ccggcaccgg caggcc 116

<210> SEQ ID NO 12
<211> LENGTH: 119
<212> TYPE: RNA
<213> ORGANISM: Artificial Sequence
<220> FEATURE:
<223> OTHER INFORMATION: synthetic construct

<400> SEQUENCE: 12
cucuaucuga ugugacagcu ucuguagcac uucuucugcu agacugccau aguguuuagu 60
uaucuauggc agucucgcag aagacguacu gcuagcugua gaacuccagc uucggccuu 119

<210> SEQ ID NO 13
<211> LENGTH: 121
<212> TYPE: RNA
<213> ORGANISM: Artificial Sequence
<220> FEATURE:
<223> OTHER INFORMATION: synthetic construct

<400> SEQUENCE: 13
aacuuaugau agcaauguca gcagugccuu ccgcuucuuc cugccauagc guuaagauuc 60
uaaaauuauc ucuauggcag gcagaagcgg caaguaaggu ugaccauacu cuacaguugu 120
u 121

<210> SEQ ID NO 14
<211> LENGTH: 123
<212> TYPE: RNA
<213> ORGANISM: Artificial Sequence
<220> FEATURE:
<223> OTHER INFORMATION: synthetic construct

<400> SEQUENCE: 14
uucguggcua cagaguuucc uuagcagagc uguaucaucu gcuccuguau cuugugucua 60
aacuaucaag auacaggacc agaugaucua gcuacugcua ggcaauccuu cccucgauaa 120
aug 123

<210> SEQ ID NO 15
<211> LENGTH: 28
<212> TYPE: RNA
<213> ORGANISM: Artificial Sequence
<220> FEATURE:
<223> OTHER INFORMATION: synthetic construct

<400> SEQUENCE: 15
agguauauug cuguugacag ugagcgac 28

<210> SEQ ID NO 16
<211> LENGTH: 22
<212> TYPE: RNA
<213> ORGANISM: Artificial Sequence
<220> FEATURE:
<223> OTHER INFORMATION: synthetic construct

<400> SEQUENCE: 16
uguaaacuga gcuugcucua cu 22

<210> SEQ ID NO 17
<211> LENGTH: 30
<212> TYPE: RNA
<213> ORGANISM: Artificial Sequence
<220> FEATURE:
<223> OTHER INFORMATION: synthetic construct

<400> SEQUENCE: 17
gugaagccac agauggggcu gccuacugcc 30

<210> SEQ ID NO 18
<211> LENGTH: 20
<212> TYPE: RNA
<213> ORGANISM: Artificial Sequence
<220> FEATURE:
<223> OTHER INFORMATION: synthetic construct

<400> SEQUENCE: 18
uagagcaagc acaguuuacc 20

<210> SEQ ID NO 19
<211> LENGTH: 26
<212> TYPE: RNA
<213> ORGANISM: Artificial Sequence
<220> FEATURE:
<223> OTHER INFORMATION: synthetic construct

<400> SEQUENCE: 19
ucggacuuca aggggcuugc ggccgc 26

<210> SEQ ID NO 20
<211> LENGTH: 28
<212> TYPE: RNA
<213> ORGANISM: Artificial Sequence
<220> FEATURE:
<223> OTHER INFORMATION: synthetic construct

<400> SEQUENCE: 20
caucuccaug gcuguaccac cuugucgg 28

<210> SEQ ID NO 21
<211> LENGTH: 22
<212> TYPE: RNA
<213> ORGANISM: Artificial Sequence
<220> FEATURE:
<223> OTHER INFORMATION: synthetic construct

<400> SEQUENCE: 21
ccugcuaugu cacuuccccu ac 22

<210> SEQ ID NO 22
<211> LENGTH: 15
<212> TYPE: RNA
<213> ORGANISM: Artificial Sequence
<220> FEATURE:
<223> OTHER INFORMATION: synthetic construct

<400> SEQUENCE: 22
uguugaaucu caugg 15

<210> SEQ ID NO 23
<211> LENGTH: 20
<212> TYPE: RNA
<213> ORGANISM: Artificial Sequence
<220> FEATURE:
<223> OTHER INFORMATION: synthetic construct

<400> SEQUENCE: 23
aggggaagug ccauagcagc 20

<210> SEQ ID NO 24
<211> LENGTH: 30
<212> TYPE: RNA
<213> ORGANISM: Artificial Sequence
<220> FEATURE:
<223> OTHER INFORMATION: synthetic construct

<400> SEQUENCE: 24
ucugacauuu ugguaucuuu caucugacca 30

<210> SEQ ID NO 25
<211> LENGTH: 29
<212> TYPE: RNA
<213> ORGANISM: Artificial Sequence
<220> FEATURE:
<223> OTHER INFORMATION: sythetic structure

<400> SEQUENCE: 25
gggccuggcu cgagcagggg gcgagggau 29

<210> SEQ ID NO 26
<211> LENGTH: 22
<212> TYPE: RNA
<213> ORGANISM: Artificial Sequence
<220> FEATURE:
<223> OTHER INFORMATION: synthetic structure

<400> SEQUENCE: 26
ugacuuuggg gauuguaggg ga 22

<210> SEQ ID NO 27
<211> LENGTH: 13
<212> TYPE: RNA
<213> ORGANISM: Artificial Sequence
<220> FEATURE:
<223> OTHER INFORMATION: synthetic structure

<400> SEQUENCE: 27
ugguccccuc ccc 13

<210> SEQ ID NO 28
<211> LENGTH: 19
<212> TYPE: RNA
<213> ORGANISM: Artificial Sequence
<220> FEATURE:
<223> OTHER INFORMATION: synthetic structure

<400> SEQUENCE: 28
cccuacaauc gccaaaguc 19

<210> SEQ ID NO 29
<211> LENGTH: 32
<212> TYPE: RNA
<213> ORGANISM: Artificial Sequence
<220> FEATURE:
<223> OTHER INFORMATION: synthetic construct

<400> SEQUENCE: 29
cguccuuccc ucccaaugac cgcgucuucg uc 32

<210> SEQ ID NO 30
<211> LENGTH: 29
<212> TYPE: RNA
<213> ORGANISM: Artificial Sequence
<220> FEATURE:
<223> OTHER INFORMATION: synthetic construct

<400> SEQUENCE: 30
cagcggcggc uccucucccc auggcccug 29

<210> SEQ ID NO 31
<211> LENGTH: 22
<212> TYPE: RNA
<213> ORGANISM: Artificial Sequence
<220> FEATURE:
<223> OTHER INFORMATION: synthetic construct

<400> SEQUENCE: 31
gggaugugua cuucugaacu ug 22

<210> SEQ ID NO 32
<211> LENGTH: 13
<212> TYPE: RNA
<213> ORGANISM: Artificial Sequence
<220> FEATURE:
<223> OTHER INFORMATION: synthetic construct

<400> SEQUENCE: 32
cugggcucag acc 13

<210> SEQ ID NO 33
<211> LENGTH: 20
<212> TYPE: RNA
<213> ORGANISM: Artificial Sequence
<220> FEATURE:
<223> OTHER INFORMATION: synthetic construct

<400> SEQUENCE: 33
aguucagaag aacacauccg 20

<210> SEQ ID NO 34
<211> LENGTH: 32
<212> TYPE: RNA
<213> ORGANISM: Artificial Sequence
<220> FEATURE:
<223> OTHER INFORMATION: synthetic construct

<400> SEQUENCE: 34
cagggaccug gggaccccgg caccggcagg cc 32

<210> SEQ ID NO 35
<211> LENGTH: 30
<212> TYPE: RNA
<213> ORGANISM: Artificial Sequence
<220> FEATURE:
<223> OTHER INFORMATION: synthetic construct

<400> SEQUENCE: 35
cucuaucuga ugugacagcu ucuguagcac 30

<210> SEQ ID NO 36

-continued

<211> LENGTH: 22
<212> TYPE: RNA
<213> ORGANISM: Artificial Sequence
<220> FEATURE:
<223> OTHER INFORMATION: synthetic region

<400> SEQUENCE: 36
uucuucugcu agacugccau ag 22

<210> SEQ ID NO 37
<211> LENGTH: 13
<212> TYPE: RNA
<213> ORGANISM: Artificial Sequence
<220> FEATURE:
<223> OTHER INFORMATION: synthetic construct

<400> SEQUENCE: 37
uguuuaguua ucu 13

<210> SEQ ID NO 38
<211> LENGTH: 20
<212> TYPE: RNA
<213> ORGANISM: Artificial Sequence
<220> FEATURE:
<223> OTHER INFORMATION: synthetic construct

<400> SEQUENCE: 38
auggcagucu cgcagaagac 20

<210> SEQ ID NO 39
<211> LENGTH: 34
<212> TYPE: RNA
<213> ORGANISM: Artificial Sequence
<220> FEATURE:
<223> OTHER INFORMATION: synthetic construct

<400> SEQUENCE: 39
guacugcuag cuguagaacu ccagcuucgg ccuu 34

<210> SEQ ID NO 40
<211> LENGTH: 29
<212> TYPE: RNA
<213> ORGANISM: Artificial Sequence
<220> FEATURE:
<223> OTHER INFORMATION: synthetic construct

<400> SEQUENCE: 40
aacuuaugau agcaauguca gcagugccu 29

<210> SEQ ID NO 41
<211> LENGTH: 22
<212> TYPE: RNA
<213> ORGANISM: Artificial Sequence
<220> FEATURE:
<223> OTHER INFORMATION: synthetic construct

<400> SEQUENCE: 41
uccgcuucuu ccugccauag cg 22

<210> SEQ ID NO 42
<211> LENGTH: 20
<212> TYPE: RNA
<213> ORGANISM: Artificial Sequence
<220> FEATURE:
<223> OTHER INFORMATION: synthetic construct

<400> SEQUENCE: 42

-continued uuaagauucu aaaauuaucu 20

<210> SEQ ID NO 43
<211> LENGTH: 20
<212> TYPE: RNA
<213> ORGANISM: Artificial Sequence
<220> FEATURE:
<223> OTHER INFORMATION: synthetic construct

<400> SEQUENCE: 43
cuauggcagg cagaagcggc 20

<210> SEQ ID NO 44
<211> LENGTH: 30
<212> TYPE: RNA
<213> ORGANISM: Artificial Sequence
<220> FEATURE:
<223> OTHER INFORMATION: synthetic construct

<400> SEQUENCE: 44
aaguaagguu gaccauacuc uacaguuguu 30

<210> SEQ ID NO 45
<211> LENGTH: 32
<212> TYPE: RNA
<213> ORGANISM: Artificial Sequence
<220> FEATURE:
<223> OTHER INFORMATION: synthetic construct

<400> SEQUENCE: 45
uucguggcua cagaguuucc uuagcagagc ug 32

<210> SEQ ID NO 46
<211> LENGTH: 22
<212> TYPE: RNA
<213> ORGANISM: Artificial Sequence
<220> FEATURE:
<223> OTHER INFORMATION: synthetic construct

<400> SEQUENCE: 46
uaucaucugc uccuguaucu ug 22

<210> SEQ ID NO 47
<211> LENGTH: 14
<212> TYPE: RNA
<213> ORGANISM: Artificial Sequence
<220> FEATURE:
<223> OTHER INFORMATION: synthetic construct

<400> SEQUENCE: 47
ugucuaaacu auca 14

<210> SEQ ID NO 48
<211> LENGTH: 20
<212> TYPE: RNA
<213> ORGANISM: Artificial Sequence
<220> FEATURE:
<223> OTHER INFORMATION: sythetic construct

<400> SEQUENCE: 48
agauacagga ccagaugauc 20

<210> SEQ ID NO 49
<211> LENGTH: 35
<212> TYPE: RNA

<213> ORGANISM: Artificial Sequence
<220> FEATURE:
<223> OTHER INFORMATION: synthetic construct

<400> SEQUENCE: 49
uagcuacugc uaggcaaucc uucccucgau aaaug 35

<210> SEQ ID NO 50
<211> LENGTH: 60
<212> TYPE: DNA
<213> ORGANISM: Artificial Sequence
<220> FEATURE:
<223> OTHER INFORMATION: Synthetic construct

<400> SEQUENCE: 50
agcttccagt cgaggatgtt tacagctaca gtactgagct tccagtcgag gatgtttaca 60

<210> SEQ ID NO 51
<211> LENGTH: 60
<212> TYPE: DNA
<213> ORGANISM: Artificial Sequence
<220> FEATURE:
<223> OTHER INFORMATION: synthetic construct

<400> SEQUENCE: 51
tcgacactgg tacaacggtt gggagaagtc acgtgtacca ctggtacaac ggttgggaga 60

<210> SEQ ID NO 52
<211> LENGTH: 51
<212> TYPE: DNA
<213> ORGANISM: Artificial Sequence
<220> FEATURE:
<223> OTHER INFORMATION: synthetic construct

<400> SEQUENCE: 52
agttcagaag tacacatccc gctacagtac tagttcagaa gtacacatcc c 51

<210> SEQ ID NO 53
<211> LENGTH: 57
<212> TYPE: DNA
<213> ORGANISM: Artificial Sequence
<220> FEATURE:
<223> OTHER INFORMATION: synthetic construct

<400> SEQUENCE: 53
cgagcaagct cagtttacac cgctacagta ctggcgagca agctcagttt acaccgc 57

<210> SEQ ID NO 54
<211> LENGTH: 49
<212> TYPE: DNA
<213> ORGANISM: Artificial Sequence
<220> FEATURE:
<223> OTHER INFORMATION: synthetic construct

<400> SEQUENCE: 54
aggggaagtg acatagcagg atgctcagag gggaagtgac atagcaggc 49

<210> SEQ ID NO 55
<211> LENGTH: 50
<212> TYPE: DNA
<213> ORGANISM: Artificial Sequence
<220> FEATURE:
<223> OTHER INFORMATION: synthetic construct

<400> SEQUENCE: 55
atggcagtct agcagaagaa atgctcagat ggcagtctag cagaagaagc 50

<210> SEQ ID NO 56
<211> LENGTH: 50
<212> TYPE: DNA
<213> ORGANISM: Artificial Sequence
<220> FEATURE:
<223> OTHER INFORMATION: synthetic construct

<400> SEQUENCE: 56
ctatggcagg aagaagcgga atgctcagct atggcaggaa gaagcggagc 50

<210> SEQ ID NO 57
<211> LENGTH: 50
<212> TYPE: DNA
<213> ORGANISM: Artificial Sequence
<220> FEATURE:
<223> OTHER INFORMATION: synthetic construct

<400> SEQUENCE: 57
ccctacaatc cccaaagtca atgctcagcc ctacaatccc caaagtcagc 50

<210> SEQ ID NO 58
<211> LENGTH: 50
<212> TYPE: DNA
<213> ORGANISM: Artificial Sequence
<220> FEATURE:
<223> OTHER INFORMATION: synthetic construct

<400> SEQUENCE: 58
agatacagga gcagatgata atgctcagag atacaggagc agatgatagc 50

<210> SEQ ID NO 59
<211> LENGTH: 363
<212> TYPE: DNA
<213> ORGANISM: Artificial Sequence
<220> FEATURE:
<223> OTHER INFORMATION: synthetic construct

<400> SEQUENCE: 59
gacattttct agaatattgc tgtttgaatg aggcttcagt actttacaga atcgttgcct 60
gcacatcttg gaaacacttg ctgggattac ttcttcaggt taacccaaca gaaggctaaa 120
gaaggtatat tgctgttgac agtgagcgac tgtaaacatc ctcgactgga agctgtgaag 180
ccacagatgg gctttcagtc ggatgtttgc agctgcctac tgcctcggac ttcaaggggc 240
tactttagga gcaattatct tgtttactaa aactgaatac cttgctatct ctttgataca 300
tttttacaaa gctgaattaa aatggtataa attaaatcac tttaaaacca tgtctgtaca 360
ttt 363

<210> SEQ ID NO 60
<211> LENGTH: 123
<212> TYPE: DNA
<213> ORGANISM: Artificial Sequence
<220> FEATURE:
<223> OTHER INFORMATION: synthetic construct

<400> SEQUENCE: 60
gaaggtatat tgctgttgac agtgagcgac tgtaaacatc ctcgactgga agctgtgaag 60
ccacagatgg gctttcagtc ggatgtttgc agctgcctac tgcctcggac ttcaaggggc 120
tac 123

<210> SEQ ID NO 61

<211> LENGTH: 103
<212> TYPE: DNA
<213> ORGANISM: Artificial Sequence
<220> FEATURE:
<223> OTHER INFORMATION: synthetic construct

<400> SEQUENCE: 61
tgctgttgac agtgagcgac tgtaaacatc ctcgactgga agctgtgaag ccacagatgg 60
gctttcagtc ggatgtttgc agctgcctac tgcctcggac ttc 103

<210> SEQ ID NO 62
<211> LENGTH: 93
<212> TYPE: DNA
<213> ORGANISM: Artificial Sequence
<220> FEATURE:
<223> OTHER INFORMATION: synthetic construct

<400> SEQUENCE: 62
ttgacagtga gcgactgtaa acatcctcga ctggaagctg tgaagccaca gatgggcttt 60
cagtcggatg tttgcagctg cctactgcct cgg 93

<210> SEQ ID NO 63
<211> LENGTH: 176
<212> TYPE: DNA
<213> ORGANISM: Artificial Sequence
<220> FEATURE:
<223> OTHER INFORMATION: synthetic construct

<400> SEQUENCE: 63
cggggaggca gcgtccccga ggcagcagcg gcagcggcgg ctcctctccc catggccctg 60
tctcccaacc cttgtaccag tgctgggctc agaccctggt acaggcctgg gggacaggga 120
cctggggacc ccggcaccgg caggccccaa ggggtgaggt gagcgggcat tgggac 176

<210> SEQ ID NO 64
<211> LENGTH: 116
<212> TYPE: DNA
<213> ORGANISM: Artificial Sequence
<220> FEATURE:
<223> OTHER INFORMATION: synthetic construct

<400> SEQUENCE: 64
gcagcggcgg ctcctctccc catggccctg tctcccaacc cttgtaccag tgctgggctc 60
agaccctggt acaggcctgg gggacaggga cctggggacc ccggcaccgg caggcc 116

<210> SEQ ID NO 65
<211> LENGTH: 96
<212> TYPE: DNA
<213> ORGANISM: Artificial Sequence
<220> FEATURE:
<223> OTHER INFORMATION: synthetic construct

<400> SEQUENCE: 65
ctcctctccc catggccctg tctcccaacc cttgtaccag tgctgggctc agaccctggt 60
acaggcctgg gggacaggga cctggggacc ccggca 96

<210> SEQ ID NO 66
<211> LENGTH: 86
<212> TYPE: DNA
<213> ORGANISM: Artificial Sequence
<220> FEATURE:
<223> OTHER INFORMATION: synthetic construct

<400> SEQUENCE: 66
ctccccatgg ccctgtctcc caacccttgt accagtgctg ggctcagacc ctggtacagg 60
cctgggggac agggacctgg ggaccc 86

<210> SEQ ID NO 67
<211> LENGTH: 20
<212> TYPE: DNA
<213> ORGANISM: Artificial Sequence
<220> FEATURE:
<223> OTHER INFORMATION: synthetic construct

<400> SEQUENCE: 67
tgttgctttc attgccaagt 20

<210> SEQ ID NO 68
<211> LENGTH: 21
<212> TYPE: DNA
<213> ORGANISM: Artificial Sequence
<220> FEATURE:
<223> OTHER INFORMATION: synthetic construct

<400> SEQUENCE: 68
tgatgagtct gactgccttg a 21

<210> SEQ ID NO 69
<211> LENGTH: 20
<212> TYPE: RNA
<213> ORGANISM: Artificial Sequence
<220> FEATURE:
<223> OTHER INFORMATION: synthetic construct

<400> SEQUENCE: 69
cuauggcagg aagaagcgga 20

<210> SEQ ID NO 70
<211> LENGTH: 20
<212> TYPE: RNA
<213> ORGANISM: Artificial Sequence
<220> FEATURE:
<223> OTHER INFORMATION: synthetic construct

<400> SEQUENCE: 70
cuauggcagg aagaagcgga 20

<210> SEQ ID NO 71
<211> LENGTH: 20
<212> TYPE: RNA
<213> ORGANISM: Artificial Sequence
<220> FEATURE:
<223> OTHER INFORMATION: synthetic construct

<400> SEQUENCE: 71
cuauggcagg aagaagcaga 20

<210> SEQ ID NO 72
<211> LENGTH: 20
<212> TYPE: RNA
<213> ORGANISM: Artificial Sequence
<220> FEATURE:
<223> OTHER INFORMATION: synthetic construct

<400> SEQUENCE: 72
cuacggcagg aagaagcgga 20

<210> SEQ ID NO 73

<211> LENGTH: 93
<212> TYPE: RNA
<213> ORGANISM: Artificial Sequence
<220> FEATURE:
<223> OTHER INFORMATION: synthetic construct

<400> SEQUENCE: 73
uguugacagu gagcgacugu aaacugagcu ugcucuacug ugaagccaca gauggguaga 60
gcaagcacag uuuaccgcug ccuacugccu ccg 93

<210> SEQ ID NO 74
<211> LENGTH: 91
<212> TYPE: RNA
<213> ORGANISM: Artificial Sequence
<220> FEATURE:
<223> OTHER INFORMATION: synthetic construct

<400> SEQUENCE: 74
uguaccaccu ugucggccug cuaugucacu uccccuacug uugaaucuca uggaggggaa 60
gugccauagc agcucugaca uuuugguauc u 91

<210> SEQ ID NO 75
<211> LENGTH: 88
<212> TYPE: RNA
<213> ORGANISM: Artificial Sequence
<220> FEATURE:
<223> OTHER INFORMATION: synthetic construct

<400> SEQUENCE: 75
gacagcuucu guagcacuuc uucugcuaga cugccauagu guuuaguuau cuauggcagu 60
cucgcagaag acguacugcu agcuguag 88

<210> SEQ ID NO 76
<211> LENGTH: 92
<212> TYPE: RNA
<213> ORGANISM: Artificial Sequence
<220> FEATURE:
<223> OTHER INFORMATION: synthetic construct

<400> SEQUENCE: 76
ugucagcagu gccuuuccgc uucuuccugc cauagcguua agauucuaaa auuaucuaua 60
uggcaggcag aagcggcaag uaagguugac ca 92

<210> SEQ ID NO 77
<211> LENGTH: 88
<212> TYPE: RNA
<213> ORGANISM: Artificial Sequence
<220> FEATURE:
<223> OTHER INFORMATION: synthetic construct

<400> SEQUENCE: 77
uuccuuagca gagcuguauc aucugcuccu guaucuugug ucuaaacuau caagauacag 60
gaccagauga ucuagcuacu gcuaggca 88

<210> SEQ ID NO 78
<211> LENGTH: 83
<212> TYPE: RNA
<213> ORGANISM: Artificial Sequence
<220> FEATURE:
<223> OTHER INFORMATION: synthetic construct

<400> SEQUENCE: 78
gcagggggcg agggauugac uuuggggauu guaggggaug guccccuccc ccccuacgcc 60
aaaguccguc cuucccuccc aau 83

<210> SEQ ID NO 79
<211> LENGTH: 85
<212> TYPE: RNA
<213> ORGANISM: Artificial Sequence
<220> FEATURE:
<223> OTHER INFORMATION: synthetic construct

<400> SEQUENCE: 79
cuccccaugg cccuggggau guguacuucu gaacuugcug ggcucagaca aguucagaag 60
aacacauccg cagggaccug gggac 85

<210> SEQ ID NO 80
<211> LENGTH: 22
<212> TYPE: RNA
<213> ORGANISM: Artificial Sequence
<220> FEATURE:
<223> OTHER INFORMATION: synthetic construct

<400> SEQUENCE: 80
uguaaacuga gcuugcucua cu 22

<210> SEQ ID NO 81
<211> LENGTH: 22
<212> TYPE: RNA
<213> ORGANISM: Artificial Sequence
<220> FEATURE:
<223> OTHER INFORMATION: synthetic construct

<400> SEQUENCE: 81
uguaaacuga gcuugcucua cu 22

<210> SEQ ID NO 82
<211> LENGTH: 22
<212> TYPE: RNA
<213> ORGANISM: Artificial Sequence
<220> FEATURE:
<223> OTHER INFORMATION: synthetic construct

<400> SEQUENCE: 82
uguaaacuga gcuugcucua cu 22

<210> SEQ ID NO 83
<211> LENGTH: 22
<212> TYPE: RNA
<213> ORGANISM: Artificial Sequence
<220> FEATURE:
<223> OTHER INFORMATION: synthetic construct

<400> SEQUENCE: 83
uguaaacuga gcuugcucua cu 22

<210> SEQ ID NO 84
<211> LENGTH: 22
<212> TYPE: RNA
<213> ORGANISM: Artificial Sequence
<220> FEATURE:
<223> OTHER INFORMATION: synthetic construct

<400> SEQUENCE: 84
ccugcuaugu cacuuccccu ac 22

<210> SEQ ID NO 85

-continued

<211> LENGTH: 22
<212> TYPE: RNA
<213> ORGANISM: Artificial Sequence
<220> FEATURE:
<223> OTHER INFORMATION: synthetic construct

<400> SEQUENCE: 85
uguaaacuga gcuugcucua cu 22

<210> SEQ ID NO 86
<211> LENGTH: 22
<212> TYPE: RNA
<213> ORGANISM: Artificial Sequence
<220> FEATURE:
<223> OTHER INFORMATION: synthetic construct

<400> SEQUENCE: 86
uguaaacuga gcuugcucua cu 22

<210> SEQ ID NO 87
<211> LENGTH: 22
<212> TYPE: RNA
<213> ORGANISM: Artificial Sequence
<220> FEATURE:
<223> OTHER INFORMATION: synthetic construct

<400> SEQUENCE: 87
cuucuucugc uagacugcca ua 22

<210> SEQ ID NO 88
<211> LENGTH: 22
<212> TYPE: RNA
<213> ORGANISM: Artificial Sequence
<220> FEATURE:
<223> OTHER INFORMATION: synthetic construct

<400> SEQUENCE: 88
uucuucugcu agacugccau ag 22

<210> SEQ ID NO 89
<211> LENGTH: 22
<212> TYPE: RNA
<213> ORGANISM: Artificial Sequence
<220> FEATURE:
<223> OTHER INFORMATION: synthetic construct

<400> SEQUENCE: 89
cuucuucugc uagacugcca ua 22

<210> SEQ ID NO 90
<211> LENGTH: 22
<212> TYPE: RNA
<213> ORGANISM: Artificial Sequence
<220> FEATURE:
<223> OTHER INFORMATION: synthetic construct

<400> SEQUENCE: 90
uucuucugcu agacugccau ag 22

<210> SEQ ID NO 91
<211> LENGTH: 22
<212> TYPE: RNA
<213> ORGANISM: Artificial Sequence
<220> FEATURE:
<223> OTHER INFORMATION: synthetic construct

<400> SEQUENCE: 91
uccgcuucuu ccugccauag cg 22

<210> SEQ ID NO 92
<211> LENGTH: 22
<212> TYPE: RNA
<213> ORGANISM: Artificial Sequence
<220> FEATURE:
<223> OTHER INFORMATION: synthetic construct

<400> SEQUENCE: 92
uccgcuucuu ccugccauag cg 22

<210> SEQ ID NO 93
<211> LENGTH: 22
<212> TYPE: RNA
<213> ORGANISM: Artificial Sequence
<220> FEATURE:
<223> OTHER INFORMATION: synthetic construct

<400> SEQUENCE: 93
uaucaucugc uccuguaucu ug 22

<210> SEQ ID NO 94
<211> LENGTH: 22
<212> TYPE: RNA
<213> ORGANISM: Artificial Sequence
<220> FEATURE:
<223> OTHER INFORMATION: synthetic construct

<400> SEQUENCE: 94
uaucaucugc uccuguaucu ug 22

<210> SEQ ID NO 95
<211> LENGTH: 22
<212> TYPE: RNA
<213> ORGANISM: Artificial Sequence
<220> FEATURE:
<223> OTHER INFORMATION: synthetic construct

<400> SEQUENCE: 95
ugacuuuggg gauuguaggg ga 22

<210> SEQ ID NO 96
<211> LENGTH: 22
<212> TYPE: RNA
<213> ORGANISM: Artificial Sequence
<220> FEATURE:
<223> OTHER INFORMATION: synthetic construct

<400> SEQUENCE: 96
ugacuuuggg gauuguaggg ga 22

<210> SEQ ID NO 97
<211> LENGTH: 22
<212> TYPE: RNA
<213> ORGANISM: Artificial Sequence
<220> FEATURE:
<223> OTHER INFORMATION: synthetic construct

<400> SEQUENCE: 97
ugacuuuggg gauuguaggg ga 22

<210> SEQ ID NO 98
<211> LENGTH: 22
<212> TYPE: RNA

-continued

```
<213> ORGANISM: Artificial Sequence
<220> FEATURE:
<223> OTHER INFORMATION: synthetic construct

<400> SEQUENCE: 98

gggaugugua cuucugaacu ug                                        22


<210> SEQ ID NO 99
<211> LENGTH: 22
<212> TYPE: RNA
<213> ORGANISM: Artificial Sequence
<220> FEATURE:
<223> OTHER INFORMATION: synthetic construct

<400> SEQUENCE: 99

gggaugugua cuucugaacu ug                                        22


<210> SEQ ID NO 100
<211> LENGTH: 22
<212> TYPE: RNA
<213> ORGANISM: Artificial Sequence
<220> FEATURE:
<223> OTHER INFORMATION: synthetic construct

<400> SEQUENCE: 100

gggaugugua cuucugaacu ug                                        22


<210> SEQ ID NO 101
<211> LENGTH: 22
<212> TYPE: RNA
<213> ORGANISM: Artificial Sequence
<220> FEATURE:
<223> OTHER INFORMATION: synthetic construct

<400> SEQUENCE: 101

gggaugugua cuucugaacu ug                                        22
```

MULTIPLEXED SHRNAS AND USES THEREOF

CROSS REFERENCE TO RELATED APPLICATIONS

This application is the US national phase of International Application No. PCT/US2015/055537, filed on Oct. 14, 2015 under the PCT (Patent Cooperation Treaty), and claims priority to U.S. Provisional Patent Application Nos. 62/063,583, filed Oct. 14, 2014, and 62/240,709, filed on Oct. 13, 2015. The entire contents of these applications are incorporated herein by reference.

FIELD OF THE INVENTION

The disclosure relates to multiplexed shRNAs and uses thereof.

BACKGROUND

Following successful clinical trials, there has been a resurgence of interest in using ribonucleic acid interference (RNAi) to treat many diseases including cancer and HIV-1 infection (Davidson and McCray (2011). Nat Rev Genet 12: 329-340). Although short hairpin RNAs (shRNA) can be used to inhibit human immunodeficiency virus (HIV-1) replication (Lee et al. (2005). Blood 106: 818-826; Lee et al. (2002). Nat Biotechnol 20: 500-505; DiGiusto et al. (2010). Sci Transl Med 2: 36ra43), one potential problem of shRNAs expressed under the commonly used Pol III promoters is that the overexpressed shRNA can cause toxicities by competing with endogenous microRNAs (miRNAs) for cytoplasmic transport (Grimm et al. (2006). Nature 441: 537-541; McBride et al. (2008). Proc Nati Acad Sci USA 105: 5868-5873; Boudreau et al. (2008) RNA 14: 1834-1844). Moreover, shRNAs in the cytoplasm that are processed by the Dicer enzyme can also bind all Ago proteins, further compromising endogenous miRNA function (Grimm et al. (2010). J Clin Invest 120: 3106-3119).

A major concern in using traditional shRNA for HIV-1 therapy is the rapid emergence of escape mutations since HIV-1 evolves very quickly due to highly error-prone reverse transcription (Boden et al. (2003). J Virol 77: 11531-11535; Das et al. (2004). J Virol 78: 2601-2605). Therefore, to minimize this problem, it is important to be able to express multiple shRNAs in a single vector to target host factors and viral genes. However, attempts to express multiple shRNAs using tandem repeats of the same promoter were unsuccessful because the cassettes were prone for deletion due to homologous recombination (Brake et al. (2008). Mol Ther 16: 557-564). Similarly, expression of multiple shRNAs using the same miRNA backbone is also likely to lead to deletion by homologous recombination. Alternatively, multiple shRNAs may be expressed using the naturally occurring polycistronic miRNA clusters (Liu et al. (2008). Nucleic Acids Res 36: 2811-2824; Aagaard et al. (2008). Gene Ther 15: 1536-1549; Chung et al. (2012). Hum Gene Ther 23: 1200-1208). However, currently the maximum number of shRNAs that can be expressed in a polycistronic miRNA backbone is limited (Liu et al. (2008). Nucleic Acids Res 36: 2811-2824). Although mathematical modeling suggests that a combination of four shRNAs may be sufficient to overcome escape, this requires all four shRNAs to be matched to each of the circulating 100's of viral variants and the viral quasispecies present in patients (McIntyre et al. (2011). AIDS Res Ther 8: 1).

MiRNAs are transcribed as long (up to several kb) primary miRNAs (pri-miRNAs) containing the miRNA duplex with long 5' and 3' flanking sequences (Lee et al. (2004). EMBO J 23: 4051-4060; Cai et al. (2004). RNA 10: 1957-1966). Pri-miRNAs are processed in the nucleus by Drosha/DGCR8 complex to generate pre-miRNAs, which are then exported to the cytoplasm for further processing by Dicer to generate mature miRNAs (Lee et al. (2003). Nature 425: 415-419; Han et al. (2004). Genes Dev 18: 3016-3027). Generally, long stretches of flanking sequences are used to design shRNAs in a endogenous miRNA backbone (shRNA-miRs) in the hope that it will lead to processing by Drosha/DGCR8, just like primary miRNAs (Chang et al. (2006). Nat Methods 3: 707-714). However, multiplexing shRNAs with different miRNA backbones by this method is impractical because of the long stretches of flanking sequences.

Delivery of shRNA to the relevant (HIV-1 susceptible) target cells in vivo remains a great challenge. It is a common strategy to deliver shRNA via a VSV-G pseudotyped lentiviral vector because the VSV receptor is ubiquitously expressed in most cell types. VSV-G pseudotyping allows transduction of many different cell types. However, CD4 T cells, the major targets of HIV-1, can be transduced by VSV-G pseudotyped lentivirus only after activation, which could impact their repertoire and long-term survival (Agosto et al. (2009). J Virol 83: 8153-8162; Yu et al. (2009). PLoS Pathog 5: e1000633).

In spite of current therapies, the need exists for developing novel therapies that treat and prevent HIV and AIDS.

SUMMARY

The disclosure provides, at least in part, nucleic acid molecules such as shRNA dusters encoding shRNA-like molecules and artificial miRNA clusters encoding modified pri-miRNA-like molecules. The shRNA clusters and artificial miRNA clusters disclosed herein can be used, for example, to produce artificial RNA molecules, e.g., RNAi molecules. Cells, viral particles, compositions (e.g., pharmaceutical compositions), kits, and methods relating to the nucleic acid molecules, e.g., shRNA clusters and artificial miRNA clusters, are also disclosed. The nucleic acid molecules (e.g., shRNA clusters and artificial miRNA clusters), artificial RNA molecules (e.g., RNAi molecules), cells, viral particles, compositions (e.g., pharmaceutical compositions), and kits and methods disclosed herein can be used to treat or prevent a disease, e.g., HIV infection and/or AIDS.

In an aspect, the disclosure features a nucleic acid molecule, e.g., an shRNA duster, encoding a plurality of shRNA-like molecules, wherein each of the plurality of shRNA-like molecules comprises: a stem region comprising an artificial RNA molecule comprising a guide strand and a passenger strand, wherein the guide strand is substantially complementary to a target mRNA; and a backbone region comprising a 5' flanking region, a terminal loop region, and a 3' flanking region.

In an embodiment, the backbone region of at least one shRNA-like molecule is not repeated among the plurality of shRNA-like molecules, e.g., the plurality of shRNA-like molecules do not include backbone regions that are identical or substantially identical. In an embodiment, the backbone regions of the plurality of shRNA-like molecules are not identical or substantially identical to the backbone regions of pri-miRNAs encoded by a single naturally-occurring miRNA cluster, e.g., at least two of the plurality of shRNA-like molecules are derived from pri-miRNAs encoded by different naturally-occurring miRNA clusters. In an embodiment, the backbone region of at least one shRNA-like molecule is not repeated among the plurality of shRNA-like molecules, and the backbone regions of the plurality of shRNA-like molecules are not identical or substantially identical to the backbone regions of pri-miRNAs encoded by a single naturally-occurring miRNA duster.

In an embodiment, the plurality of shRNA-like molecules comprise two or more (e.g., 3, 4, 5, 6, 7, 8, 9, 10, 11, 12, 13, 14, 15, 16, 17, 18, 19, 20, or more) shRNA-like molecules. In another embodiment, the plurality of shRNA-like molecules comprise four or more (e.g., 5, 6, 7, 8, 9, 10, 11, 12, 13, 14, 15, 16, 17, 18, 19, 20, or more) shRNA-like molecules. In yet another embodiment, the plurality of shRNA-like molecules comprise seven or more (e.g., 8, 9, 10, 11, 12, 13, 14, 15, 16, 17, 18, 19, 20, or more) shRNA-like molecules. In still another embodiment, the plurality of shRNA-like molecules comprise ten or more (e.g., 11, 12, 13, 14, 15, 16, 17, 18, 19, 20, or more) shRNA-like molecules.

In an embodiment, the shRNA cluster is an artificial miRNA cluster, e.g., an artificial miRNA cluster described herein. In an embodiment, the shRNA duster encodes one or more (e.g., 2, 3, 4, 5, 6, 7, 8, 9, 10, or more) miRNA-based shRNA molecules (shRNA-miR molecules). In an embodiment, the shRNA cluster encodes one or more (e.g., 2, 3, 4, 5, 6, 7, 8, 9, 10, or more) shRNA molecules that are not derived from naturally-occurring pri-miRNAs.

In an embodiment, the shRNA cluster comprises a first nucleotide sequence encoding a first shRNA-like molecule and a second nucleotide sequence encoding a second shRNA-like molecule. In an embodiment, the first shRNA-like molecule is derived from a naturally-occurring pri-miRNA for a first miRNA (e.g., a naturally-occurring pri-miRNA that gives rise to or comprises a first miRNA). In another embodiment, the first shRNA-like molecule is not derived from a naturally-occurring pri-miRNA. In an embodiment, the second shRNA-like molecule is derived from a naturally-occurring pri-miRNA for a second miRNA (e.g., a naturally-occurring pri-miRNA that gives rise to or comprises a second miRNA). In another embodiment, the second shRNA-like molecule is not derived from a naturally-occurring pri-miRNA.

In an embodiment, the backbone region has one, two, or three of the following properties:

1) the terminal loop is about 3 to about 50 nucleotides, e.g., about 5 to about 40 nucleotides, about 8 to about 30 nucleotides, about 10 to about 20 nucleotides, or about 12 to about 18 nucleotides, in length;

2) the 5' flanking region is about 5 to about 300 nucleotides, e.g., about 10 to about 200 nucleotides, about 15 to about 150 nucleotides, about 20 to about 100 nucleotides, about 30 to about 50 nucleotides, or about 15 to about 30 nucleotides, e.g., about 15, 20, or 30 nucleotides, in length; or 3) the 3' flanking region is about 5 to about 300 nucleotides, e.g., about 10 to about 200 nucleotides, about 15 to about 150 nucleotides, about 20 to about 100 nucleotides, about 30 to about 50 nucleotides, or about 15 to about 30 nucleotides, e.g., about 15, 20, or 30 nucleotides, in length.

Without being bound by theory, it is believed that in an embodiment, the 5' flanking region and the 3' flanking region can form a duplex region, e.g., a partial duplex region. In an embodiment, the shRNA cluster further comprises a third nucleotide sequence encoding a third shRNA molecule. In an embodiment, the third shRNA-like molecule is derived from a naturally-occurring pri-miRNA for a third miRNA (e.g., a naturally-occurring pri-miRNA that gives rise to or comprises a third miRNA). In an embodiment, the third miRNA is naturally expressed from a transcript different than the transcript from which the first, second, or both miRNAs is expressed, e.g., not encoded by the same naturally-occurring miRNA duster as the first, second, or both miRNAs. In another embodiment, the third shRNA-like molecule is not derived from a naturally-occurring pri-miRNA.

In an embodiment, the shRNA cluster further comprises a fourth nucleotide sequence encoding a fourth shRNA molecule. In an embodiment, the fourth shRNA-like molecule is derived from a naturally-occurring pri-miRNA for a fourth miRNA (e.g., a naturally-occurring pri-miRNA that gives rise to or comprises a fourth miRNA). In an embodiment, the fourth miRNA is naturally expressed from a transcript different than the transcript from which the first, second, or third miRNA is expressed, e.g., not encoded by the same naturally-occurring miRNA cluster as the first, second, or third miRNA. In another embodiment, the fourth shRNA-like molecule is not derived from a naturally-occurring pri-miRNA.

In an embodiment, the shRNA cluster further comprises a fifth nucleotide sequence encoding a fifth shRNA molecule. In an embodiment, the fifth shRNA-like molecule is derived from a naturally-occurring pri-miRNA for a fifth miRNA (e.g., a naturally-occurring pri-miRNA that gives rise to or comprises a fifth miRNA). In an embodiment, the fifth miRNA is naturally expressed from a transcript different than the transcript from which the first, second, third, or fourth miRNA is expressed, e.g., not encoded by the same naturally-occurring miRNA cluster as the first, second, third, or fourth miRNA. In another embodiment, the fifth shRNA-like molecule is not derived from a naturally-occurring pri-miRNA.

In an embodiment, the shRNA cluster further comprises a sixth nucleotide sequence encoding a sixth shRNA molecule. In an embodiment, the sixth shRNA-like molecule is derived from a naturally-occurring pri-miRNA for a sixth miRNA (e.g., a naturally-occurring pri-miRNA that gives rise to or comprises a sixth miRNA). In an embodiment, the sixth miRNA is naturally expressed from a transcript different than the transcript from which the first, second, third, fourth, or fifth miRNA is expressed, e.g., not encoded by the same naturally-occurring miRNA cluster as the first, second, third, fourth, or fifth miRNA. In another embodiment, the sixth shRNA-like molecule is not derived from a naturally-occurring pri-miRNA.

In an embodiment, the shRNA cluster further comprises a seventh nucleotide sequence encoding a seventh shRNA molecule. In an embodiment, the seventh shRNA-like molecule is derived from a naturally-occurring pri-miRNA for a seventh miRNA (e.g., a naturally-occurring pri-miRNA that gives rise to or comprises a seventh miRNA). In an embodiment, the seventh miRNA is naturally expressed from a transcript different than the transcript from which the first, second, third, fourth, fifth, or sixth miRNA is expressed, e.g., not encoded by the same naturally-occurring miRNA cluster as the first, second, third, fourth, fifth, or sixth miRNA. In another embodiment, the seventh shRNA-like molecule is not derived from a naturally-occurring pri-miRNA.

In an embodiment, the shRNA cluster further comprises an $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ nucleotide sequence encoding an $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ shRNA-like molecule. In an embodiment, the $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ shRNA-like molecule is derived from a naturally-occurring pri-miRNA for an $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ miRNA (e.g., a naturally-occurring pri-miRNA that gives rise to or comprises an $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ miRNA). In an embodiment, the $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ shRNA-like molecule is not derived from a naturally-occurring pri-miRNA.

In an embodiment, the shRNA duster has one, two, or all of the following properties:

1) the terminal loop region is substantially homologous to (e.g., at least 50%, 60%, 70%, 80%, 90%, or 100% identical to, or differs by no more than 1, 2, 3, 4, 5, 6, 7, 8, 9, or 10 nucleotides from) a terminal loop region of a naturally-occurring pri-miRNA;

2) the 5' flanking region that is substantially homologous to (e.g., at least 50%, 60%, 70%, 80%, 90%, or 100% identical to, or differs by no more than 1, 2, 3, 4, 5, 6, 7, 8, 9, or 10 nucleotides from) a 5' flanking region of a naturally-occurring pri-miRNA molecule; or 3) the 3' flanking region that is substantially homologous to (e.g., at least 50%, 60%, 70%, 80%, 90%, or 100% identical to, or differs by no more than 1, 2, 3, 4, 5, 6, 7, 8, 9, or 10 nucleotides from) a 3' flanking region of a naturally-occurring pri-miRNA.

In an embodiment, the shRNA cluster encodes a plurality (e.g., 2, 3, 4, 5, 6, 7, 8, 9, 10, 11, 12, 13, 14, 15, 16, 17, 18, 19, 20, or more) of artificial RNA molecules, e.g., produced by the plurality of shRNA-like molecules. In an embodiment, the artificial RNA molecule is an RNAi molecule. In an embodiment, the artificial RNA molecule is an siRNA.

In an embodiment, the artificial RNA molecule does not comprise a naturally-occurring miRNA.

In an embodiment, the artificial RNA molecules produced by (e.g., processed from) the first and second shRNA-like molecules, target different mRNAs, e.g., mRNAs transcribed from different genes.

In an embodiment, each of the artificial RNA molecules produced by (e.g., processed from) the plurality (e.g., 2, 3, 4, 5, 6, 7, 8, 9, 10, 11, 12, 13, 14, 15, 16, 17, 18, 19, 20, or more) of shRNA-like molecules, targets a different mRNA, e.g., mRNAs transcribed from different genes. In an embodiment, at least two (e.g., 2, 3, 4, 5, or more) of the artificial RNA molecules produced by (e.g., processed from) the plurality (e.g., 3, 4, 5, 6, 7, 8, 9, 10, 11, 12, 13, 14, 15, 16, 17, 18, 19, 20, or more) of shRNA-like molecules, target the same mRNA or different mRNAs transcribed from a same gene.

In an embodiment, the artificial RNA molecule, when expressed in a cell, substantially inhibits expression (e.g., reduces the expression level) of the target mRNA (e.g., by cleavage of the target mRNA, inhibiting translation of the target mRNA, or both). In an embodiment, the cell is a T cell, e.g., CD4+ T cell, a stem cell, e.g., a hematopoietic stem cell, or a CD34+ cell. In an embodiment, the cell is a resting T cell. In another embodiment, the cell is an activated T cell. In an embodiment, the cell is a peripheral blood mononuclear cell (PBMC) or is isolated from PBMCs.

In an embodiment, the mRNA is encoded by a mammalian (e.g., human) gene, e.g., a gene encoding a receptor or co-receptor for a virus, e.g., an HIV co-receptor, e.g., CCR5 or CXCR4. In an embodiment, the target mRNA is encoded by a viral gene, e.g., an HIV gene (e.g., HIV-1 gene), e.g., Gag, Env, Tat, Pol2, Pol1, or Vif.

In an embodiment, the plurality of artificial RNA molecules, when expressed in a cell, substantially inhibit the expression of one or more (e.g., 2, 3, 4, 5, 6, 7, 8, 9, 10, or more) viral genes, e.g., one or more (e.g., 2, 3, 4, 5, or all) HIV genes chosen from Gag, Env, Tat, Pol2, Pol1, or Vif. In an embodiment, the plurality of artificial RNA molecules, when expressed in a cell, substantially inhibit the expression of HIV Gag, Env, Tat, Pol2, Pol1, and Vif genes.

In an embodiment, the guide strand is substantially complementary (e.g., at least 80%, 85%, 90%, 95% or 100% complementary) to a sequence in a target mRNA encoded by a mammalian gene, e.g., a human gene. In an embodiment, the guide strand is substantially complementary (e.g., at least 80%, 85%, 90%, 95%, or 100% complementary) to a sequence in a target mRNA encoded by a viral gene, e.g., an HIV gene.

In an embodiment, the shRNA cluster encodes one or more (e.g., 2, 3, 4, 5, 6, 7, 8, 9, 10, or more) artificial RNA molecules, each comprising a guide strand that is substantially complementary (e.g., at least 80%, 85%, 90%, 95%, or 100% complementary) to a sequence in a target mRNA encoded by a mammalian gene, e.g., a human gene; and one or more (e.g., 2, 3, 4, 5, 6, 7, 8, 9, 10, or more) artificial RNA molecules, each comprising a guide strand that is substantially complementary (e.g., at least 80%, 85%, 90%, 95%, or 100% complementary) to a sequence in a target mRNA encoded by a viral gene, e.g., an HIV gene.

In another embodiment, the shRNA cluster encodes one or more (e.g., 2, 3, 4, 5, 6, 7, 8, 9, 10, or more) artificial RNA molecules, each comprising a guide strand that is substantially complementary (e.g., at least 80%, 85%, 90%, 95%, or 100% complementary) to a sequence in a target mRNA encoded by a mammalian gene, e.g., a human gene; and four or more (e.g., 5, 6, 7, 8, 9, 10, or more) artificial RNA molecules, each comprising a guide strand that is substantially complementary (e.g., at least 80%, 85%, 90%, 95%, or 100% complementary) to a sequence in a target mRNA encoded by a viral gene, e.g., an HIV gene.

In yet another embodiment, the shRNA cluster encodes one artificial RNA molecule comprising a guide strand that is substantially complementary (e.g., at least 80%, 85%, 90%, 95%, or 100% complementary) to a sequence in a target mRNA encoded by a mammalian gene, e.g., a human gene, and six artificial RNA molecules, each comprising a guide strand that is substantially complementary (e.g., at least 80%, 85%, 90%, 95%, or 100% complementary) to a sequence in a target mRNA encoded by a viral gene, e.g., an HIV gene.

In an embodiment, the passenger strand is substantially identical (e.g., at least 80%, 85%, 90%, 95%, or 100% identical) to a sequence in a target mRNA encoded by a mammalian gene, e.g., a human gene.

In an embodiment, the passenger strand is substantially identical (e.g., at least 80%, 85%, 90%, 95%, or 100% identical) to a sequence in a target mRNA encoded by a viral gene, e.g., an HIV gene.

In an embodiment, the shRNA cluster encodes one or more (e.g., 2, 3, 4, 5, 6, 7, 8, 9, 10, or more) artificial RNA molecules, each comprising a passenger strand that is substantially identical (e.g., at least 80%, 85%, 90%, 95%, or 100% identical) to a sequence in a target mRNA encoded by a mammalian gene, e.g., a human gene; and one or more (e.g., 2, 3, 4, 5, 6, 7, 8, 9, 10, or more) artificial RNA molecules, each comprising a passenger strand that is substantially identical (e.g., at least 80%, 85%, 90%, 95%, or 100% identical) to a sequence in a target mRNA encoded by a viral gene, e.g., an HIV gene.

In another embodiment, the shRNA cluster encodes one or more (e.g., 2, 3, 4, 5, 6, 7, 8, 9, 10, or more) artificial RNA molecules, each comprising a passenger strand that is substantially identical (e.g., at least 80%, 85%, 90%, 95%, or 100% identical) to a sequence in a target mRNA encoded by a mammalian gene, e.g., a human gene; and four or more (e.g., 5, 6, 7, 8, 9, 10, or more) artificial RNA molecules, each comprising a passenger strand that is substantially identical (e.g., at least 80%, 85%, 90%, 95%, or 100% identical) to a sequence in a target mRNA encoded by a viral gene, e.g., an HIV gene.

In yet another embodiment, the shRNA cluster encodes one artificial RNA molecule comprising a passenger strand that is substantially identical (e.g., at least 80%, 85%, 90%, 95%, or 100% identical) to a sequence in a target mRNA encoded by a mammalian gene, e.g., a human gene, and six artificial RNA molecules each comprising a guide strand that is substantially identical (e.g., at least 80%, 85%, 90%, 95%, or 100% identical) to a sequence in a target mRNA encoded by a viral gene, e.g., an HIV gene.

In an embodiment, the virus is an RNA virus. In an embodiment, the virus is a fast-evolving virus. In an embodiment, the viral gene is from an RNA virus. In an embodiment, the virus is from a fast-evolving virus.

In an embodiment, the shRNA-like molecule is derived from a pri-miRNA for an miRNA described herein, e.g., miR-30a, miR-21, miR-20a, miR-16-1, miR-122, miR-185, or miR-150. In an embodiment, the plurality of shRNA-like molecules are derived from two or more (e.g., three, four, five, six, or all) pri-miRNAs for miR-30a, miR-21, miR-20a, miR-16-1, miR-122, miR-185, or miR-150. In an embodiment, the plurality of shRNA-like molecules are derived from pri-miRNAs for miR-30a, miR-21, miR-20a, miR-16-1, miR-122, miR-185, and miR-150.

In an embodiment, the terminal loop region is substantially homologous to (e.g., at least 50%, 60%, 70%, 80%, 90%, or 100% identical to, or differs by no more than 1, 2, 3, 4, 5, 6, 7, 8, 9, or 10 nucleotides from) a terminal loop region of a pri-miRNA for miR-30a, miR-21, miR-20a, miR-16-1, miR-122, miR-185, or miR-150.

In an embodiment, the 5' flanking region is substantially homologous to (e.g., at least 50%, 60%, 70%, 80%, 90%, or 100% identical to, or differs by no more than 1, 2, 3, 4, 5, 6, 7, 8, 9, or 10 nucleotides from) a 5' flanking of a pri-miRNA for miR-30a, miR-21, miR-20a, miR-16-1, miR-122, miR-185, or miR-150.

In an embodiment, the 3' flanking region is substantially homologous to (e.g., at least 50%, 60%, 70%, 80%, 90%, or 100% identical to, or differs by no more than 1, 2, 3, 4, 5, 6, 7, 8, 9, or 10 nucleotides from) a 3' flanking region of a pri-miRNA for miR-30a, miR-21, miR-20a, miR-16-1, miR-122, miR-185, or miR-150.

In an embodiment, the shRNA cluster comprises one or more (e.g., 2, 3, 4, 5, 6, or 7) nucleotide sequences, each of which is substantially homologous to (e.g., at least 50%, 60%, 70%, 80%, 90%, or 100% identical to, or differs by no more than 1, 2, 3, 4, 5, 6, 7, 8, 9, or 10 nucleotides from) a nucleotide sequence of a modified pri-miRNA-like molecule disclosed in Tables 4-5. In an embodiment, the shRNA cluster comprises the nucleotide sequence(s) of one or more (e.g., 2, 3, 4, 5, 6, or 7) of the modified pri-miRNA-like molecules disclosed in Tables 4-5. In an embodiment, the shRNA cluster comprises the nucleotide sequences of the seven modified pri-miRNA-like molecule disclosed in Tables 4-5.

In an embodiment, the shRNA cluster comprises one or more (e.g., 2, 3, 4, 5, 6, or 7) nucleotide sequences, each of which is substantially homologous to (e.g., at least 50%, 60%, 70%, 80%, 90%, or 100% identical to, or differs by no more than 1, 2, 3, 4, 5, 6, 7, 8, 9, or 10 nucleotides from) a guide strand nucleotide sequence disclosed in Tables 4-5.

In an embodiment, the shRNA cluster comprises one or more (e.g., 2, 3, 4, 5, 6, or 7) guide strand nucleotide sequences disclosed in Tables 4-5.

In an embodiment, the shRNA cluster comprises the seven guide strand nucleotide sequences disclosed in Tables 4-5.

In an embodiment, the shRNA cluster comprises one or more (e.g., 2, 3, 4, 5, 6, or 7) nucleotide sequences, each of which is substantially homologous to (e.g., at least 50%, 60%, 70%, 80%, 90%, or 100% identical to, or differs by no more than 1, 2, 3, 4, 5, 6, 7, 8, 9, or 10 nucleotides from) a passenger strand nucleotide sequence disclosed in Tables 4-5.

In an embodiment, the shRNA cluster comprises one or more (e.g., 2, 3, 4, 5, 6, or 7) passenger strand nucleotide sequences disclosed in Tables 4-5. In an embodiment, the shRNA cluster comprises the seven passenger strand nucleotide sequences disclosed in Tables 4-5.

In an embodiment, the shRNA cluster comprises one or more (e.g., 2, 3, 4, 5, 6, or 7) nucleotide sequences, each of which is substantially homologous to (e.g., at least 50%, 60%, 70%, 80%, 90%, or 100% identical to, or differs by no more than 1, 2, 3, 4, 5, 6, 7, 8, 9, or 10 nucleotides from) a terminal loop region, 5' flanking region, or 3' flanking region nucleotide sequence disclosed in Tables 4-5.

In an embodiment, the shRNA cluster comprises one or more (e.g., 2, 3, 4, 5, 6, or 7) terminal loop region, 5' flanking region, or 3' flanking region nucleotide sequences disclosed in Tables 4-5. In an embodiment, the shRNA cluster comprises the seven terminal loop region, 5' flanking region, or 3' flanking region nucleotide sequences disclosed in Tables 4-5.

In an embodiment, the shRNA cluster further comprises a plurality of spacer sequences (e.g., about 0 to about 250 nucleotides, about 1 to about 200 nucleotides, about 10 to about 150 nucleotides, about 20 to about 100 nucleotides, or about 30 to about 50 nucleotides, in length), wherein the spacer sequence is between the sequences encoding two shRNA-like molecules.

In an embodiment, the shRNA cluster is efficiently processed in the nucleus, e.g., by Drosha/DGCR8. In another embodiment, the shRNA cluster preserves the secondary structure of at least a portion of a native pri-miRNA, e.g., a pri-miRNA for miR-30a, miR-21, miR-20a, miR-16-1, miR-122, miR-185, or miR-150.

In an embodiment, the stem region does not include a bulge or a mismatch between the guide strand and the passenger strand. In another embodiment, the stem region comprises a bulge or a mismatch between the guide strand and the passenger strand.

In an embodiment, the guide strand is about 15 to about 30 nucleotides, e.g., about 18 to about 25 nucleotides or about 19 to about 21 nucleotides, in length. In another embodiment, the passenger strand is about 15 to about 30 nucleotides, e.g., about 18 to about 25 nucleotides or about 19 to about 21 nucleotides, in length.

In an embodiment, shRNA cluster is an expression cassette.

In an embodiment, the shRNA cluster further comprises a promoter, e.g., a Pol II promoter or a Pol III promoter, e.g., operably linked to an shRNA-like molecule (e.g., the plurality of shRNA-like molecules).

In an embodiment, the promoter is a constitutive promoter, an inducible promoter, a ubiquitous promoter, a tissue-specific promoter, a cell-type-specific promoter, and/or a developmental stage-specific promoter. In an embodiment, the promoter is an EF-1α-derived promoter. In another embodiment, the promoter is a CMV-derived promoter.

In an embodiment, the shRNA cluster further comprises one or more (e.g., two or three) selectable markers. In an embodiment, the shRNA cluster further comprises a reporter gene.

In an embodiment, the shRNA cluster further comprises a polyadenylation signal.

In an embodiment, the shRNA duster further comprises one or more (e.g., two) long terminal repeats (LTRs). In an embodiment, the shRNA duster further comprises an internal ribosome entry site (IRES).

In an embodiment, the shRNA cluster is in a viral vector, e.g., a retroviral or lentiviral vector, e.g., a self-inactivating (SIN) retroviral or lentiviral vector.

In one aspect, the disclosure features a nucleic acid molecule, e.g., an artificial miRNA cluster, encoding a plurality of modified pri-miRNA-like molecules, e.g., miRNA-based shRNA molecules (shRNA-miR molecules), the nucleic acid molecule comprising: a first nucleotide sequence encoding a first modified pri-miRNA-like molecule (e.g., shRNA-miR molecule) derived from a naturally-occurring pri-miRNA for a first miRNA (e.g., a naturally-occurring pri-miRNA that gives rise to or comprises a first miRNA); and a second nucleotide sequence encoding a second modified pri-miRNA-like molecule (e.g., shRNA-miR molecule) derived from a naturally-occurring pri-miRNA for a second miRNA (e.g., a naturally-occurring pri-miRNA that gives rise to or comprises a second miRNA), wherein the first and second miRNAs are naturally expressed from different transcripts or are not in the same naturally-occurring miRNA cluster.

In an embodiment, each of the plurality of modified pri-miRNA-like molecules (e.g., shRNA-miR molecules) comprises: a stem region comprising an artificial RNA molecule comprising a guide strand and a passenger strand, wherein the guide strand is substantially complementary to a target mRNA, a terminal loop region, a 5' flanking region, and a 3' flanking region.

In an embodiment, the modified pri-miRNA-like molecule (e.g., shRNA-miR molecule) has one or more (e.g., 2 or all) of the following:

1) a terminal loop region that is substantially homologous to (e.g., at least 50%, 60%, 70%, 80%, 90%, or 100% identical to, or differs by no more than 1, 2, 3, 4, 5, 6, 7, 8, 9, or 10 nucleotides from) a terminal loop region of a naturally-occurring pri-miRNA;

2) a 5' flanking region that is substantially homologous to (e.g., at least 50%, 60%, 70%, 80%, 90%, or 100% identical to, or differs by no more than 1, 2, 3, 4, 5, 6, 7, 8, 9, or 10 nucleotides from) a 5' flanking region of a naturally-occurring pri-miRNA; or 3) a 3' flanking region that is substantially homologous to (e.g., at least 50%, 60%, 70%, 80%, 90%, or 100% identical to, or differs by no more than 1, 2, 3, 4, 5, 6, 7, 8, 9, or 10 nucleotides from) a 3' flanking region of a naturally-occurring pri-miRNA.

In an embodiment, the terminal loop is about 3 to about 50 nucleotides, e.g., about 5 to about 40 nucleotides, about 8 to about 30 nucleotides, about 10 to about 20 nucleotides, or about 12 to about 18 nucleotides, in length.

In an embodiment, the 5' flanking region is about 5 to about 300 nucleotides, e.g., about 10 to about 200 nucleotides, about 15 to about 150 nucleotides, about 20 to about 100 nucleotides, about 30 to about 50 nucleotides, or about 15 to about 30 nucleotides, e.g., about 15, 20, or 30 nucleotides, in length.

In an embodiment, the 3' flanking region is about 5 to about 300 nucleotides, e.g., about 10 to about 200 nucleotides, about 15 to about 150 nucleotides, about 20 to about 100 nucleotides, about 30 to about 50 nucleotides, or about 15 to about 30 nucleotides, e.g., about 15, 20, or 30 nucleotides, in length.

Without being bound by theory, it is believed that in an embodiment, the 5' flanking region and the 3' flanking region can form a duplex region, e.g., a partial duplex region. In an embodiment, the nucleic acid molecule (e.g., artificial miRNA cluster) further comprises a third nucleotide sequence encoding a third modified pri-miRNA-like molecule derived from a naturally-occurring pri-miRNA for a third miRNA (e.g., a naturally-occurring pri-miRNA that gives rise to or comprises a third miRNA).

In an embodiment, the third miRNA is naturally expressed from a transcript different than the transcript from which the first, second, or both miRNAs is expressed, e.g., not in the same naturally-occurring miRNA cluster as the first, second, or both miRNAs.

In an embodiment, the nucleic acid molecule (e.g., artificial miRNA duster) further comprises a fourth nucleotide sequence encoding a fourth modified pri-miRNA-like molecule derived from a naturally-occurring pri-miRNA for a fourth miRNA (e.g., a naturally-occurring pri-miRNA that gives rise to or comprises a fourth miRNA).

In an embodiment, the fourth miRNA is naturally expressed from a transcript different than the transcript from which the first, second, or third miRNA is expressed, e.g., not in the same naturally-occurring miRNA cluster as the first, second, or third miRNA.

In an embodiment, the nucleic acid molecule (e.g., artificial miRNA duster) further comprises a fifth nucleotide sequence encoding a fifth modified pri-miRNA-like molecule derived from a naturally-occurring pri-miRNA for a fifth miRNA (e.g., a naturally-occurring pri-miRNA that gives rise to or comprises a fifth miRNA).

In an embodiment, the fifth miRNA is naturally expressed from a transcript different than the transcript from which the first, second, third, or fourth miRNA is expressed, e.g., not in the same naturally-occurring miRNA duster as the first, second, third, or fourth miRNA.

In an embodiment, the nucleic acid molecule (e.g., artificial miRNA duster) further comprises a sixth nucleotide sequence encoding a sixth modified pri-miRNA-like molecule derived from a naturally-occurring pri-miRNA for a sixth miRNA molecule (e.g., a naturally-occurring pri-miRNA that gives rise to or comprises a sixth miRNA).

In an embodiment, the sixth miRNA molecule is naturally expressed from a transcript different than the transcript from which the first, second, third, fourth, or fifth miRNA is expressed, e.g., not in the same naturally-occurring miRNA cluster as the first, second, third, fourth, or fifth miRNA.

In an embodiment, the nucleic acid molecule (e.g., artificial miRNA cluster) further comprises a seventh nucleotide sequence encoding a seventh modified pri-miRNA-like molecule derived from a naturally-occurring pri-miRNA for a seventh miRNA (e.g., a naturally-occurring pri-miRNA that gives rise to or comprises a seventh miRNA).

In an embodiment, the seventh miRNA is naturally expressed from a transcript different than the transcript from which the first, second, third, fourth, fifth, or sixth miRNA is expressed, e.g., not in the same naturally-occurring miRNA cluster as the first, second, third, fourth, fifth, or sixth miRNA.

In an embodiment, the nucleic acid molecule (e.g., artificial miRNA cluster) further comprises an $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ nucleotide sequence encoding an $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ modified pri-miRNA-like molecule derived from a naturally-occurring pri-miRNA for an $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ miRNA (e.g., a naturally-occurring pri-miRNA that gives rise to or comprises an $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ miRNA).

In an embodiment, the nucleic acid molecule (e.g., artificial miRNA cluster) encodes two or more (e.g., 3, 4, 5, 6, 7, 8, 9, 10, 11, 12, 13, 14, 15, 16, 17, 18, 19, 20, or more) modified pri-miRNA-like molecules derived from naturally-occurring pri-miRNAs. In an embodiment, at least two (e.g., 2, 3, 4, 5, or more) of the modified pri-miRNA-like molecules in the plurality (e.g., 3, 4, 5, 6, 7, 8, 9, 10, 11, 12, 13, 14, 15, 16, 17, 18, 19, 20, or more) are derived from the same naturally-occurring pri-miRNA. In an embodiment, each of the plurality (e.g., 2, 3, 4, 5, 6, 7, 8, 9, 10, 11, 12, 13, 14, 15, 16, 17, 18, 19, 20, or more) of the modified pri-miRNA-like molecules is derived from a different naturally-occurring pri-miRNA.

In an embodiment, the nucleic acid molecule (e.g., artificial miRNA cluster) encodes seven modified pri-miRNA-like molecules derived from naturally-occurring pri-miRNAs. In an embodiment, each of the seven modified pri-miRNA-like molecules is derived from a different naturally-occurring pri-miRNA. In an embodiment, the seven different naturally-occurring pri-miRNAs are not in the same miRNA cluster.

In an embodiment, the nucleic acid molecule (e.g., artificial miRNA cluster) further encodes at least one (e.g., 1, 2, 3, 4, 5, or more) shRNA molecule that is not derived from a naturally-occurring pri-miRNA.

In an embodiment, the nucleic acid molecule (e.g., artificial miRNA cluster) encodes a plurality (e.g., 2, 3, 4, 5, 6, 7, 8, 9, 10, 11, 12, 13, 14, 15, 16, 17, 18, 19, 20, or more) of artificial RNA molecules. In an embodiment, the artificial RNA molecule is an RNAi molecule. In an embodiment, the artificial RNA molecule is an siRNA. In an embodiment, the artificial RNA molecule does not comprise a naturally-occurring miRNA.

In an embodiment, the artificial RNA molecules produced by the first and second modified pri-miRNA-like molecules, target different mRNAs, e.g., mRNAs transcribed from different genes.

In an embodiment, each of the artificial RNA molecules encoded by the plurality (e.g., 2, 3, 4, 5, 6, 7, 8, 9, 10, 11, 12, 13, 14, 15, 16, 17, 18, 19, 20, or more) of modified pri-miRNA-like molecules, targets a different mRNA, e.g., mRNAs transcribed from different genes. In an embodiment, at least two (e.g., 2, 3, 4, 5, or more) of the artificial RNA molecules produced by (e.g., processed from) the plurality (e.g., 3, 4, 5, 6, 7, 8, 9, 10, 11, 12, 13, 14, 15, 16, 17, 18, 19, 20, or more) of modified pri-miRNA-like molecules, target a same mRNA or different mRNAs transcribed from the same gene.

In an embodiment, the artificial RNA molecule, when expressed in a cell, substantially inhibits expression (e.g., reduces the expression level) of the target mRNA (e.g., by cleavage of the target mRNA, inhibit translation of the target mRNA, or both). In an embodiment, the cell is a T cell, e.g., CD4+ T cell, a stem cell, e.g., a hematopoietic stem cell, or a CD34+ cell. In an embodiment, the cell is a resting T cell. In another embodiment, the cell is an activated T cell. In an embodiment, the cell is a peripheral blood mononuclear cell (PBMC) or is isolated from PBMCs.

In an embodiment, the mRNA is encoded by a mammalian (e.g., human) gene, e.g., a gene encoding a receptor or co-receptor for a virus, e.g., an HIV co-receptor, e.g., CCR5 or CXCR4. In an embodiment, the target mRNA is encoded by a viral gene, e.g., an HIV gene (e.g., HIV-1 gene), e.g., Gag, Env, Tat, Pol2, Pol1, or Vif.

In an embodiment, the plurality of artificial RNA molecules, when expressed in a cell, substantially inhibit the expression of one or more (e.g., 2, 3, 4, 5, 6, 7, 8, 9, 10, or more) viral genes, e.g., one or more (e.g., 2, 3, 4, 5, or all) HIV genes chosen from Gag, Env, Tat, Pol2, Pol1, or Vif. In an embodiment, the plurality of artificial RNA molecules, when expressed in a cell, substantially inhibit the expression of HIV Gag, Env, Tat, Pol2, Pol1, and Vif genes.

In an embodiment, the guide strand is substantially complementary (e.g., at least 80%, 85%, 90%, 95%, or 100% complementary) to a sequence in a target mRNA encoded by a mammalian gene, e.g., a human gene. In an embodiment, the guide strand is substantially complementary (e.g., at least 80%, 85%, 90%, 95%, or 100% complementary) to a sequence in a target mRNA encoded by a viral gene, e.g., an HIV gene.

In an embodiment, the nucleic acid molecule (e.g., artificial miRNA cluster) encodes one or more (e.g., 2, 3, 4, 5, 6, 7, 8, 9, 10, or more) artificial RNA molecules, each comprising a guide strand that is substantially complementary (e.g., at least 80%, 85%, 90%, 95%, or 100% complementary) to a sequence in a target mRNA encoded by a mammalian gene, e.g., a human gene; and one or more (e.g., 2, 3, 4, 5, 6, 7, 8, 9, 10, or more) artificial RNA molecules, each comprising a guide strand that is substantially complementary (e.g., at least 80%, 85%, 90%, 95%, or 100% complementary) to a sequence in a target mRNA encoded by a viral gene, e.g., an HIV gene.

In another embodiment, the nucleic acid molecule (e.g., artificial miRNA cluster) encodes one or more (e.g., 2, 3, 4, 5, 6, 7, 8, 9, 10, or more) artificial RNA molecules, each comprising a guide strand that is substantially complementary (e.g., at least 80%, 85%, 90%, 95%, or 100% complementary) to a sequence in a target mRNA encoded by a mammalian gene, e.g., a human gene; and four or more (e.g., 5, 6, 7, 8, 9, 10, or more) artificial RNA molecules, each comprising a guide strand that is substantially complementary (e.g., at least 80%, 85%, 90%, 95%, or 100% complementary) to a sequence in a target mRNA encoded by a viral gene, e.g., an HIV gene.

In yet another embodiment, the nucleic acid molecule (e.g., artificial miRNA cluster) encodes one artificial RNA molecule comprising a guide strand that is substantially complementary (e.g., at least 80%, 85%, 90%, 95%, or 100% complementary) to a sequence in a target mRNA encoded by a mammalian gene, e.g., a human gene, and six artificial RNA molecules, each comprising a guide strand that is substantially complementary (e.g., at least 80%, 85%, 90%, 95%, or 100% complementary) to a sequence in a target mRNA encoded by a viral gene, e.g., an HIV gene.

In an embodiment, the passenger strand is substantially identical (e.g., at least 80%, 85%, 90%, 95%, or 100% identical) to a sequence in a target mRNA encoded by a mammalian gene, e.g., a human gene.

In an embodiment, the passenger strand is substantially identical (e.g., at least 80%, 85%, 90%, 95%, or 100% identical) to a sequence in a target mRNA encoded by a viral gene, e.g., an HIV gene.

In an embodiment, the nucleic acid molecule (e.g., artificial miRNA cluster) encodes one or more (e.g., 2, 3, 4, 5, 6, 7, 8, 9, 10, or more) artificial RNA molecules, each comprising a passenger strand that is substantially identical (e.g., at least 80%, 85%, 90%, 95%, or 100% identical) to a sequence in a target mRNA encoded by a mammalian gene, e.g., a human gene; and one or more (e.g., 2, 3, 4, 5, 6, 7, 8, 9, 10, or more) artificial RNA molecules, each comprising a passenger strand that is substantially identical (e.g., at least 80%, 85%, 90%, 95%, or 100% identical) to a sequence in a target mRNA encoded by a viral gene, e.g., an HIV gene.

In another embodiment, the nucleic acid molecule (e.g., artificial miRNA cluster) encodes one or more (e.g., 2, 3, 4, 5, 6, 7, 8, 9, 10, or more) artificial RNA molecules, each comprising a passenger strand that is substantially identical (e.g., at least 80%, 85%, 90%, 95%, or 100% identical) to a sequence in a target mRNA encoded by a mammalian gene, e.g., a human gene; and four or more (e.g., 5, 6, 7, 8, 9, 10, or more) artificial RNA molecules, each comprising a passenger strand that is substantially identical (e.g., at least 80%, 85%, 90%, 95%, or 100% identical) to a sequence in a target mRNA encoded by a viral gene, e.g., an HIV gene.

In yet another embodiment, the nucleic acid molecule (e.g., artificial miRNA cluster) encodes one artificial RNA molecule comprising a passenger strand that is substantially identical (e.g., at least 80%, 85%, 90%, 95%, or 100% identical) to a sequence in a target mRNA encoded by a mammalian gene, e.g., a human gene, and six artificial RNA molecules each comprising a guide strand that is substantially identical (e.g., at least 80%, 85%, 90%, 95%, or 100% identical) to a sequence in a target mRNA encoded by a viral gene, e.g., an HIV gene.

In an embodiment, the virus is an RNA virus. In an embodiment, the virus is a fast-evolving virus. In an embodiment, the viral gene is from an RNA virus. In an embodiment, the virus is from a fast-evolving virus.

In an embodiment, the modified pri-miRNA-like molecule is derived from a pri-miRNA for an miRNA described herein, e.g., miR-30a, miR-21, miR-20a, miR-16-1, miR-122, miR-185, or miR-150. In an embodiment, the plurality of modified pri-miRNA-like molecules are derived from two or more (e.g., three, four, five, six, or all) pri-miRNAs for miR-30a, miR-21, miR-20a, miR-16-1, miR-122, miR-185, or miR-150. In an embodiment, the plurality of modified pri-miRNA-like molecules are derived from pri-miRNAs for miR-30a, miR-21, miR-20a, miR-16-1, miR-122, miR-185, and miR-150.

In an embodiment, the terminal loop region is substantially homologous to (e.g., at least 50%, 60%, 70%, 80%, 90%, or 100% identical to, or differs by no more than 1, 2, 3, 4, 5, 6, 7, 8, 9, or 10 nucleotides from) a terminal loop region of a pri-miRNA for miR-30a, miR-21, miR-20a, miR-16-1, miR-122, miR-185, or miR-150.

In an embodiment, the 5' flanking region is substantially homologous to (e.g., at least 50%, 60%, 70%, 80%, 90%, or 100% identical to, or differs by no more than 1, 2, 3, 4, 5, 6, 7, 8, 9, or 10 nucleotides from) a 5' flanking of a pri-miRNA for miR-30a, miR-21, miR-20a, miR-16-1, miR-122, miR-185, or miR-150.

In an embodiment, the 3' flanking region is substantially homologous to (e.g., at least 50%, 60%, 70%, 80%, 90%, or 100% identical to, or differs by no more than 1, 2, 3, 4, 5, 6, 7, 8, 9, or 10 nucleotides from) a 3' flanking region of a pri-miRNA for miR-30a, miR-21, miR-20a, miR-16-1, miR-122, miR-185, or miR-150.

In an embodiment, the nucleic acid molecule (e.g., artificial miRNA duster) comprises one or more (e.g., 2, 3, 4, 5, 6, or 7) nucleotide sequences, each of which is substantially homologous to (e.g., at least 50%, 60%, 70%, 80%, 90%, or 100% identical to, or differs by no more than 1, 2, 3, 4, 5, 6, 7, 8, 9, or 10 nucleotides from) a nucleotide sequence of a modified pri-miRNA-like molecule disclosed in Tables 4-5. In an embodiment, the nucleic acid molecule (e.g., artificial miRNA duster) comprises the nucleotide sequence (s) of one or more (e.g., 2, 3, 4, 5, 6, or 7) modified pri-miRNA-like molecules disclosed in Tables 4-5. In an embodiment, the nucleic acid molecule (e.g., artificial miRNA duster) comprises the nucleotide sequences of the seven modified pri-miRNA-like molecule disclosed in Tables 4-5.

In an embodiment, the nucleic acid molecule (e.g., artificial miRNA cluster) comprises one or more (e.g., 2, 3, 4, 5, 6, or 7) nucleotide sequences, each of which is substantially homologous to (e.g., at least 50%, 60%, 70%, 80%, 90%, or 100% identical to, or differs by no more than 1, 2, 3, 4, 5, 6, 7, 8, 9, or 10 nucleotides from) a guide strand nucleotide sequence disclosed in Tables 4-5. In an embodiment, the nucleic acid molecule (e.g., artificial miRNA cluster) comprises one or more (e.g., 2, 3, 4, 5, 6, or 7) guide strand nucleotide sequences disclosed in Tables 4-5. In an embodiment, the nucleic acid molecule (e.g., artificial miRNA cluster) comprises the seven guide strand nucleotide sequences disclosed in Tables 4-5.

In an embodiment, the nucleic acid molecule (e.g., artificial miRNA cluster) comprises one or more (e.g., 2, 3, 4, 5, 6, or 7) nucleotide sequences, each of which is substantially homologous to (e.g., at least 50%, 60%, 70%, 80%, 90%, or 100% identical to, or differs by no more than 1, 2, 3, 4, 5, 6, 7, 8, 9, or 10 nucleotides from) a passenger strand nucleotide sequence disclosed in Tables 4-5. In an embodiment, the nucleic acid molecule (e.g., artificial miRNA cluster) comprises one or more (e.g., 2, 3, 4, 5, 6, or 7) passenger strand nucleotide sequences disclosed in Tables 4-5. In an embodiment, the nucleic acid molecule (e.g., artificial miRNA cluster) comprises the seven passenger strand nucleotide sequences disclosed in Tables 4-5.

In an embodiment, the nucleic acid molecule (e.g., artificial miRNA cluster) comprises one or more (e.g., 2, 3, 4, 5, 6, or 7) nucleotide sequences, each of which is substantially homologous to (e.g., at least 50%, 60%, 70%, 80%, 90%, or 100% identical to, or differs by no more than 1, 2, 3, 4, 5, 6, 7, 8, 9, or 10 nucleotides from) a terminal loop region, 5' flanking region, or 3' flanking region nucleotide sequence disclosed in Tables 4-5.

In an embodiment, the nucleic acid molecule (e.g., artificial miRNA cluster) comprises one or more (e.g., 2, 3, 4, 5, 6, or 7) terminal loop region, 5' flanking region, or 3' flanking region nucleotide sequences disclosed in Tables 4-5. In an embodiment, the nucleic acid molecule (e.g., artificial miRNA cluster) comprises the seven terminal loop region, 5' flanking region, or 3' flanking region nucleotide sequences disclosed in Tables 4-5.

In an embodiment, the nucleic acid molecule (e.g., artificial miRNA cluster) further comprises a plurality of spacer sequences (e.g., about 0 to about 250 nucleotides, about 1 to about 200 nucleotides, about 10 to about 150 nucleotides, about 20 to about 100 nucleotides, or about 30 to about 50 nucleotides, in length), wherein the spacer sequence is between the sequences encoding two modified pri-miRNA-like molecules.

In an embodiment, the nucleic acid molecule (e.g., artificial miRNA cluster) is efficiently processed in the nucleus, e.g., by Drosha/DGCR8. In another embodiment, the nucleic acid molecule (e.g., artificial miRNA cluster) preserves the secondary structure of at least a portion of a naturally-occurring pri-miRNA, e.g., a pri-miRNA for miR-30a, miR-21, miR-20a, miR-16-1, miR-122, miR-185, or miR-150.

In an embodiment, the stem region does not include a bulge or a mismatch between the guide strand and the passenger strand. In another embodiment, the stem region comprises a bulge or a mismatch between the guide strand and the passenger strand.

In an embodiment, the guide strand is about 15 to about 30 nucleotides, e.g., about 18 to about 25 nucleotides or about 19 to about 21 nucleotides, in length. In another embodiment, the passenger strand is about 15 to about 30 nucleotides, e.g., about 18 to about 25 nucleotides or about 19 to about 21 nucleotides, in length.

In an embodiment, the nucleic acid molecule (e.g., artificial miRNA cluster) is an expression cassette. In an embodiment, the nucleic acid molecule (e.g., artificial miRNA cluster) further comprises a promoter, e.g., a Pol II promoter or a Pol III promoter, e.g., operably linked to a modified pri-miRNA-like molecule (e.g., the plurality of modified pri-miRNA-like molecules).

In an embodiment, the promoter is a constitutive promoter, an inducible promoter, a ubiquitous promoter, a tissue-specific promoter, a cell-type-specific promoter, and/or a developmental stage-specific promoter. In an embodiment, the promoter is an EF-1α-derived promoter. In another embodiment, the promoter is a CMV-derived promoter.

In an embodiment, the nucleic acid molecule (e.g., artificial miRNA duster) further comprises one or more (e.g., two or three) selectable markers. In an embodiment, the nucleic acid molecule (e.g., artificial miRNA cluster) further comprises a reporter gene. In an embodiment, the nucleic acid molecule (e.g., artificial miRNA cluster) further comprises a polyadenylation signal. In an embodiment, the nucleic acid molecule (e.g., artificial miRNA duster) further comprises one or more (e.g., two) long terminal repeats (LTRs). In an embodiment, the nucleic acid molecule (e.g., artificial miRNA cluster) further comprises an internal ribosome entry site (IRES).

In an embodiment, the nucleic acid molecule (e.g., artificial miRNA cluster) is in a viral vector, e.g., a retroviral or lentiviral vector, e.g., a self-inactivating (SIN) retroviral or lentiviral vector.

In another aspect, the disclosure features a nucleic acid molecule (e.g., artificial miRNA cluster) encoding seven modified pri-miRNA-like molecules (e.g., shRNA-miR molecules), the nucleic acid molecule comprising: a first nucleotide sequence encoding a first modified pri-miRNA-like molecule derived from a naturally-occurring pri-miRNA that gives rise to miR-30a, a second nucleotide sequence encoding a second modified pri-miRNA-like molecule derived from a naturally occurring pri-miRNA that gives rise to miR-21, a third nucleotide sequence encoding a third modified pri-miRNA-like molecule derived from a naturally-occurring pri-miRNA that gives rise to miR-20a, a fourth nucleotide sequence encoding a fourth modified pri-miRNA-like molecule derived from a naturally occurring pri-miRNA that gives rise to miR-16-1, a fifth nucleotide sequence encoding a fifth modified pri-miRNA-like molecule derived from a naturally occurring pri-miRNA that gives rise to miR-122, a sixth nucleotide sequence encoding a sixth modified pri-miRNA-like molecule derived from a naturally-occurring pri-miRNA that gives rise to miR-185, a seventh nucleotide sequence encoding a seventh modified pri-miRNA-like molecule derived from a naturally occurring pri-miRNA that gives rise to miR-150, wherein each of the seven modified pri-miRNA-like molecules comprises: a stem region comprising an artificial RNA molecule comprising a guide strand and a passenger strand, wherein the guide strand is substantially complementary to a target mRNA encoded by a gene selected from a group consisting of human CCR5 gene and HIV (e.g., HIV-1) Gag, Env, Tat, Pol2, Pol1, and Vif genes; a terminal loop region, e.g., a terminal loop region described herein; a 5' flanking region, e.g., a 5' flanking region described herein; and a 3' flanking region, e.g., a 3' flanking region described herein.

In an aspect, the disclosure features a transcript, e.g., a primary RNA transcript or a processed RNA transcript, encoded by a nucleic acid molecule (e.g., shRNA cluster or artificial miRNA cluster) described herein.

In an aspect, the disclosure features a plurality of shRNA-like molecules encoded by a nucleic acid molecule (e.g., shRNA cluster) described herein.

In another aspect, the disclosure features a plurality of modified pri-miRNA-like molecules (e.g., shRNA-miR molecules) encoded by a nucleic acid molecule (e.g., artificial miRNA cluster) described herein.

In yet another aspect, the disclosure features a plurality of artificial RNA molecules encoded by a nucleic acid molecule (e.g., shRNA cluster or artificial miRNA duster) described herein.

In an aspect, the disclosure features a cell comprising a nucleic acid molecule (e.g., shRNA cluster or artificial miRNA cluster) described herein.

In an embodiment, the cell is infected by a virus, e.g., an RNA virus, e.g., an HIV (e.g., HIV-1). In an embodiment, the virus is a fast-evolving virus. In an embodiment, the cell is isolated or derived from a patient, e.g., a patient having an HIV (e.g., HIV-1) infection or AIDS.

In another aspect, the disclosure features a cell comprising a plurality of shRNA-like molecules described herein or a plurality of modified pri-miRNA-like molecules described herein.

In an embodiment, the cell is infected by a virus, e.g., an RNA virus, e.g., an HIV (e.g., HIV-1). In an embodiment, the virus is a fast-evolving virus. In an embodiment, the cell is isolated or derived from a patient, e.g., a patient having an HIV (e.g., HIV-1) infection or AIDS.

In an aspect, the disclosure features a viral particle comprising a nucleic acid molecule (e.g., shRNA cluster or artificial miRNA cluster) described herein.

In an embodiment, the viral particle is a retrovirus or a lentivirus.

In another aspect, the disclosure features a viral particle comprising a plurality of shRNA-like molecules described herein or modified pri-miRNA-like molecules described herein.

In an embodiment, the viral particle is a retrovirus or a lentivirus.

In yet another aspect, the disclosure features a viral particle comprising a plurality of artificial RNA molecules (e.g., RNAi molecules) described herein.

In an embodiment, the viral particle is a retrovirus or a lentivirus.

In an aspect, the disclosure features a method for inhibiting the expression of a gene (e.g., a gene described herein) in a cell (e.g., a cell described herein), the method comprising contacting a cell with a nucleic acid molecule (e.g., shRNA cluster or artificial miRNA cluster) described herein, under conditions that allow expression of artificial RNA molecules, e.g., the artificial RNA molecules described herein.

In an embodiment, the cell is infected by a virus, e.g., an RNA virus, e.g., an HIV (e.g., HIV-1). In an embodiment, the virus is a fast-evolving virus. In an embodiment, the cell is isolated or derived from a patient, e.g., a patient having an HIV (e.g., HIV-1) infection or AIDS.

In an embodiment, the gene is a mammalian cellular gene, e.g., a gene encoding an HIV co-receptor, e.g., CCR5 or CXCR4. In an embodiment, the gene is a viral gene, e.g., an HIV (e.g., HIV-1) gene, e.g., Gag, Env, Tat, Pol2, Pol1, or Vif.

In an embodiment, the cell is contacted with the nucleic acid molecule (e.g., shRNA cluster or artificial miRNA cluster) in vivo. In an embodiment, the cell is contacted with the nucleic acid molecule (e.g., shRNA cluster or artificial miRNA cluster) ex vivo. In an embodiment, the cell is contacted with the nucleic acid molecule (e.g., shRNA cluster or artificial miRNA cluster) in vitro.

In another aspect, the disclosure features a method for inhibiting the expression of a gene (e.g., a gene described herein) in a cell (e.g., a cell described herein), the method comprising contacting a cell with a viral particle described herein, under conditions that allow expression of artificial RNA molecules, e.g., the artificial RNA molecules described herein.

In an embodiment, the cell is infected by a virus, e.g., an RNA virus, e.g., an HIV (e.g., HIV-1). In an embodiment, the virus is a fast-evolving virus. In an embodiment, the cell is isolated or derived from a patient, e.g., a patient having an HIV (e.g., HIV-1) infection or AIDS. In an embodiment, the gene is a mammalian cellular gene, e.g., a gene encoding an HIV co-receptor, e.g., CCR5 or CXCR4. In an embodiment, the gene is a viral gene, e.g., an HIV (e.g., HIV-1) gene, e.g., Gag, Env, Tat, Pol2, Pol1, or Vif.

In an embodiment, the cell is contacted with the nucleic acid molecule (e.g., shRNA cluster or artificial miRNA cluster) in vivo. In an embodiment, the cell is contacted with the nucleic acid molecule (e.g., shRNA cluster or artificial miRNA cluster) ex vivo. In an embodiment, the cell is contacted with the nucleic acid molecule (e.g., shRNA cluster or artificial miRNA cluster) in vitro.

In an aspect, the disclosure features a method for treating or preventing a disorder, e.g., an HIV (e.g., HIV-1) infection or AIDS, the method comprising administering a cell (e.g., a cell described herein) to a subject having an HIV infection or AIDS, or is at risk of having an HIV infection or AIDS, thereby treating or preventing the disorder, e.g., the HIV infection or AIDS.

In another aspect, the disclosure features a method for treating or preventing a disorder, e.g., an HIV (e.g., HIV-1) infection or AIDS, the method comprising: isolating a cell from a subject having an HIV infection or AIDS, or is at risk of having an HIV infection or AIDS; contacting the isolated cell with a viral particle described herein; and administering the cell contacted with the viral particle to the subject, thereby treating or preventing the disorder, e.g., the HIV infection or AIDS.

In yet another aspect, the disclosure features a method for treating or preventing a disorder, e.g., an HIV (e.g., HIV-1) infection or AIDS, the method comprising administering a nucleic acid molecule (e.g., shRNA cluster or artificial miRNA cluster) described herein to a subject having an HIV infection or AIDS, or at risk of having an HIV infection or AIDS, thereby treating or preventing the disorder, e.g., the HIV infection or AIDS.

In still another aspect, the disclosure features a method for treating or preventing a disorder, e.g., an HIV (e.g., HIV-1) infection or AIDS, the method comprising administering a viral particle described herein to a subject having an HIV infection or AIDS, or at risk of having an HIV infection or AIDS, thereby treating or preventing the disorder, e.g., the HIV infection or AIDS.

In an aspect, the disclosure features a cell described herein for use in treating or preventing an HIV infection or AIDS in a subject.

In another aspect, the disclosure features an shRNA cluster described herein or a nucleic acid molecule described herein for use in treating or preventing a disorder, e.g., an HIV infection or AIDS in a subject.

In yet another aspect, the disclosure features viral particle described herein for use in treating or preventing a disorder, e.g., an HIV infection or AIDS in a subject.

In an aspect, the disclosure features use of a cell described herein in the manufacture of a medicament for the treatment or prevention of a disorder, e.g., an HIV (e.g., HIV-1) infection or AIDS, in a subject.

In another aspect, the disclosure features use of a nucleic acid molecule (e.g., an shRNA cluster or artificial miRNA cluster) described herein in the manufacture of a medicament for the treatment or prevention of a disorder, e.g., an HIV (e.g., HIV-1) infection or AIDS, in a subject.

In yet another aspect, the disclosure features use of a viral particle described herein in the manufacture of a medicament for the treatment or prevention of a disorder, e.g., an HIV (e.g., HIV-1) infection or AIDS, in a subject.

In an aspect, the disclosure features a method for producing a cell that expresses a plurality of artificial RNA molecules described herein, the method comprising: contacting a cell (e.g., a cell described herein) with a nucleic acid molecule (e.g., shRNA cluster or artificial miRNA cluster) described herein, and optionally, culturing the cells under conditions that allow expression of the artificial RNA molecules, thereby producing the cell.

In an embodiment, the method comprises contacting the cell with a viral particle described herein. In an embodiment, the method further comprises isolating a cell from a subject, e.g., a subject having an HIV (e.g., HIV-1) infection or AIDS, prior to contacting the cell with the nucleic acid molecule.

In another aspect, the disclosure features a method for producing a cell that expresses a plurality of artificial RNA molecules (e.g., RNAi molecules) described herein, the method comprising: contacting a cell (e.g., a cell described herein) with a viral particle described herein, and optionally, culturing the cells under conditions that allow expression of the artificial RNA molecules, thereby producing the cell.

In an embodiment, the method further comprises isolating a cell from a subject, e.g., a subject having an HIV infection or AIDS, prior to contacting the cell with the nucleic acid molecule.

In an aspect, the disclosure features a method of designing a nucleic acid molecule (e.g., shRNA cluster or artificial miRNA cluster) described herein, the method comprising altering a backbone region of a naturally-occurring pri-miRNA, wherein the backbone region comprises a 5' flanking region, a terminal loop region, and a 3' flanking region.

In an embodiment, the method comprises one, two, or all of the following:

1) adding one or more (e.g., 2, 3, 4, 5, 6, 7, 8, 9, 10, 11, 12, 13, 14, 15, 16, 17, 18, 19, 20, or more) nucleotides in one, two, or all of the 5' flanking region, the terminal loop region, or the 3' flanking region;

2) deleting one or more (e.g., 2, 3, 4, 5, 6, 7, 8, 9, 10, 11, 12, 13, 14, 15, 16, 17, 18, 19, 20, or more) nucleotides in one, two, or all of the 5' flanking region, the terminal loop region, or the 3' flanking region; or 3) substituting one or more (e.g., 2, 3, 4, 5, 6, 7, 8, 9, 10, 11, 12, 13, 14, 15, 16, 17, 18, 19, 20, or more) nucleotides in one, two, or all of the 5' flanking region, the terminal loop region, or the 3' flanking region.

In an aspect, the disclosure features a composition, e.g., a pharmaceutical composition, comprising a nucleic acid molecule (e.g., an shRNA cluster or artificial miRNA cluster) described herein and a pharmaceutically acceptable carrier.

In another aspect, the disclosure features a composition, e.g., a pharmaceutical composition, comprising a cell described herein and a pharmaceutically acceptable carrier.

In yet another aspect, the disclosure features a composition, e.g., a pharmaceutical composition, comprising a viral particle described herein and a pharmaceutically acceptable carrier.

In an aspect, the disclosure features a kit comprising a nucleic acid molecule (e.g., shRNA cluster or artificial miRNA molecule) described herein and instructions for use of the nucleic acid molecule.

In another aspect, the disclosure features a kit comprising a cell described herein and instructions for use of the cell.

In yet another aspect, the disclosure features a kit comprising a viral particle described herein and instructions for use of the viral particle.

In an aspect, the disclosure features an artificial miRNA cluster to prevent infection of cells by HIV-1 comprising multiplexed miRNA-based shRNA. In an embodiment, said multiplexed miRNA-based shRNA comprises seven shRNAs. In another embodiment, the artificial miRNA cluster is also effective in controlling replication of cells infected with HIV-1.

In another aspect, the disclosure features a method of treatment for patients infected with HIV-1 comprising administering an effective amount of multiplexed miRNA-based shRNAs to a patient. In an embodiment, said multiplexed miRNA-based shRNA comprises seven shRNAs.

In yet another aspect, the disclosure features a method of preventing infection by HIV-1 comprising administering an effective amount of multiplexed miRNA-based shRNAs to a patient. In an embodiment, said multiplexed miRNA-based shRNA comprises seven shRNAs.

BRIEF DESCRIPTION OF THE FIGURES

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

(FIG. 1C) Schematic of single and multiplexed shRNA-miR designed to express indicated 1, 2, 4, and 7 shRNA-miRs. "X" represents restriction enzyme sites. (FIG. 1D) Schematic showing the position of shRNA-miR target sites in the HIV-1 genome.

(FIG. 2A) Plasmids encoding indicated individual or multiplexed shRNA-miRs (2 shRNA=CCR5 and Vif; 4 shRNAs=CCR5, Gag, Pol 1 and Vif; 7 shRNAs=CCR5, Gag, Env, Tat, Pol 1, Pol 2, and Vif) were co-transfected (10, 50, and 100 ng) with psiCHECK vector (100 ng) containing shRNA-miR target sequences in the 3' UTR of R-luc into 293 FT cells. Gene silencing was determined by dual luciferase assay performed 24 hours after co-transfection. The ratio of *renilla* luciferase (Rluc, reporter) to firefly luciferase (Fluc, internal control), normalized to the negative control mCherry vector expressing no shRNA-miR transfection is shown. The experiments were performed in triplicate. (FIG. 2B) Jurkat cells were transfected with single, dual, or multiple shRNA-miR encoding constructs and assayed for apoptosis by Annexin V staining. Staurosporine was used as positive control. (FIG. 2C) Indicated shRNAmiR expression vector-transduced PBMCs were subjected to MTS assay 2 and 4 days after transduction. Bar graphs represent mean+SD of triplicates.

(FIG. 3A) TZM-bl cells were transduced with lentivirus encoding CCR5 shRNA-miR only or multiplexed shRNA-miRs and CCR5 expression assayed 48 hours later by flow cytometry. (FIG. 3B) 293 T cells were co-transfected with pNL4-3 plasmid together with plasmids encoding no shRNA-miR (mock), CCR5 shRNA-miR only, or multiplexed shRNA-miRs. Supernatants collected 48 hours later were used to infect TZM-bl cells and after another 48 hours, cell lysates were analyzed for luciferase activity. (FIG. 3C) TZM-bl cells were transduced with HIV-1 env pseudotyped lentivirus encoding indicated shRNA-miRs and infected with HIV-$1_{NL4-3}$ (left) and HIV-$1_{BaL}$ (right) at an MOI of 0.01. p24 antigen level in culture supernatants obtained 9 days after infection was measured by ELISA.

(FIG. 4A) Activated and (FIG. 4B) resting T cells were transduced with HIV-1 env-pseudotyped lentivirus encoding no shRNA-miR (mock), CCR5 only shRNA-miR, or 7 shRNA-miRs (transduction efficiency in terms of GFP expression is shown below the schematic of treatment), infected with HIV-1NL4-3 (left panels) or HIV-1Bal (right panels) and p24 antigen levels in culture supernatants were measured by ELISA on days 0, 3, 9, and 15 after infection (top panels). Cells were analyzed by flow cytometry for GFP expression on days 0, 3, 9, and 15 after infection (bottom panels).

FIGS. 5A-5C illustrate inhibition of HIV-1 replication in HIV-seropositive donor PBMCs transduced with HIV-1 env pseudotyped lentiviral vector expressing multiplexed shRNA-miRs, in accordance with disclosed embodiment. (FIG. 5A) Time course of treatment and testing. (FIG. 5B) PBMCs from four different HIV-1 seropositive donors were transduced with HIV-1 env-pseudotyped lentivirus encoding no shRNA-miR (mock), Tat shRNA-miR, or 7 shRNA-miRs and p24 antigen level in culture supernatants measured by ELISA on indicated days after infection. (FIG. 5C (Seq ID No. 69, Seq ID No. 70, Seq ID No. 71, Seq ID No. 72))

Culture supernatants from Tat shRNA-miR transduced cells in FIG. 5B obtained on day 35 were sequenced for Tat shRNA-miR target region in the HIV-1 genome (FIG. 6A) Time course of treatment and analysis.

FIGS. 6B-6C NOD/SCID/IIL2-Ryc−/− mice were transplanted with PBMCs form two seropositive donors (FIG. 6B on ART) and (FIG. 6C treatment naive) that were transduced ex vivo with HIV-1 env-pseudotyped lentivirus encoding either no shRNA-miR (mock), only Tat shRNA-miR, or 7 shRNA-miRs and monitored for CD4 T cell counts on days 8, 29, and 43 and serum p24 levels on day 43. A representative dot plots of CD4 and CD8 T cell reconstitution on CD3 gated cells (left) and cumulative data from four mice on CD4 T cell levels (middle) and plasma p24 levels (right) is shown. P values between groups for p24 levels are indicated.

FIG. 13 is Table 1 entitled: Dominant small RNA reads in transfected cells;

FIG. 14 is Table 2 entitled: Oligonucleotide sequences used to insert target sites in the 3' UTR of R-luc in psiCheck2 vector;

FIG. 15 is Table 3 entitled: Sequences of the oligonucleotides used in the generation shRNAs.

DETAILED DESCRIPTION

Figure 1A:
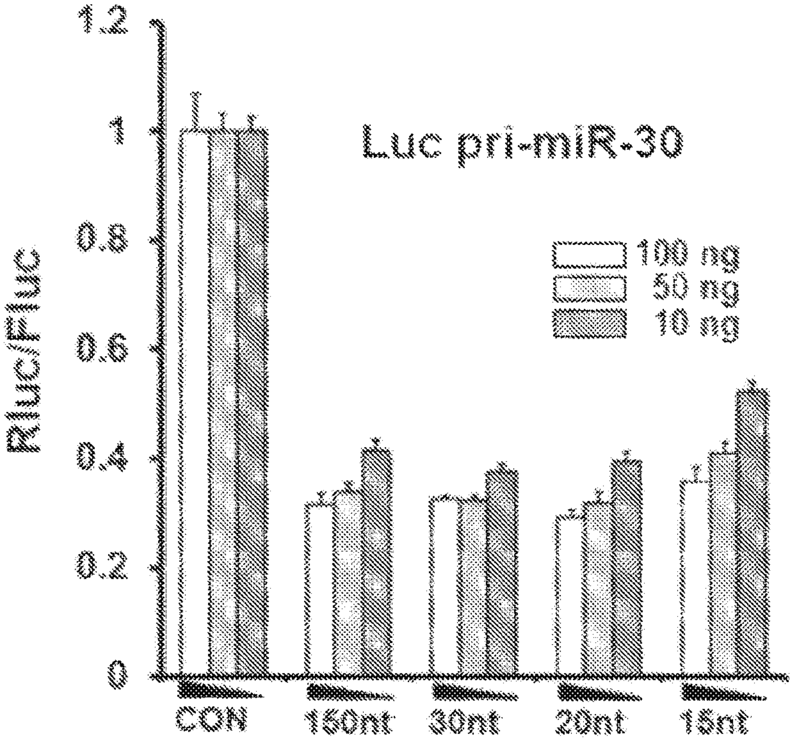
FIGS. 1A-1D illustrate optimized designs of multiplexed shRNA-miRs, in accordance with the disclosed embodiments. Plasmids encoding (FIG. 1A) pri-miR-30 or (FIG. 1B) pri-miR-150 containing indicated lengths of flanking sequence (10, 50, and 100 ng) were co-transfected with psiCHECK-2 vector (100 ng) harboring the target sequence in the 3' UTR of the *Renilla* luciferase gene and gene silencing was tested by dual luciferase assay 24 hours later. Bar graphs represent mean+SD of triplicates.

The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Unnecessary detail of known functions and operations may be omitted from the current description so as not to obscure the present invention and further discussion of the embodiments can be found in examples. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

As used herein, the articles "a" and "an" refer to one or to more than one (e.g., to at least one) of the grammatical object of the article.

As used herein, the term "or" is used herein to mean, and is used interchangeably with, the term "and/or", unless context clearly indicates otherwise.

As used herein, the term "about" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, the terms "nucleic acid", "nucleic acid sequence", "nucleotide sequence" or "polynucleotide sequence", and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide or a polynucleotide of genomic, cDNA, enzymatically processed, semisynthetic, or synthetic origin which either does not occur in nature or is linked to another polynucleotide in a non-natural arrangement.

As used herein, the term "gene" refers to a nucleic acid, e.g., a locus or region of DNA that encodes a function RNA (e.g., a coding or non-coding RNA, e.g., an mRNA or miRNA) or polypeptide. A gene can include both exon and (optionally) intron sequences. The nucleic acid can also optionally include non-coding sequences such as promoter and/or enhancer sequences.

As used herein, the term "mRNA" refers to a nucleic acid transcribed from a gene from which a polypeptide is translated, and may include non-translated regions such as a 5' UTR and/or a 3' UTR. It will be understood that shRNA-like molecules, modified pri-miRNA-like molecules (e.g., shRNA-miR molecules), or artificial RNA molecules (e.g., RNAi molecules) described herein may comprise a nucleotide sequence that is complementary to any sequence of an mRNA molecule, including translated regions, the 5' UTR, the 3' UTR, and sequences that include both a translated region and a portion of either 5' UTR or 3' UTR. An shRNA-like molecule, modified pri-miRNA-like molecule (e.g., shRNA-miR molecule), or artificial RNA molecule (e.g., RNAi molecule) described herein may comprise a nucleotide sequence that is complementary to a region of an mRNA molecule spanning the start codon or the stop codon.

As used herein, a sequence "encoding" a particular molecule is a nucleic acid that is transcribed (in the case of DNA) or translated (in the case of mRNA) into an RNA or polypeptide, in vitro or in vivo, when operably linked to an appropriate regulatory sequence.

As used herein, the term "operably linked" means that a sequence is linked to a regulatory sequence in a manner which allows expression of the sequence. Regulatory sequences include, e.g., promoters, enhancers, and other expression control elements that are art-recognized and are selected to direct expression of the sequence.

As used herein, the term "recombinant" refers to a material by recombinant DNA techniques, e.g., produced from cells transformed by an exogenous DNA construct encoding the desired RNA.

As used herein, the term "vector" refers to a vehicle for introducing a nucleic acid into a cell. Vectors include, but are not limited to, plasmids, phagemids, viruses, bacteria, and vehicles derived from viral or bacterial sources. Vectors can also include aptamers, where the aptamer either forms part of or is conjugated to the RNAi molecule (Dassie et al., Nature Biotechnology 27, 839-846 (2009), Thou and Rossi, Silence, 1:4 (2010). McNamera et al., Nature Biotechnology 24, 1005-1015 (2006)). As used herein, a "plasmid" is a circular, double-stranded DNA molecule. A useful type of vector for use in the present invention is a viral vector, wherein heterologous DNA sequences are inserted into a viral genome that can be modified to delete one or more viral genes or parts thereof. Certain vectors are capable of autonomous replication in a host cell (e.g., vectors having an origin of replication that functions in the host cell). Other vectors can be stably integrated into the genome of a host cell and are thereby replicated along with the host genome.

As used herein, the term "transfected cell" or "transduced cell" refers to a cell that has been genetically modified. Genetic modification can be stable or transient. Methods of transfection or transduction (i.e., introducing vectors or constructs into cells) include, but are not limited to, liposome fusion (transposomes), viral infection, and routine nucleic acid transfection methods such as electroporation, calcium phosphate precipitation, and microinjection. Successful transfection or transduction will have an intended effect in the transduced cell, such as gene expression, gene silencing, enhancing a gene target, or triggering target physiological event.

As used herein, the term "isolated" refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "derived from" means originating from or taken from a specified source. In the case of a sequence fragment, the term means that a partial (e.g., about 50% or more, about 60% or more, about 70% or more, about 75% or more, about 80% or more, about 85% or more, about 90% or more, about 95% or more, or about 99% or more) or complete sequence is present in the specified source and has been cloned or copied from the source.

As used herein, the term "synthetic" refers to a material prepared by chemical synthesis.

As used herein, the term "artificial" refers to a material that is not naturally occurring or differs from a material isolated from a natural source.

The compositions and methods disclosed herein encompass, at least in part, nucleic acids having the sequences specified, or sequences substantially identical or similar thereto, e.g., sequences at least 80%, 85%, 90%, 95% identical or higher to the sequence specified.

In the context of nucleotide sequence, the term "substantially homologous" or "substantially identical" is used herein to refer to a first nucleic acid sequence that contains a sufficient or minimum number of nucleotides that are identical to aligned nucleotides in a second nucleic acid sequence such that the first and second nucleotide sequences encode a nucleic acid or polypeptide having common functional activity, or encode a common structural nucleic acid or polypeptide domain or a common functional nucleic acid or polypeptide activity. For example, nucleotide sequences can have at least about 80%, 85%, 90%, 91%, 92%, 93%, 94%, 95%, 96%, 97%, 98%, or 99% identity to a reference sequence, e.g., a sequence provided herein.

Calculations of homology or sequence identity between sequences (the terms are used interchangeably herein) are performed as follows. To determine the percent identity of two nucleic acid sequences, the sequences are aligned for optimal comparison purposes (e.g., gaps can be introduced in one or both of a first and a second nucleic acid sequence for optimal alignment and non-homologous sequences can be disregarded for comparison purposes). In a typical embodiment, the length of a reference sequence aligned for comparison purposes is at least 30%, e.g., at least 40%, 50%, or 60%, e.g., at least 70%, 80%, 90%, or 100% of the length of the reference sequence. The nucleotides at corresponding nucleotide positions are then compared. When a position in the first sequence is occupied by the same nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch ((1970) J. Mol. Biol. 48:444-453) algorithm which has been incorporated into the GAP program in the GCG software package (available at www.gcg.com) using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package (available at www.gcg.com) using a NWSgapdna.CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5.

The percent identity between two nucleotide sequences can be determined using the algorithm of E. Meyers and W. Miller ((1989) CABIOS, 4:11-17) which has been incorporated into the ALIGN program (version 2.0) using a PAM120 weight residue table, a gap length penalty of 12, and a gap penalty of 4.

The nucleic acid sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to a nucleic acid as described herein. To obtain gapped alignments for comparison purposes, Gapped BLAST can be utilized as described in Altschul et al., (1997) Nucleic Acids Res. 25:3389-3402. When utilizing BLAST and gapped BLAST programs, the default parameters of the respective programs (e.g., NBLAST) can be used. See www.ncbi.nlm.nih.gov.

The compositions and methods disclosed herein also encompass, at least in part, nucleic acids having sequences substantially complementary or complementary to a reference sequence.

As used herein, the term "substantially complementary" refers to sequences of nucleotides where a majority (e.g., at least about 80%, 85%, 90%, 95%, 96%, 97%, 98%, or 99%) or all of the bases in the sequence are complementary, or one or more (e.g., no more than 20%, 15%, 10%, 5%, 4%, 3%, 2%, or 1%) bases are non-complementary, or mismatched. A complementary sequence can be a reverse complement of the sequence allowing for Watson-Crick base pairing, wobble base pairing, or both, whereby G pairs with either C or U, and A pairs with either U or T. A sequence may be complementary to the entire length of another sequence or it may be complementary to a specified portion or length of another sequence. One skilled in the art will recognize that the U may be present in RNA, and that T may be present in DNA. Therefore, a U within an RNA sequence may pair with A or G in either an RNA sequence or a DNA sequence, while an A within either of an RNA or DNA sequence may pair with a U in a RNA sequence or T in a DNA sequence. Two sequences that are substantially complementary may hybridize to each other, e.g., under low stringency, medium stringency, high stringency, or very high stringency conditions.

As used herein, the term "wobble base pairing" with regard to two complementary nucleic acid sequences refers to the base pairing of G to uracil U rather than C, when one or both of the nucleic acid strands contains the ribonucleobase U.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC. 1% SDS at 65° C. Very high stringency conditions 4) are suitable conditions and the ones that should be used unless otherwise specified.

As used herein, the term "treat," "treating", or "treatment" means that a subject (e.g., a human) who has a disorder and/or experiences a symptom of a disorder, will, in an embodiment, suffer a less severe symptom and/or recover faster when a therapeutic agent is administered than if the therapeutic agent were never administered. In an embodiment, when an HIV infection or AIDS is treated, an assay to detect HIV in the subject will detect fewer HIV after effective treatment for the HIV infection or AIDS. For example, a diagnostic assay, such as PCR (e.g., qPCR) will detect fewer or no HIV in a biological sample of a subject after administration of a therapeutic agent for the effective treatment of the HIV infection or AIDS. Treatment can, e.g., partially or completely alleviate, ameliorate, relieve, inhibit, or reduce the severity of and/or reduce incidence and optionally delay onset of one or more manifestations of the effects or symptoms, features, and/or causes of a particular infection, disease, disorder, and/or condition (e.g., an HIV infection). In an embodiment, treatment is of a subject who does not exhibit certain signs of the relevant infection, disease, disorder, and/or condition, and/or of a subject who exhibits only early signs of the infection, disease, disorder, and/or condition. In an embodiment, treatment is of a subject who exhibits one or more established signs of the relevant infection, disease, disorder, and/or condition. In an embodiment, treatment is of a subject diagnosed as suffering from an HIV infection or AIDS.

As used herein, the term "prevent," "preventing", or "prevention" means that a subject (e.g., a human) is less likely to have a disorder (e.g., an HIV infection or AIDS) if the subject receives a therapeutic agent, e.g., prior to (e.g., 1 day, 2 days, 1 week, 2 weeks, 3 weeks, or 1 month or more) being exposed to an agent that causes the disorder, e.g., HIV.

As used herein, a "subject" or "patient" can be a human or non-human animal.

Design of shRNA Clusters and Modified pri-miRNA Clusters

As used herein, an "shRNA cluster" refers to a group of nucleotide sequences encoding shRNA-like molecules located within a short distance (e.g., within about 10 Kb, e.g., within about 5 kb, 4 kb, 3 kb, 2 kb, or 1 kb) on a same nucleic acid. In an embodiment, expression of the shRNA-like molecules encoded by an shRNA cluster is under the control of a common regulatory sequence (e.g., a promoter). In an embodiment, the shRNA-like molecules are transcribed as a single transcript.

As used herein, an "miRNA cluster" refers to a group of nucleotide sequences encoding miRNA-like molecules located within a short distance (e.g., within about 10 Kb, e.g., within about 5 kb, 4 kb, 3 kb, 2 kb, or 1 kb) on a same nucleic acid, e.g., a same chromosome. In an embodiment, expression of the modified pri-miRNA-like molecules encoded by an miRNA cluster is under the control of a common regulatory sequence (e.g., a promoter). In an embodiment, the modified pri-miRNA-like molecules are transcribed as a single transcript.

Exemplary approaches to define and analyze miRNA clusters are described, e.g., in Chan et al. (2012) Genomics 100(3): 141-148, which is incorporated by reference herein in its entirety.

The nucleic acid molecules (e.g., shRNA clusters or artificial miRNA clusters) described herein can encode artificial RNA molecules, e.g., interfering RNA or small inhibitory RNA molecules (RNAi molecules). RNAi molecules include, but are not limited to, short interfering RNAs (siRNAs), repeat-associated siRNAs (rasiRNAs), and micro-RNAs (miRNAs) in all stages of processing. These molecules can have different origins: siRNAs can be synthetic or processed from double-stranded precursors (dsRNAs) with two distinct strands of base-paired RNA; siRNAs that are derived from repetitive sequences in the genome are called rasiRNAs; and miRNAs are derived from a single transcript that forms base-paired hairpins. Base pairing of siRNAs and miRNAs can be perfect (i.e., fully complementary) or imperfect, including bulges in the duplex region. Mechanisms of utilizing RNAi molecules in mammalian cell are described in more detail below.

RNAi can be used a powerful tool for in vitro, ex vivo, or in vivo studies of gene function in mammalian cells and for therapy in both human and veterinary contexts and as a tool for in vitro and in vivo studies of gene function. Inhibition of a target gene via RNAi is generally sequence-specific.

While not wishing to be bound by theory, it is believed that there are at least three mechanisms of utilizing RNAi in mammalian cells. The first is cytoplasmic delivery of siRNA molecules, which are either chemically synthesized or enzymatically processed dsRNA. These siRNAs are introduced into cells using standard transfection methods. The siRNAs enter the RISC to silence target mRNA expression.

The second mechanism is nuclear delivery, e.g., via viral vectors, of gene expression cassettes expressing a short hairpin RNA (shRNA). The shRNA is modeled on micro interfering RNA (miRNA), an endogenous trigger of the RNAi pathway (Lu et al., 2005, Advances in Genetics 54:117-142). Conventional shRNAs, which mimic pre-miRNA, are transcribed by RNA Polymerase II or III as single-stranded molecules that form stem-loop structures. Once produced, they exit the nucleus, are cleaved by DICER, and enter the RISC as siRNAs.

The third mechanism is similar to the second mechanism except that the shRNA is modeled on primary miRNA (e.g., shRNA-miR) rather than pre-miRNA transcripts (Fewell et al., 2006, Drug Discovery Today 11: 975-982). The use of this transcript produces a more physiological shRNA that reduces toxic effects. The shRNA-miR is first cleaved to produce shRNA and then cleaved again by DICER to produce siRNA. The siRNA is then incorporated into the RISC for target mRNA degradation.

For mRNA degradation, translational repression, or deadenylation, mature miRNAs or siRNAs are loaded into the RNA Induced Silencing Complex (RISC) by the RISC-loading complex (RLC). Subsequently, the guide strand leads the RISC to cognate target mRNAs in a sequence-specific manner and the Slicer component of RISC hydrolyses the phosphodiester bound coupling the target mRNA nucleotides paired to nucleotide 10 and 11 of the RNA guide strand. Slicer forms together with distinct classes of small RNAs the RNAi effector complex, which is the core of RISC. Therefore, in an embodiment, the "guide strand" is that portion of the double-stranded RNA that associates with RISC as opposed to the "passenger strand", which is not associated with RISC.

As used herein, the term "modified pri-miRNA-like molecule" or "shRNA-miR molecule" refers to micro-RNA embedded shRNAs (miRNA-based shRNAs), wherein the guide and passenger strands of an siRNA duplex are incorporated into an existing (or natural) pri-miRNA or into a modified or synthetic (designed) pri-miRNA. When transcribed, a modified pri-miRNA-like molecule or shRNA-miRNA molecule forms a structure identical or similar to a natural pri-miRNA. The modified pri-miRNA-like molecule or shRNA-miR molecule can be subsequently processed by Drosha and its co-factors into modified pre-miRNA or shRNA. The modified pri-miRNA-like molecule or shRNA-miR molecule can have a 5' flanking region, terminal loop region, and/or a 3' flanking region that is substantially identical to the 5' flanking region, terminal loop region, and/or a 3' flanking region of a naturally occurring pri-miRNA. In some embodiments, one or more insertions, deletions, and substitutions can be introduced into the 5' flanking region, terminal loop region, and/or the 3' flanking region of a naturally-occurring pri-miRNA sequence to produce the backbone of a pri-miRNA-like molecule or shRNA-miR molecule. While not wishing to be bound by theory, it is believed that any naturally-occurring pri-miRNA can provide a backbone for designing modified pri-miRNA-like molecules or shRNA-miR molecules. For example, any miRNAs described in miRBase can be used. miRBase Release 21: June 2014 is publically available at mirbase.org/pub/mirbase, which is incorporated by reference herein in its entirety (Kozomara and Griffiths-Jones NAR 2014 42:D68-D73; Kozomara and Griffiths-Jones NAR 2011 39:D152-D157; Griffiths-Jones et al. NAR 2008 36:D154-D158; Griffiths-Jones et al. NAR 2006 34:D140-D144; Griffiths-Jones NAR 2004 32:D109-D111).

The typical structural features of primary miRNAs and miRNA precursors, and their relevance to miRNA biogenesis and small interfering RNA/short hairpin RNA design are known in the art, e.g., as described in Krol et al. (2004) The Journal of Biological Chemistry, 279, 42230-42239.

Without wishing to be bound by theory, it is believed that primary transcripts of the miRNA genes, pri-miRNAs are processed in the nucleus to pre-miRNAs by the ribonuclease Drosha (Lee et al. (2003) Nature 425, 415-419) and exported from the nucleus by Exportin-5 (Lund et al. (2003) Science 303, 95-98). The 60-90-nt miRNA precursors form the stem-loop structures and the cytoplasmic ribonuclease class III enzyme Dicer (Hutvágner et al. (2002) Science 297, 2056-2060) excises miRNAs from the pre-miRNA hairpin stem. Dicer, either alone or with the help of Drosha, cleaves both strands of the precursor to form a double-stranded miRNA/miRNA® duplex (Lee et al. (2003) Nature 425, 415-419), and typically only one strand (e.g., a guide strand as opposed to a passenger strand) accumulates which enters the RNAi-induced silencing complex (RISC) (Khvorova et al. (2003) Cell 115, 209-216).

As used herein, a "stem-loop structure" refers to a nucleic acid having a secondary structure that includes a region of nucleotides which are known or predicted to form a double strand or duplex (stem portion or stem region) that is linked on one side by a region of predominantly single-stranded nucleotides (loop portion or terminal loop region). The terms "hairpin" and "fold-back" structures can also be used to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches. The stem region can contain an artificial RNA molecule (e.g., RNAi molecule) as described herein.

As used herein, a terminal loop region refers to a region flanked by a guide strand and a passenger strand of an RNAi molecule (e.g., a double-stranded siRNA or miRNA/miRNA®).

As described herein, a stem region can be a region formed by a guide strand and a passenger strand of an RNAi molecule (e.g., a double-stranded siRNA or miRNA/miRNA®) and connected to a terminal loop region. The guide strand can be either 5' or 3' to the terminal loop region. Likewise, the passenger strand can be either 3' or 5' to the terminal loop region. The stem region can form a duplex with or without one or more mismatches or bulges.

As used herein, a 5' flanking region refers to a region immediately adjacent to a strand (either a guide strand or a passenger strand) that is 5' to the terminal loop region. As used herein, a 3' flanking region refers to a region immediately adjacent to a strand (either a guide strand or a passenger strand) that is 3' to the terminal loop region. The 5' flanking region or 3' flanking region described herein, as well as the structure formed by the 5' and 3' flanking regions, may have one or more structural features of a corresponding region of a naturally-occurring pri-miRNA. While not wishing to be bound by theory, it is believed that in an embodiment, the presence of the 5' flanking region and/or 3' flanking region may improve production of an RNAi molecule, e.g., an siRNA and miRNA, embedded in an shRNA-like molecule or modified pri-miRNA-like molecule described herein. The length of the 5' flanking region or 3' flanking region may vary. Exemplary approaches for selecting a 5' flanking region or 3' flanking region (e.g., determining the optimal length of the 5' flanking region or 3' flanking region) are described herein in the examples.

One can design and express shRNA-like molecules, modified pri-miRNA-like molecules (e.g., shRNA-miR molecules), or artificial RNA molecules (e.g., RNAi molecules) based on the features of the native gene encoding the pri-miRNA. In particular, the pri-miRNA architecture can be used to express shRNA-like molecules, modified pri-miRNA-like molecules (e.g., shRNA-miR molecules), or artificial RNA molecules (e.g., RNAi molecules) from pol II promoter-based expression plasmids by using a variety of RNA pol II-based expression vectors or even from pol III promoter-based expression plasmids using pol III-dependent promoters. In certain embodiments, expression vectors may employ use of expression cassettes comprising the sequence encoding an shRNA-like molecule, modified pri-miRNA-like molecule (e.g., shRNA-miR molecule), or artificial RNA molecule (e.g., RNAi molecule). In certain embodiments, expression vectors encoding shRNA-like molecules, modified pri-miRNA-like molecules (e.g., shRNA-miR molecules), or artificial RNA molecules (e.g., RNAi molecules) may be based on self-inactivating lentivirus (SIN) vector backbones. In certain embodiments, expression vectors encoding shRNA-like molecules, modified pri-miRNA-like molecules (e.g., shRNA-miR molecules), or artificial RNA molecules (e.g., RNAi molecules) may be based on CMV-based or MSCV-based vector backbones. Generally, appropriate vector backbones include vector backbones used in construction of expression vectors for conventional shRNAs. Exemplary use of expression cassettes in construction of shRNA expression vectors also useful in the construction of expression cassettes encoding the modified pri-miRNA molecules or shRNA-miR molecules of the disclosure can be found, e.g., in Gottwein E. and Cullen B. Meth. Enzymol. 427:229-243, 2007, Dickens et al., Nature Genetics, 39:914-921, 2007, Chen et al, Science 303: 83-86, 2004; Zeng and Cullen, RNA 9: 112-123, 2003, the contents of which are specifically incorporated herein by reference.

Exemplary guidelines for designing RNAi molecules, e.g., siRNAs or shRNAs, are known in the art, e.g., as described in Elbashir, et al. (2001) EMBO J 20: 6877-6888, Brown et al. (2002) Ambion TechNotes 9(1): 3-5; Sui. et al. (2002) Proc. Natl. Acad. Sci. USA 99(8): 5515-5520; Lee et al. Nature Biotechnology 20:500-505; Yu et al. (2002) Proc. Natl. Acad. Sci. USA 99(9): 6047-6052; Paul et al. (2002) Nature Biotechnology 20: 505-508; Brummelkamp et al. (2002) Science 296: 550-553; Jacque, et al. (2002) Nature 418: 435-438; Miyagishi et al. (2002) Nature Biotechnology 20: 497-500; Paddison et al. (2002) Genes Devel. 16: 948-958, the contents of which are specifically incorporated herein by reference.

The nucleic acid molecules described herein can be modified, e.g., to enhance stability in vivo. Modified nucleic acids include molecules containing nucleotide analogues, including those molecules having additions, deletions, and/or substitutions in the nucleobase, sugar, or backbone; and molecules that are cross-linked or otherwise chemically modified. The modified nucleotide(s) may be within portions of the nucleic acid molecule, or throughout it. For instance, the shRNA-like molecule may be modified, or contain modified nucleic acids in regions at its 5' end, its 3' end, or both, and/or within the guide strand, passenger strand, or both, and/or within nucleotides that overhang the 5' end, the 3' end, or both. See U.S. Pat. Nos. 6,107,094 and 5,898,031; U.S. Publication Nos. 2008/0249039, 2007/0191294, 2008/0213891, 2007/0135372, and 2005/0020521; all of which are hereby incorporated by reference.

Vectors

The disclosure provides vectors that include a nucleic acid molecule (e.g., shRNA cluster or artificial miRNA cluster) described herein, e.g., for expression of an shRNA-like molecule, modified pri-miRNA-like molecule (e.g., shRNA-miR molecule), or artificial RNA molecule (e.g., RNAi molecule) described herein.

In certain embodiments, expression vectors encoding shRNA-like molecules, modified pri-miRNA-like molecules (e.g., shRNA-miR molecules), or artificial RNA molecules (e.g., RNAi molecules) as described herein, may be based on self-inactivating lentivirus (SIN) vector backbones. In certain embodiments, expression vectors encoding the shRNA-like molecules, modified pri-miRNA-like molecules (e.g., shRNA-miR molecules), or artificial RNA molecules (e.g., RNAi molecules) described herein may be based on CMV-based or MSCV-based vector backbones. Exemplary vector backbones and methodologies for construction of expression vectors suitable for use with the shRNA clusters or nucleic acid molecules (e.g., artificial miRNA clusters) described herein, and methods for introducing such expression vectors into various mammalian cells can be found, e.g., in Premsrurit P K. et al., Cell, 145(1):145-158, 2011, Gottwein E. and Cullen B. Meth. Enzymol. 427:229-243, 2007, Dickens et al., Nature Genetics, 39:914-921, 2007, Chen et al., Science 303: 83-86, 2004; Zeng and Cullen, RNA 9: 112-123, 2003, the contents of which are specifically incorporated herein by reference.

The vectors can be targeting vectors, such as those using lip recombination into the colA locus allowing single copy integration. Other targeting sites in the mouse genome include, but are not limited to ROSA26 and HPRT. Additionally, transposase may be used to introduce mimics into the genome of an animal or the cell of an animal. See Premsrurit P K. et al., Cell, 145(1):145-158, (2011), the contents of which are specifically incorporated herein by reference.

General principles of vector construction and expression of sequences from vector constructs, as well as methods of making and using the vectors, are described, e.g., in International Publication No. WO 09/055,724, which is incorporated herein by reference.

Artificial RNA molecules (e.g., RNAi molecules) described herein can be expressed from vectors to provide sustained silencing and high yield delivery into almost any cell type. In a certain embodiment, the vector is a viral vector. Exemplary viral vectors include retroviral, including lentiviral, adenoviral, baculoviral, and avian viral vectors. The use of viral vector-based RNAi delivery not only allows for stable single-copy genomic integrations, but also avoids the non-sequence specific response via cell-surface toll-like receptor 3 (TLR3).

Retroviruses from which the retroviral plasmid vectors can be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector can be employed to transduce packaging cell lines to form producer cell lines. Examples of packaging cells which can be transfected include, but are not limited to, the PE501, PA317. R-2, R-AM, PA12, T19-14x, VT-19-17-H2, RCRE, RCRIP, GP+E-86, GP+envAm12, and DAN cell lines as described in Miller, Human Gene Therapy 1:5-14 (1990), which is incorporated herein by reference in its entirety. The vector can transduce the packaging cells through any means known in the art. A producer cell line generates infectious retroviral vector particles which include polynucleotide encoding a DNA replication protein. Such retroviral vector particles can then be employed to transduce eukaryotic cells, either in vitro or in vivo. The transduced eukaryotic cells will express a DNA replication protein.

In certain embodiments, cells can be engineered using a lentivirus and lentivirus based vectors. Such an approach is advantageous in that it allows for tissue-specific expression in animals through use of cell type-specific pol II promoters, efficient transduction of a broad range of cell types, including nondividing cells and cells that are hard to infect by retroviruses, and inducible and reversible gene knockdown by use of tet-responsive and other inducible promoters. Methods for expressing artificial RNA molecules (e.g., RNAi molecules) by producing and using lentivirus engineered cells are known in the art. For exemplary descriptions of such methods, see, for example, Stegmeier F. et al., Proc Acad Sci USA 2005, 102(37):13212-13217, Klinghoffer et al., RNA 2010, 16:879-884, the contents of which are specifically incorporated herein. Efficient production of replication-incompetent recombinant lentivirus may be achieved, for example, by co-transfection of expression vectors and packaging plasmids using commercially available packaging cell lines, such as TLA-HEK293™, and packaging plasmids, available from Thermo Scientific/Open Biosystems, Huntsville, Ala.

In certain embodiments, cells can be engineered using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that can integrate its DNA into nondividing cells. Vectors containing as little as 300 base pairs of AAV can be packaged and can integrate, but space for exogenous DNA is limited to about 4.5 kb. Methods for producing and using such AAVs are known in the art. See, for example, International Publication No. WO 2015/031686, U.S. Pat. Nos. 7,927,585, 7,906,111, 7,261,544, 6,221,646, 5,589,377, 5,478,745, 5,474,935, 5,436,146, 5,436,146, 5,173,414, and 5,139,941, and. For example, an AAV vector can include all the sequences necessary for DNA replication, encapsidation, and host-cell integration. The recombinant AAV vector can be transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct. These viral particles are then used to transduce eukaryotic cells.

Typically any method for introducing a nucleic acid construct into cells can be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle can be used to accomplish both efficient introduction of an expression construct into the cell and transcription of the encoded shRNA. Other methods known in the art for introducing nucleic acids to cells can be used, such as lipid-mediated carrier transport, chemical mediated transport, such as calcium phosphate, and the like. Thus the shRNA-encoding nucleic acid construct can be introduced along with components that perform one or more of the following activities: enhance RNA uptake by the cell, promote annealing of the duplex strands, stabilize the annealed strands, or otherwise increase inhibition of the target gene.

Expression of endogenous miRNAs is controlled by RNA polymerase II (Pol II) promoters. It has been shown that shRNAs are also most efficiently driven by Pol II promoters, as compared to RNA polymerase III promoters (Dickins et al., 2005, Nat. Genet. 39: 914-921). Therefore, in a certain embodiment, the coding sequence of the RNAi molecule is controlled by an inducible promoter or a conditional expression system, including, without limitation, RNA polymerase type II promoters. Examples of useful promoters in the context of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types. A certain embodiment uses tetracycline-responsive promoters, one of the most effective conditional gene expression systems in in vitro and in vivo studies. See International Publication No. WO 2004/029219, European Publication No. EP 2166107, and Fewell et al., 2006, Drug Discovery Today 11: 975-982, for an exemplary description of inducible shRNA.

To facilitate the monitoring of the target gene knockdown, cells harboring the RNAi-expressing construct can additionally comprise a marker or reporter construct, such as a fluorescent construct. The reporter construct can express a marker, such as green fluorescent protein (GFP), enhanced green fluorescent protein (EGFP), *Renilla Reniformis* green fluorescent protein, GFPmut2, GFPuv4, yellow fluorescent protein (YFP), such as VENUS, enhanced yellow fluorescent protein (EYFP), cyan fluorescent protein (CFP), enhanced cyan fluorescent protein (ECFP), blue fluorescent protein (BFP), enhanced blue fluorescent protein (EBFP), and citrine and red fluorescent protein from discosoma (dsRED). Other suitable detectable markers include chloramphenicol acetyltransferase (CAT), luminescent proteins such as luciferase lacZ (β-galactosidase) and horseradish peroxidase (HRP), nopaline synthase (NOS), octopine synthase (OCS), and alkaline phosphatase. The marker gene can be separately introduced into the cell harboring the shRNA construct (e.g., co-transfected, etc.). Alternatively, the marker gene can be on the shRNA construct and the marker gene expression can be controlled by the same or a separate translation unit, for example, by an IRES (internal ribosomal entry site). In one aspect of the invention, marker genes can be incorporated into "sensor" expression vectors for use in high throughput methods for determining the knockdown efficiency against particular genes and for identifying the most potent target sequences for a particular target gene. Such methods, including the design and use of plasmids and reporter constructs for testing the potency of particular shRNA molecules are described, e.g., in International Publication No. WO2009/055724, the contents of which are herein specifically incorporated by reference in its entirety.

Reporters can also be those that confer resistance to a drug, such as neomycin, ampicillin, bleomycin, chloramphenicol, gentamycin, hygromycin, kanamycin, lincomycin, methotrexate, phosphinothricin, puromycin, doxycycline, and tetracyclin. Reporters can also be lethal genes, such as herpes simplex virus-thymidine kinase (HSV-TK) sequences, as well as sequences encoding various toxins including the diphtheria toxin, the tetanus toxin, the cholera toxin, and the pertussis toxin. A further negative selection marker is the hypoxanthine-guanine phosphoribosyl transferase (HPRT) gene for negative selection in 6-thioguanine.

To facilitate the quantification of specific shRNAs in a complex population of cells infected with a library of shRNAs, each shRNA construct can additionally comprise a barcode. A barcode is a unique nucleotide sequence (generally a 19-mer) linked to each shRNA. The barcode can be used to monitor the abundance of each shRNA via microarray hybridization (Fewell et al., 2006, Drug Discovery Today 11: 975-982). In a certain embodiment, each shRNA construct also comprises a unique barcode. For more information on the use of barcodes in shRNA pooled analyses, see WO 04/029219, Bemards et al., 2006, Nature Methods 3: 701-706, and Chang et al., 2006, Nature Methods 3: 707-714.

Exemplary Target Genes

The nucleic acid molecule (e.g., shRNA cluster or artificial miRNA cluster) described herein can be used to express artificial RNA molecules (e.g., RNAi molecules) that target any genes. For example, the target genes can include mammalian genes (e.g., human genes) or viral genes. In an embodiment, the target gene is a mammalian gene encoding a viral receptor or co-receptor, e.g., an HIV co-receptor, e.g., CCR5 or CXCR4. In another embodiment, the target gene is a viral gene, e.g., an HIV gene, e.g., Gag, Env, Tat, Pol2, Pol1, or Vif. Artificial RNA molecules (e.g., RNAi molecules) can be designed based on the gene sequences provided herein or known in the art.

Exemplary CCR and HIV gene sequences are provided as follows: *Homo sapiens* CC chemokine receptor 5 (CCR5), (Seq ID No. 1).

CTGTTTAAAGACAAAAAGGCCCCAAAAAGGAGGGATGGCACGAAACACCC

TCCAATATGGGCATGGAGTCTAGAGTGACAAAGTGATCAAAAGTTCATTT

CCTATGGGGTGTCCGAATGTACTTAATAATAAAAAGAGAACAAGAGCCAT

GCAAACTGAGAGGGACAAAGTAGAAAGAGTAGCAGACACCTAGCAACTAA

GTCACAGCATGATAAGCTGCTAGCTTGTTGTCATTATTGTATCCAGAACA

ACATTTCATTTAAATGCTGAAGAATTTCCCATGGGTCCCCACTTTCTTGT

GAATCCTTGGGCTGAACCCCCCCGTCCTGAGTGGTTACTAGAACACACCT

CTGGACCAGAAACACAAGAGTGGAGTAACACACACTGCAAAGCTGTGCTT

CCTTGTTTCAGCCTGTGAATCCTCACCTTGTTTCCCATCTAGCCTATATT

TTTCAAACTAACTTGGCCATAGAATCATGTCGTATTTAGGGTGGAAGCTG

CCCCAGGTCTAGCGCGTCATTTAACAGATGAGGAAATGGAAGCTTGGGCA

GTGGAAGTATCTTGCCGAGGTCACACAGCAAGTCAGCAGCACAGCGTGTG

TGACTCCGAGCCTGCTCCGCTAGCCCACATTGCCCTCTGGGGGTGAGTAT

GTCTTCACATCCTCCAATACCCCTAATGACAGACAAACAGAACATGGCAA

AGCCTCAGCTCTGCATGGTGAAAGTAAGAACCAGCAATTGCCACAAACAG

AAATACAGTGTTGGTCCGGCAGCCTCCGGGGGTTCTGCACAAGTGGATTA

CCAGTGAATACAAGGCTATCTATCTTCCGAAAAACCAAAGTTGTATTTAT

GCTATCTATTTTCTATAAAATTTTATATTAATTTACTTGTCCTATTTTTG

AACTCTTTCAAAAGCACACTTTATATTTCCCCTGCTTAAACAGTCCCCCG

AGGGTGGGTGCCCAAAAGGCTCTACACTTGTTATCATTCCCTCTCCACCA

CAGGCATATTGAGTAAGTTTGTATTTGGGTTTTTTTAAAACCTCCACTCT

ACAGTTAAGAAAACTAAGGCACAGAGCTTCAATAATTTGGTCAGAGCCAA

GTAGCAGTAATGAAGCTGGAGGTTAAACCCAGCAGCATGACTGCAGTTCT

TAATCAATGCCTTTTGAATTGCACATATGGGATGAACTAGAACATTTTCT

CGATGATTCGCTGTCCTTGTTATGATTATGTTACTGAGCTCTGTTGTAGC

ACAGACATATGTCCCTATATGGGGCGGGGGTGGGGGTGTCTTGATCGCTG

GGCTATTTCTATACTGTTCTGGCTTTTCCCAAGCAGTCATTTCTTTCTAT

CCTCCAAGCACCAGCAATTAGCTTTACCTTTTCAGCTTCTAGTTTGCTGA

-continued

AACTAATCTGCTATAGACAGAGACTCCGGTGAACCAATTTTATTAGGATT

TGATCAAATAAACTCTCTCTGACAAAGGACTGCTGAAAGAGTAACTAAGA

GTTTGATGTTTACTGAGTGCATAGTATGTGCTAGATGCTGGCCGTGGATG

CCTCATAGAATCCTCCCAACAACTCATGAAATGACTACTGTCATTCAGCC

CAATACCCAGACGAGAAAGCTGAGGGTAAGACAGGTTTCAAGCTTGGCAG

TCTGACTACAGAGGCCACTGGCTTAGCCCCTGGGTTAGTCTGCCTCTGTA

GGATTGGGGGCACGTAATTTTGCTGTTTGGGGTCTCATTTGCCTTCTTAG

AGATCACAAGCCAAAGCTTTTTATTCTAGAGCCAAGGTCACGGAAGCCCA

GAGGACATCTTGTGGCTCGGGAGTAGCTCTCTGCTGTCTTCTCAGCTCTG

CTGACAATACTTGAGATTTTCAGATGTCACCAACCGCCAAGAGAGCTTGA

TATGACTGTATATAGTATAGTCATAAAGAACCTGAACTTGACCATATACT

TATGTCATGTGGAAAATTTCTCATAGCTTCAGATAGATTATATCTGGAGT

GAAGGATCCTGCCACCTACGTATCTGGCATAGTGTGAGTCCTCATAAATG

CTTACTGGTTTGAAGGGCAACAAAATAGTGAACAGAGTGAAAATCCCCAC

TAAGATCCTGGGTCCAGAAAAAGATGGGAAACCTGTTTAGCTCACCCGTG

AGCCCATAGTTAAAACTCTTTAGACAACAGGTTGTTTCCGTTTACAGAGA

ACAATAATATTGGGTGGTGAGCATCTGTGTGGGGGTTGGGGTGGGATAGG

GGATACGGGGAGAGTGGAGAAAAAGGGGACACAGGGTTAATGTGAAGTCC

AGGATCCCCCTCTACATTTAAAGTTGGTTTAAGTTGGCTTTAATTAATAG

CAACTCTTAAGATAATCAGAATTTTCTTAACCTTTTAGCCTTACTGTTGA

AAAGCCCTGTGATCTTGTACAAATCATTTGCTTCTTGGATAGTAATTTCT

TTTACTAAAATGTGGGCTTTTGACTAGATGAATGTAAATGTTCTTCTAGC

TCTGATATCCTTTATTCTTTATATTTTCTAACAGATTCTGTGTAGTGGGA

TGAGCAGAGAACAAAAACAAAATAATCCAGTGAGAAAAGCCCGTAAATAA

ACCTTCAGACCAGAGATCTATTCTCCAGCTTATTTTAAGCTCAACTTAAA

AAGAAGAACTGTTCTCTGATTCTTTTCGCCTTCAATACACTTAATGATTT

AACTCCACCCTCCTTCAAAAGAAACAGCATTTCCTACTTTTATACTGTCT

ATATGATTGATTTGCACAGCTCATCTGGCCAGAAGAGCTGAGACATCCGT

TCCCCTACAAGAAACTCTCCCCGGTAAGTAACCTCTCAGCTGCTTGGCCT

GTTAGTTAGCTTCTGAGATGAGTAAAAGACTTTACAGGAAACCCATAGAA

GACATTTGGCAAACACCAAGTGCTCATACAATTATCTTAAAATATAATCT

TTAAGATAAGGAAAGGGTCACAGTTTGGAATGAGTTTCAGACGGTTATAA

CATCAAAGATACAAAACATGATTGTGAGTGAAAGACTTTAAAGGGAGCAA

TAGTATTTTAATAACTAACAATCCTTACCTCTCAAAAGAAAGATTTGCAG

AGAGATGAGTCTTAGCTGAAATCTTGAAATCTTATCTTCTGCTAAGGAGA

ACTAAACCCTCTCCAGTGAGATGCCTTCTGAATATGTGCCCACAAGAAGT

TGTGTCTAAGTCTGGTTCTCTTTTTTCTTTTTCCTCCAGACAAGAGGGAA

GCCTAAAAATGGTCAAAATTAATATTAAATTACAAACGCCAAATAAAATT

TTCCTCTAATATATCAGTTTCATGGCACAGTTAGTATATAATTCTTTATG

GTTCAAAATTAAAAATGAGCTTTTCTAGGGGCTTCTCTCAGCTGCCTAGT

-continued

CTAAGGTGCAGGGAGTTTGAGACTCACAGGGTTTAATAAGAGAAAATTCT

CAGCTAGAGCAGCTGAACTTAAATAGACTAGGCAAGACAGCTGGTTATAA

GACTAAACTACCCAGAATGCATGACATTCATCTGTGGTGGCAGACGAAAC

ATTTTTTATTATATTATTTCTTGGGTATGTATGACAACTCTTAATTGTGG

CAACTCAGAAACTACAAACACAAACTTCACAGAAAATGTGAGGATTTTAC

AATTGGCTGTTGTCATCTATGACCTTCTCTGGGACTTGGGCACCCGGCCA

TTTCACTCTGACTACATCATGTCACCAAACATCTGATGGTCTTGCCTTTT

AATTCTCTTTTCGAGGACTGAGAGGGAGGGTAGCATGGTAGTTAAGAGTG

CAGGCTTCCCGCATTCAAAATCGGTTGCTTACTAGCTGTGTGGCTTTGAG

CAAGTTACTCACCCTCTCTGTGCTTCAAGGTCCTTGTCTGCAAAATGTGA

AAAATATTTCCTGCCTCATAAGGTTGCCCTAAGGATTAAATGAATGAATG

GGTATGATGCTTAGAACAGTGATTGGCATCCAGTATGTGCCCTCGAGGCC

TCTTAATTATTACTGGCTTGCTCATAGTGCATGTTCTTTGTGGGCTAACT

CTAGCGTCAATAAAAATGTTAAGACTGAGTTGCAGCCGGGCATGGTGGCT

CATGCCTGTAATCCCAGCATTCTAGGAGGCTGAGGCAGGAGGATCGCTTG

AGCCCAGGAGTTCGAGACCAGCCTGGGCAACATAGTGTGATCTTGTATCT

ATAAAAATAAACAAAATTAGCTTGGTGTGGTGGCGCCTGTAGTCCCCAGC

CACTTGGAGGGGTGAGGTGAGAGGATTGCTTGAGCCCGGGATGGTCCAGG

CTGCAGTGAGCCATGATCGTGCCACTGCACTCCAGCCTGGGCGACAGAGT

GAGACCCTGTCTCACAACAACAACAACAACAACAAAAAGGCTGAGCTGCA

CCATGCTTGACCCAGTTTCTTAAAATTGTTGTCAAAGCTTCATTCACTCC

ATGGTGCTATAGAGCACAAGATTTTATTTGGTGAGATGGTGCTTTCATGA

ATTCCCCCAACAGAGCCAAGCTCTCCATCTAGTGGACAGGGAAGCTAGCA

GCAAACCTTCCCTTCACTACAAAACTTCATTGCTTGGCCAAAAAGAGAGT

TAATTCAATGTAGACATCTATGTAGGCAATTAAAAACCTATTGATGTATA

AAACAGTTTGCATTCATGGAGGGCAACTAAATACATTCTAGGACTTTATA

AAAGATCACTTTTTATTTATGCACAGGGTGGAACAAGATGGATTATCAAG

TGTCAAGTCCAATCTATGACATCAATTATTATACATCGGAGCCCTGCCAA

AAAATCAATGTGAAGCAAATCGCAGCCCGCCTCCTGCCTCCGCTCTACTC

ACTGGTGTTCATCTTTGGTTTTGTGGGCAACATGCTGGTCATCCTCATCC

TGATAAACTGCAAAAGGCTGAAGAGCATGACTGACATCTACCTGCTCAAC

CTGGCCATCTCTGACCTGTTTTTCCTTCTTACTGTCCCCTTCTGGGCTCA

CTATGCTGCCGCCCAGTGGGACTTTGGAAATACAATGTGTCAACTCTTGA

CAGGGCTCTATTTTATAGGCTTCTTCTCTGGAATCTTCTTCATCATCCTC

CTGACAATCGATAGGTACCTGGCTGTCGTCCATGCTGTGTTTGCTTTAAA

AGCCAGGACGGTCACCTTTGGGGTGGTGACAAGTGTGATCACTTGGGTGG

TGGCTGTGTTTGCGTCTCTCCCAGGAATCATCTTTACCAGATCTCAAAAA

GAAGGTCTTCATTACACCTGCAGCTCTCATTTTCCATACAGTCAGTATCA

ATTCTGGAAGAATTTCCAGACATTAAAGATAGTCATCTTGGGGCTGGTCC

TGCCGCTGCTTGTCATGGTCATCTGCTACTCGGGAATCCTAAAAACTCTG

CTTCGGTGTCGAAATGAGAAGAAGAGGCACAGGGCTGTGAGGCTTATCTT

-continued

CACCATCATGATTGTTTATTTTCTCTTCTGGGCTCCCTACAACATTGTCC

TTCTCCTGAACACCTTCCAGGAATTCTTTGGCCTGAATAATTGCAGTAGC

TCTAACAGGTTGGACCAAGCTATGCAGGTGACAGAGACTCTTGGGATGAC

GCACTGCTGCATCAACCCCATCATCTATGCCTTTGTCGGGGAGAAGTTCA

GAAACTACCTCTTAGTCTTCTTCCAAAAGCACATTGCCAAACGCTTCTGC

AAATGCTGTTCTATTTTCCAGCAAGAGGCTCCCGAGCGAGCAAGCTCAGT

TTACACCCGATCCACTGGGGAGCAGGAAATATCTGTGGGCTTGTGACACG

GACTCAAGTGGGCTGGTGACCCAGTCAGAGTTGTGCACATGGCTTAGTTT

TCATACACAGCCTGGGCTGGGGGTGGGGTGGGAGAGGTCTTTTTTAAAAG

GAAGTTACTGTTATAGAGGGTCTAAGATTCATCCATTTATTTGGCATCTG

TTTAAAGTAGATTAGATCTTTTAAGCCCATCAATTATAGAAAGCCAAATC

AAAATATGTTGATGAAAAATAGCAACCTTTTTATCTCCCCTTCACATGCA

TCAAGTTATTGACAAACTCTCCCTTCACTCCGAAAGTTCCTTATGTATAT

TTAAAAGAAAGCCTCAGAGAATTGCTGATTCTTGAGTTTAGTGATCTGAA

CAGAAATACCAAAATTATTTCAGAAATGTACAACTTTTTACCTAGTACAA

GGCAACATATAGGTTGTAAATGTGTTTAAAACAGGTCTTTGTCTTGCTAT

GGGGAGAAAAGACATGAATATGATTAGTAAAGAAATGACACTTTTCATGT

GTGATTTCCCCTCCAAGGTATGGTTAATAAGTTTCACTGACTTAGAACCA

GGCGAGAGACTTGTGGCCTGGGAGAGCTGGGGAAGCTTCTTAAATGAGAA

GGAATTTGAGTTGGATCATCTATTGCTGGCAAAGACAGAAGCCTCACTGC

AAGCACTGCATGGGCAAGCTTGGCTGTAGAAGGAGACAGAGCTGGTTGGG

AAGACATGGGGAGGAAGGACAAGGCTAGATCATGAAGAACCTTGACGGCA

TTGCTCCGTCTAAGTCATGAGCTGAGCAGGGAGATCCTGGTTGGTGTTGC

AGAAGGTTTACTCTGTGGCCAAAGGAGGGTCAGGAAGGATGAGCATTTAG

GGCAAGGAGACCACCAACAGCCCTCAGGTCAGGGTGAGGATGGCCTCTGC

TAAGCTCAAGGCGTGAGGATGGGAAGGAGGGAGGTATTCGTAAGGATGGG

AAGGAGGGAGGTATTCGTGCAGCATATGAGGATGCAGAGTCAGCAGAACT

GGGGTGGATTTGGTTTGGAAGTGAGGGTCAGAGAGGAGTCAGAGAGAATC

CCTAGTCTTCAAGCAGATTGGAGAAACCCTTGAAAAGACATCAAGCACAG

AAGGAGGAGGAGGAGGTTTAGGTCAAGAAGAAGATGGATTGGTGTAAAAG

GATGGGTCTGGTTTGCAGAGCTTGAACACAGTCTCACCCAGACTCCAGGC

TGTCTTTCACTGAATGCTTCTGACTTCATAGATTTCCTTCCCATCCCAGC

TGAAATACTGAGGGGTCTCCAGGAGGAGACTAGATTTATGAATACACGAG

GTATGAGGTCTAGGAACATACTTCAGCTCACACATGAGATCTAGGTGAGG

ATTGATTACCTAGTAGTCATTTCATGGGTTGTTGGGAGGATTCTATGAGG

CAACCACAGGCAGCATTTAGCACATACTACACATTCAATAAGCATCAAAC

TCTTAGTTACTCATTCAGGGATAGCACTGAGCAAAGCATTGAGCAAAGGG

GTCCCATATAGGTGAGGGAAGCCTGAAAAACTAAGATGCTGCCTGCCCAG

TGCACACAAGTGTAGGTATCATTTTCTGCATTTAACCGTCAATAGGCAAA

GGGGGGAAGGGACATATTCATTTGGAAATAAGCTGCCTTGAGCCTTAAAA

-continued

CCCACAAAAGTACAATTTACCAGCCTCCGTATTTCAGACTGAATGGGGGT

GGGGGGGGCGCCTTAGGTACTTATTCCAGATGCCTTCTCCAGACAAACCA

GAAGCAACAGAAAAAATCGTCTCTCCCTCCCTTTGAAATGAATATACCCC

TTAGTGTTTGGGTATATTCATTTCAAAGGGAGAGAGAGAGGTTTTTTTCT

GTTCTTTCTCATATGATTGTGCACATACTTGAGACTGTTTTGAATTTGGG

GGATGGCTAAAACCATCATAGTACAGGTAAGGTGAGGGAATAGTAAGTGG

TGAGAACTACTCAGGGAATGAAGGTGTCAGAATAATAAGAGGTGCTACTG

ACTTTCTCAGCCTCTGAATATGAACGGTGAGCATTGTGGCTGTCAGCAGG

AAGCAACGAAGGGAAATGTCTTTCCTTTTGCTCTTAAGTTGTGGAGAGTG

CAACAGTAGCATAGGACCCTACCCTCTGGGCCAAGTCAAAGACATTCTGA

CATCTTAGTATTTGCATATTCTTATGTATGTGAAAGTTACAAAUGCTTGA

AAGAAAATATGCATCTAATAAAAAACACCTTCTA

HIV-1 Gag, (Seq ID No. 2).

ATGGGTGCGAGAGCGTCAGTATTAAGCGGGGGAAAATTAGATCGATGGGA

AAAAATTCGGTTAAGGCCAGGGGGAAAGAAAAAATATAAATTAAAACATA

TAGTATGGGCAAGCAGGGAGCTAGAACGATTCGCAGTTAATCCTGGCCTG

TTAGAAACATCAGAAGGCTGTAGACAAATACTGGGACAGCTACAACCATC

CCTTCAGACAGGATCAGAAGAACGTAGATCATTATATAATACAGTAGCAA

CCCTCTATTGTGTGCATCAAAGGATAGAGATAAAAGACACCAAGGAAGCT

TTAGACAAGATAGAGGAAGAGCAAAACAAAAGTAAGAAAAAAGCACAGCA

AGCAGCAGCTGACACAGGACACAGCAGCCAGGTCAGCCAAAATTACCCTA

TAGTGCAGAACATCCAGGGGCAAATGGTACATCAGGCCATATCACCTAGA

ACTTTAAATGCATGGGTAAAAGTAGTAGAAGAGAAGGCTTTCAGCCCAGA

AGTGATACCCATGTTTTCAGCATTATCAGAAGGAGCCACCCCACAAGATT

TAAACACCATGCTAAACACAGTGGGGGGACATCAAGCAGCCATGCAAATG

TTAAAAGAGACCATCAATGAGGAAGCTGCAGAATGGGATAGAGTGCATCC

AGTGCATGCAGGGCCTATTGCACCAGGCCAGATGAGAGAACCAAGGGGAA

GTGACATAGCAGGAACTACTAGTACCCTTCAGGAACAAATAGGATGGATG

ACACATAATCCACCTATCCCAGTAGGAGAAATCTATAAAAGATGGATAAT

CCTGGGATTAAATAAAATAGTAAGAATGTATAGCCCTACCAGGATTCTGG

ACATAAGACAAGGACCAAAGGAACCCTTTAGAGACTATGTAGACCGATTC

TATAAAACTCTAAGAGCCGAGCAAGCTTCACAAGAGGTAAAAAATTGGAT

GACAGAAACCTTGTTGGTCCAAAATGCGAACCCAGATTGTAAGACTATTT

TAAAAGCATTGGGACCAGGAGCGACACTAGAAGAAATGATGACAGCATGT

CAGGGAGTGGGGGGACCCGGCCATAAAGCAAGAGTTTTGGCTGAAGCAAT

GAGCCAAGTAACAAATCCAGCTACCATAATGATACAGAAAGGCAATTTTA

GGAACCAAAGAAAGACTGTTAAGTGTTTCAATTGTGGCAAAGAAGGGCAC

ATAGCCAAAAATTGCAGGGCCCCTAGGAAAAAGGGCTGTTGGAAATGTGG

AAAGGAAGGACACCAAATGAAAGATTGTACTGAGAGACAGGCTAATTTTT

TAGGGAAGATCTGGCCTTCCCACAAGGGAAGGCCAGGGAATTTTCTTCAG

AGCAGACCAGAGCCAACAGCCCCACCAGAAGAGAGCTTCAGGTTTGGGGA

-continued

AGAGACAACAACTCCCTCTCAGAAGCAGGAGCCGATAGACAAGGAACTGT
ATCCTTTAGCTTCCCTCAGATCACTCTTTGGCAGCGACCCCTCGTCACAA
TAA

HIV-1 Pol), (Seq ID No. 3).

TTTTTAGGGAAGATCTGGCCTTCCCACAAGGGAAGGCCAGGGAATTTTC
TTCAGAGCAGACCAGAGCCAACAGCCCCACCAGAAGAGAGCTTCAGGTTT
GGGGAAGAGACAACAACTCCCTCTCAGAAGCAGGAGCCGATAGACAAGGA
ACTGTATCCTTTAGCTTCCCTCAGATCACTCTTTGGCAGCGACCCCTCGT
CACAATAAAGATAGGGGGGCAATTAAAGGAAGCTCTATTAGATACAGGAG
CAGATGATACAGTATTAGAAGAAATGAATTTGCCAGGAAGATGGAAACCA
AAAATGATAGGGGGAATTGGAGGTTTTATCAAAGTAAGACAGTATGATCA
GATACTCATAGAAATCTGCGGACATAAAGCTATAGGTACAGTATTAGTAG
GACCTACACCTGTCAACATAATTGGAAGAAATCTGTTGACTCAGATTGGC
TGCACTTTAAATTTTCCCATTAGTCCTATTGAGACTGTACCAGTAAAATT
AAAGCCAGGAATGGATGGCCCAAAAGTTAAACAATGGCCATTGACAGAAG
AAAAAATAAAAGCATTAGTAGAAATTTGTACAGAAATGGAAAAGGAAGGA
AAAATTTCAAAAATTGGGCCTGAAAATCCATACAATACTCCAGTATTTGC
CATAAAGAAAAAAGACAGTACTAAATGGAGAAAATTAGTAGATTTCAGAG
AACTTAATAAGAGAACTCAAGATTTCTGGGAAGTTCAATTAGGAATACCA
CATCCTGCAGGGTTAAAACAGAAAAAATCAGTAACAGTACTGGATGTGGG
CGATGCATATTTTTCAGTTCCCTTAGATAAAGACTTCAGGAAGTATACTG
CATTTACCATACCTAGTATAAACAATGAGACACCAGGGATTAGATATCAG
TACAATGTGCTTCCACAGGGATGGAAAGGATCACCAGCAATATTCCAGTG
TAGCATGACAAAAATCTTAGAGCCTTTTAGAAAACAAAATCCAGACATAG
TCATCTATCAATACATGGATGATTTGTATGTAGGATCTGACTTAGAAATA
GGGCAGCATAGAACAAAAATAGAGGAACTGAGACAACATCTGTTGAGGTG
GGGATTTACCACACCAGACAAAAAACATCAGAAAGAACCTCCATTCCTTT
GGATGGGTTATGAACTCCATCCTGATAAATGGACAGTACAGCCTATAGTG
CTGCCAGAAAAGGACAGCTGGACTGTCAATGACATACAGAAATTAGTGGG
AAAATTGAATTGGGCAAGTCAGATTTATGCAGGGATTAAAGTAAGGCAAT
TATGTAAACTTCTTAGGGGAACCAAAGCACTAACAGAAGTAGTACCACTA
ACAGAAGAAGCAGAGCTAGAACTGGCAGAAAACAGGGAGATTCTAAAAGA
ACCGGTACATGGAGTGTATTATGACCCATCAAAAGACTTAATAGCAGAAA
TACAGAAGCAGGGGCAAGGCCAATGGACATATCAAATTTATCAAGAGCCA
TTTAAAAATCTGAAAACAGGAAAGTATGCAAGAATGAAGGGTGCCCACAC
TAATGATGTGAAACAATTAACAGAGGCAGTACAAAAAATAGCCACAGAAA
GCATAGTAATATGGGGAAAGACTCCTAAATTTAAATTACCCATACAAAAG
GAAACATGGGAAGCATGGTGGACAGAGTATTGGCAAGCCACCTGGATTCC
TGAGTGGGAGTTTGTCAATACCCCTCCCTTAGTGAAGTTATGGTACCAGT
TAGAGAAAGAACCCATAATAGGAGCAGAAACTTTCTATGTAGATGGGGCA
GCCAATAGGGAAACTAAATTAGGAAAAGCAGGATATGTAACTGACAGAGG
AAGACAAAAAGTTGTCCCCCTAACGGACACAACAAATCAGAAGACTGAGT
TACAAGCAATTCATCTAGCTTTGCAGGATTCGGGATTAGAAGTAAACATA
GTGACAGACTCACAATATGCATTGGGAATCATTCAAGCACAACCAGATAA
GAGTGAATCAGAGTTAGTCAGTCAAATAATAGAGCAGTTAATAAAAAAGG
AAAAAGTCTACCTGGCATGGGTACCAGCACACAAAGGAATTGGAGGAAAT
GAACAAGTAGATAAATTGGTCAGTGCTGGAATCAGGAAAGTACTATTTTT
AGATGGAATAGATAAGGCCCAAGAAGAACATGAGAAATATCACAGTAATT
GGAGAGCAATGGCTAGTGATTTTAACCTACCACCTGTAGTAGCAAAAGAA
ATAGTAGCCAGCTGTGATAAATGTCAGCTAAAAGGGGAAGCCATGCATGG
ACAAGTAGACTGTAGCCCAGGAATATGGCAGCTAGATTGTACACATTTAG
AAGGAAAAGTTATCTTGGTAGCAGTTCATGTAGCCAGTGGATATATAGAA
GCAGAAGTAATTCCAGCAGAGACAGGGCAAGAAACAGCATACTTCCTCTT
AAAATTAGCAGGAAGATGGCCAGTAAAAACAGTACATACAGACAATGGCA
GCAATTTCACCAGTACTACAGTTAAGGCCGCCTGTTGGTGGGCGGGGATC
AAGCAGGAATTTGGGATTCCCTACAATCCCCAAAGTCAAGGAGTAATAGA
ATCTATGAATAAAGAATTAAAGAAAATTATAGGACAGGTAAGAGATCAGG
CTGAACATCTTAAGACAGCAGTACAAATGGCAGTATTCATCCACAATTTT
AAAAGAAAAGGGGGGATTGGGGGGTACAGTGCAGGGGAAAGAATAGTAGA
CATAATAGCAACAGACATACAAACTAAAGAATTACAAAAACAAATTACAA
AAATTCAAAATTTTCGGGTTTATTACAGGGACAGCAGAGATCCAGTTTGG
AAAGGACCAGCAAAGCTCCTCTGGAAAGGTGAAGGGGCAGTAGTAATACA
AGATAATAGTGACATAAAAGTAGTGCCAAGAAGAAAAGCAAAGATCATCA
GGGATTATGGAAAACAGATGGCAGGTGATGATTGTGTGGCAAGTAGACAG
GATGAGGATTAA

HIV-1 Tat, (Seq ID No. 4).

ATGGAGCCAGTAGATCCTAGACTAGAGCCCTGGAAGCATCCAGGAAGTCA
GCCTAAAACTGCTTGTACCAATTGCTATTGTAAAAAGTGTTGCTTTCATT
GCCAAGTTTGTTTCATAACAAAAGCCTTAGGCATCTCCTATGGCAGGAAG
AAGCGGAGACAGCGACGAAGACCTCCTCAAGGCAGTCAGACTCATCAAGT
TTCTCTATCAAAGCAACCCACCTCCCAATCCCGAGGGGACCCGACAGGCC
CGAAGGAATAG

HIV-1 Vif, (Seq ID No. 5).

ATGGAAAACAGATGGCAGGTGATGATTGTGTGGCAAGTAGACAGGATGAG
GATTAACACATGGAAAAGATTAGTAAAACACCATATGTATATTTCAAGGA
AAGCTAAGGACTGGTTTTATAGACATCACTATGAAAGTACTAATCCAAAA
ATAAGTTCAGAAGTACACATCCCACTAGGGGATGCTAAATTAGTAATAAC
AACATATTGGGGTCTGCATACAGGAGAAAGAGACTGGCATTTGGGTCAGG
GAGTCTCCATAGAATGGAGGAAAAAGAGATATAGCACACAAGTAGACCCT
GACCTAGCAGACCAACTAATTCATCTGCACTATTTTGATTGTTTTTCAGA
ATCTGCTATAAGAAATACCATATTAGGACGTATAGTTAGTCCTAGGTGTG
AATATCAAGCAGGACATAACAAGGTAGGATCTCTACAGTACTTGGCACTA
GCAGCATTAATAAAACCAAAACAGATAAAGCCACCTTTGCCTAGTGTTAG

GAAACTGACAGAGGACAGATGGAACAAGCCCCAGAAGACCAAGGGCCACA

GAGGGAGCCATACAATGAATGGACACTAG

HIV-1 Env, (Seq ID No. 6).
ATGAGAGTGAAGGAGAAATATCAGCACTTGTGGAGATGGGGGTGGAGATG

GGGCACCATGCTCCTTGGGATGTTGATGATCTGTAGTGCTACAGAAAAAT

TGTGGGTCACAGTCTATTATGGGGTACCTGTGTGGAAGGAAGCAACCACC

ACTCTATTTTGTGCATCAGATGCTAAAGCATATGATACAGAGGTACATAA

TGTTTGGGCCACACATGCCTGTGTACCCACAGACCCCAACCCACAAGAAG

TAGTATTGGTAAATGTGACAGAAAATTTTAACATGTGGAAAAATGACATG

GTAGAACAGATGCATGAGGATATAATCAGTTTATGGGATCAAAGCCTAAA

GCCATGTGTAAAATTAACCCCACTCTGTGTTAGTTTAAAGTGCACTGATT

TGAAGAATGATACTAATACCAATAGTAGTAGCGGGAGAATGATAATGGAG

AAAGGAGAGATAAAAAACTGCTCTTTCAATATCAGCACAAGCATAAGAGG

TAAGGTGCAGAAAGAATATGCATTTTTTTATAAACTTGATATAATACCAA

TAGATAATGATACTACCAGCTATACGTTGACAAGTTGTAACACCTCAGTC

ATTACACAGGCCTGTCCAAAGGTATCCTTTGAGCCAATTCCCATACATTA

TTGTGCCCCGGCTGGTTTTGCGATTCTAAAATGTAATAATAAGACGTTCA

ATGGAACAGGACCATGTACAAATGTCAGCACAGTACAATGTACACATGGA

ATTAGGCCAGTAGTATCAACTCAACTGCTGTTAAATGGCAGTCTAGCAGA

AGAAGAGGTAGTAATTAGATCTGTCAATTTCACGGACAATGCTAAAACCA

TAATAGTACAGCTGAACACATCTGTAGAAATTAATTGTACAAGACCCAAC

AACAATACAAGAAAAAAAATCCGTATCCAGAGGGGACCAGGGAGAGCATT

TGTTACAATAGGAAAAATAGGAAATATGAGACAAGCACATTGTAACATTA

GTAGAGCAAAATGGAATGCCACTTTAAAACAGATAGCTAGCAAATTAAGA

GAACAATTTGGAAATAATAAAACAATAATCTTTAAGCAATCCTCAGGAGG

GGACCCAGAAATTGTAACGCACAGTTTTAATTGTGGAGGGGAATTTTTCT

ACTGTAATTCAACACAACTGTTTAATAGTACTTGGTTTAATAGTACTTGG

AGTACTGAAGGGTCAAATAACACTGAAGGAAGTGACACAATCACACTCCC

ATGCAGAATAAAACAATTTATAAACATGTGGCAGGAAGTAGGAAAAGCAA

TGTATGCCCCTCCCRTCAGCGGACAAATTAGATGTTCATCAAATATTACA

GGGCTGCTATTAACAAGAGATGGTGGTAATAACAACAATGGGTCCGAGAT

CTTCAGACCTGGAGGAGGAGATATGAGGGACAATTGGAGAAGTGAATTAT

ATAAATATAAAGTAGTAAAAATTGAACCATTAGGAGTAGCACCCACCAAG

GCAAAGAGAAGAGTGGTGCAGAGAGAAAAAAGAGCAGTGGGAATAGGAGC

TTTGTTCCTTGGGTTCTTGGGAGCAGCAGGAAGCACTATGGGCGCAGCGT

CAATGACGCTGACGGTACAGGCCAGACAATTATTGTCTGGTATAGTGCAG

CAGCAGAACAATTTGCTGAGGGCTATTGAGGCGCAACAGCATCTGTTGCA

ACTCACAGTCTGGGGCATCAAGCAGCTCCAGGCAAGAATCCTGGCTGTGG

AAAGATACCTAAAGGATCAACAGCTCCTGGGGATTTGGGGTTGCTCTGGA

AAACTCATTTGCACCACTGCTGTGCCTTGGAATGCTAGTTGGAGTAATAA

ATCTCTGGAACAGATTTGGAATCACACGACCTGGATGGAGTGGGACAGAG

AAATTAACAATTACACAAGCTTAATACACTCCTTAATTGAAGAATCGCAA

AACCAGCAAGAAAAGAATGAACAAGAATTATTGGAATTAGATAAATGGGC

AAGTTTGTGGAATTGGTTTAACATAACAAATTGGCTGTGGTATATAAAAT

TATTCATAATGATAGTAGGAGGCTTGGTAGGTTTAAGAATAGTTTTTGCT

GTACTTTCTGTAGTGAATAGAGTTAGGCAGGGATATTCACCATTATCGTT

TCAGACCCACCTCCCAATCCCGAGGGGACCCGACAGGCCCGAAGGAATAG

AAGAAGAAGGTGGAGAGAGAGACAGAGACAGATCCATTCGATTAGTGAAC

GGATCCTTAGCACTTATCTGGGACGATCTGCGGAGCCTGTGCCTCTTCAG

CTACCACCGCTTGAGAGACTTACTCTTGATTGTAACGAGGATTGTGGAAC

TTCTGGGACGCAGGGGGTGGGAAGCCCTCAAATATTGGTGGAATCTCCTA

CAATATTGGAGTCAGGAGCTAAAGAATAGTGCTGTTAGCTTGCTCAATGC

CACAGCTATAGCAGTAGCTGAGGGGACAGATAGGGTTATAGAAGTAGTAC

AAGAAGCTTATAGAGCTATTCGCCACATACCTAGAAGAATAGGACAGGGC

TTGGAAAGGATTTTGCTATAA

HIV-1 genome, (Sequ ID No. 7).
GGTCTCTCTGGTTAGACCAGATCTGAGCCTGGGAGCTCTCTGGCTAACTA

GGGAACCCACTGCTTAAGCCTCAATAAAGCTTGCCTTGAGTGCTTCAAGT

AGTGTGTGCCCGTCTGTTGTGTGACTCTGGTAACTAGAGATCCCTCAGAC

CCTTTTAGTCAGTGTGGAAAATCTCTAGCAGTGGCGCCCGAACAGGGACA

TGAAAGCGAAAGGGAAACCAGAGGAGCTCTCTCGACGCAGGACTCGGCTT

GCTGAAGCGCGCACGGCAAGAGGCGAGGGGCGGCGACTGGTGAGTACGCC

AAAAATTTTGACTAGCGGAGGCTAGAAGGAGAGAGATGGGTGCGAGAGCG

TCAGTATTAAGCGGGGGAAAATTAGATCGATGGGAAAAAATTCGGTTAAG

GCCAGGGGGAAAGAAAAAATATAAATTAAAACATATAGTATGGGCAAGCA

GGGAGCTAGAACGATTCGCAGTTAATCCTGGCCTGTTAGAAACATCAGAA

GGCTGTAGACAAATACTGGGACAGCTACAACCATCCCTTCAGACAGGATC

AGAAGAACGTAGATCATTATATAATACAGTAGCAACCCTCTATTGTGTGC

ATCAAAGGATAGAGATAAAAGACACCAAGGAAGCTTTAGACAAGATAGAG

GAAGAGCAAAACAAAAGTAAGAAAAAAGCACAGCAAGCAGCAGCTGACAC

AGGACACAGCAGCCAGGTCAGCCAAAATTACCCTATAGTGCAGAACATCC

AGGGGCAAATGGTACATCAGGCCATATCACCTAGAACTTTAAATGCATGG

GTAAAAGTAGTAGAAGAGAAGGCTTTCAGCCCAGAAGTGATACCCATGTT

TTCAGCATTATCAGAAGGAGCCACCCCACAAGATTTAAACACCATGCTAA

ACACAGTGGGGGGACATCAAGCAGCCATGCAAATGTTAAAAGAGACCATC

AATGAGGAAGCTGCAGAATGGGATAGAGTGCATCCAGTGCATGCAGGGCC

TATTGCACCAGGCCAGATGAGAGAACCAAGGGGAAGTGACATAGCAGGAA

CTACTAGTACCCTTCAGGAACAAATAGGATGGATGACACATAATCCACCT

ATCCCAGTAGGAGAAATCTATAAAAGATGGATAATCCTGGGATTAAATAA

AATAGTAAGAATGTATAGCCCTACCAGCATTCTGGACATAAGACAAGGAC

CAAAGGAACCCTTTAGAGACTATGTAGACCGATTCTATAAAACTCTAAGA

GCCGAGCAAGCTTCACAAGAGGTAAAAAATTGGATGACAGAAACCTTGTT

-continued

GGTCCAAAATGCGAACCCAGATTGTAAGACTATTTTAAAAGCATTGGGAC

CAGGAGCGACACTAGAAGAAATGATGACAGCATGTCAGGGAGTGGGGGGA

CCCGGCCATAAAGCAAGAGTTTTGGCTGAAGCAATGAGCCAAGTAACAAA

TCCAGCTACCATAATGATACAGAAAGGCAATTTTAGGAACCAAAGAAAGA

CTGTTAAGTGTTTCAATTGTGGCAAAGAAGGGCACATAGCCAAAAATTGC

AGGGCCCCTAGGAAAAAGGGCTGTTGGAAATGTGGAAAGGAAGGACACCA

AATGAAAGATTGTACTGAGAGACAGGCTAATTTTTTAGGGAAGATCTGGC

CTTCCCACAAGGGAAGGCCAGGGAATTTTCTTCAGAGCAGACCAGAGCCA

ACAGCCCCACCAGAAGAGAGCTTCAGGTTTGGGGAAGAGACAACAACTCC

CTCTCAGAAGCAGGAGCCGATAGACAAGGAACTGTATCCTTTAGCTTCCC

TCAGATCACTCTTTGGCAGCGACCCCTCGTCACAATAAAGATAGGGGGGC

AATTAAAGGAAGCTCTATTAGATACAGGAGCAGATGATACAGTATTAGAA

GAAATGAATTTGCCAGGAAGATGGAAACCAAAAATGATAGGGGGAATTGG

AGGTTTTATCAAAGTAAGACAGTATGATCAGATACTCATAGAAATCTGCG

GACATAAAGCTATAGGTACAGTATTAGTAGGACCTACACCTGTCAACATA

ATTGGAAGAAATCTGTTGACTCAGATTGGCTGCACTTTAAATTTTCCCAT

TAGTCCTATTGAGACTGTACCAGTAAAATTAAAGCCAGGAATGGATGGCC

CAAAAGTTAAACAATGGCCATTGACAGAAGAAAAAATAAAAGCATTAGTA

GAAATTTGTACAGAAATGGAAAAGGAAGGAAAAATTTCAAAAATTGGGCC

TGAAAATCCATACAATACTCCAGTATTTGCCATAAAGAAAAAAGACAGTA

CTAAATGGAGAAAATTAGTAGATTTCAGAGAACTTAATAAGAGAACTCAA

GATTTCTGGGAAGTTCAATTAGGAATACCACATCCTGCAGGGTTAAAACA

GAAAAAATCAGTAACAGTACTGGATGTGGGCGATGCATATTTTTCAGTTC

CCTTAGATAAAGACTTCAGGAAGTATACTGCATTTACCATACCTAGTATA

AACAATGAGACACCAGGGATTAGATATCAGTACAATGTGCTTCCACAGGG

ATGGAAAGGATCACCAGCAATATTCCAGTGTAGCATGACAAAAATCTTAG

AGCCTTTTAGAAAACAAAATCCAGACATAGTCATCTATCAATACATGGAT

GATTTGTATGTAGGATCTGACTTAGAAATAGGGCAGCATAGAACAAAAAT

AGAGGAACTGAGACAACATCTGTTGAGGTGGGGATTTACCACACCAGACA

AAAAACATCAGAAAGAACCTCCATTCCTTTGGATGGGTTATGAACTCCAT

CCTGATAAATGGACAGTACAGCCTATAGTGCTGCCAGAAAAGGACAGCTG

GACTGTCAATGACATACAGAAATTAGTGGGAAAATTGAATTGGGCAAGTC

AGATTTATGCAGGGATTAAAGTAAGGCAATTATGTAAACTTCTTAGGGGA

ACCAAAGCACTAACAGAAGTAGTACCACTAACAGAAGAAGCAGAGCTAGA

ACTGGCAGAAAACAGGGAGATTCTAAAAGAACCGGTACATGGAGTGTATT

ATGACCCATCAAAAGACTTAATAGCAGAAATACAGAAGCAGGGGCAAGGC

CAATGGACATATCAAATTTATCAAGAGCCATTTAAAAATCTGAAAACAGG

AAAGTATGCAAGAATGAAGGGTGCCCACACTAATGATGTGAAACAATTAA

CAGAGGCAGTACAAAAAATAGCCACAGAAAGCATAGTAATATGGGGAAAG

ACTCCTAAATTTAAATTACCCATACAAAAGGAAACATGGGAAGCATGGTG

-continued

GACAGAGTATTGGCAAGCCACCTGGATTCCTGAGTGGGAGTTTGTCAATA

CCCCTCCCTTAGTGAAGTTATGGTACCAGTTAGAGAAAGAACCCATAATA

GGAGCAGAAACTTTCTATGTAGATGGGGCAGCCAATAGGGAAACTAAATT

AGGAAAAGCAGGATATGTAACTGACAGAGGAAGACAAAAAGTTGTCCCCC

TAACGGACACAACAAATCAGAAGACTGAGTTACAAGCAATTCATCTAGCT

TTGCAGGATTCGGGATTAGAAGTAAACATAGTGACAGACTCACAATATGC

ATTGGGAATCATTCAAGCACAACCAGATAAGAGTGAATCAGAGTTAGTCA

GTCAAATAATAGAGCAGTTAATAAAAAAGGAAAAAGTCTACCTGGCATGG

GTACCAGCACACAAAGGAATTGGAGGAAATGAACAAGTAGATAAATTGGT

CAGTGCTGGAATCAGGAAAGTACTATTTTTAGATGGAATAGATAAGGCCC

AAGAAGAACATGAGAAATATCACAGTAATTGGAGAGCAATGGCTAGTGAT

TTTAACCTACCACCTGTAGTAGCAAAAGAAATAGTAGCCAGCTGTGATAA

ATGTCAGCTAAAAGGGGAAGCCATGCATGGACAAGTAGACTGTAGCCCAG

GAATATGGCAGCTAGATTGTACACATTTAGAAGGAAAAGTTATCTTGGTA

GCAGTTCATGTAGCCAGTGGATATATAGAAGCAGAAGTAATTCCAGCAGA

GACAGGGCAAGAAACAGCATACTTCCTCTTAAAATTAGCAGGAAGATGGC

CAGTAAAAACAGTACATACAGACAATGGCAGCAATTTCACCAGTACTACA

GTTAAGGCCGCCTGTTGGTGGGCGGGGATCAAGCAGGAATTTGGCATTCC

CTACAATCCCCAAAGTCAAGGAGTAATAGAATCTATGAATAAAGAATTAA

AGAAAATTATAGGACAGGTAAGAGATCAGGCTGAACATCTTAAGACAGCA

GTACAAATGGCAGTATTCATCCACAATTTTAAAAGAAAAGGGGGGATTGG

GGGGTACAGTGCAGGGGAAAGAATAGTAGACATAATAGCAACAGACATAC

AAACTAAAGAATTACAAAAACAAATTACAAAAATTCAAAATTTCGGGTTT

ATTACAGGGACAGCAGAGATCCAGTTTGGAAAGGACCAGCAAAGCTCCTC

TGGAAAGGTGAAGGGGCAGTAGTAATACAAGATAATAGTGACATAAAAGT

AGTGCCAAGAAGAAAAGCAAAGATCATCAGGGATTATGGAAAACAGATGG

CAGGTGATGATTGTGTGGCAAGTAGACAGGATGAGGATTAACACATGGAA

AAGATTAGTAAAACACCATATGTATATTTCAAGGAAAGCTAAGGACTGGT

TTTATAGACATCACTATGAAAGTACTAATCCAAAAATAAGTTCAGAAGTA

CACATCCCACTAGGGGATGCTAAATTAGTAATAACAACATATTGGGGTCT

GCATACAGGAGAAAGAGACTGGCATTTGGGTCAGGGAGTCTCCATAGAAT

GGAGGAAAAAGAGATATAGCACACAAGTAGACCCTGACCTAGCAGACCAA

CTAATTCATCTGCACTATTTTGATTGTTTTTCAGAATCTGCTATAAGAAA

TACCATATTAGGACGTATAGTTAGTCCTAGGTGTGAATATCAAGCAGGAC

ATAACAAGGTAGGATCTCTACAGTACTTGGCACTAGCAGCATTAATAAAA

CCAAAACAGATAAAGCCACCTTTGCCTAGTGTTAGGAAACTGACAGAGGA

CAGATGGAACAAGCCCCAGAAGACCAAGGGCCACAGAGGGAGCCATACAA

TGAATGGACACTAGAGCTTTTAGAGGAACTTAAGAGTGAAGCTGTTAGAC

ATTTTCCTAGGATATGGCTCCATAACTTAGGACAACATATCTATGAAACT

TACGGGGATACTTGGGCAGGAGTGGAAGCCATAATAAGAATTCTGCAACA

ACTGCTGTTTATCCATTCAGAATTGGGTGTCGACATAGCAGAATAGGCGT

-continued

```
TACTCGACAGAGGAGAGCAAGAAATGGAGCCAGTAGATCCTAGACTAGAG
CCCTGGAAGCATCCAGGAAGTCAGCCTAAAACTGCTTGTACCAATTGCTA
TTGTAAAAAGTGTTGCTTTCATTGCCAAGTTTGTTTCATAACAAAAGCCT
TAGGCATCTCCTATGGCAGGAAGAAGCGGAGACAGCGACGAAGACCTCCT
CAAGGCAGTCAGACTCATCAAGTTTCTCTATCAAAGCAGTAAGTAATACA
TGTAATGCAACCTATACAAATAGCAATAGTAGCATTAGTAGTAGCAATAA
TAATAGCAATAGTTGTGTGGTCCATAGTAATCATAGAATATAGGAAAATA
TTAAGACAAAGAAAAATAGACAGGTTAATTGATAGACTAATAGAAAGAGC
AGAAGACAGTGGCAATGAGAGTGAAGGAGAAATATCAGCACTTGTGGAGA
TGGGGGTGGAGATGGGGCACCATGCTCCTTGGGATGTTGATGATCTGTAG
TGCTACAGAAAAATTGTGGGTCACAGTCTATTATGGGGTACCTGTGTGGA
AGGAAGCAACCACCACTCTATTTTGTGCATCAGATGCTAAAGCATATGAT
ACAGAGGTACATAATGTTTGGGCCACACATGCCTGTGTACCCACAGACCC
CAACCCACAAGAAGTAGTATTGGTAAATGTGACAGAAAATTTTAACATGT
GGAAAAATGACATGGTAGAACAGATGCATGAGGATATAATCAGTTTATGG
GATCAAAGCCTAAAGCCATGTGTAAAATTAACCCCACTCTGTGTTAGTTT
AAAGTGCACTGATTTGAAGAATGATACTAATACCAATAGTAGTAGCGGGA
GAATGATAATGGAGAAAGGAGAGATAAAAAACTGCTCTTTCAATATCAGC
ACAAGCATAAGAGGTAAGGTGCAGAAAGAATATGCATTTTTTATAAACTT
GATATAATACCAATAGATAATGATACTACCAGCTATACGTTGACAAGTTG
TAACACCTCAGTCATTACACAGGCCTGTCCAAAGGTATCCTTTGAGCCAA
TTCCCATACATTATTGTGCCCCGGCTGGTTTTGCGATTCTAAAATGTAAT
AATAAGACGTTCAATGGAACAGGACCATGTACAAATGTCAGCACAGTACA
ATGTACACATGGAATTAGGCCAGTAGTATCAACTCAACTGCTGTTAAATG
GCAGTCTAGCAGAAGAAGAGGTAGTAATTAGATCTGTCAATTTCACGGAC
AATGCTAAAACCATAATAGTACAGCTGAACACATCTGTAGAAATTAATTG
TACAAGACCCAACAACAATACAAGAAAAAAAATCCGTATCCAGAGGGGAC
CAGGGAGAGCATTTGTTACAATAGGAAAAATAGGAAATATGAGACAAGCA
CATTGTAACATTAGTAGAGCAAAATGGAATGCCACTTTAAAACAGATAGC
TAGCAAATTAAGAGAACAATTTGGAAATAATAAAACAATAATCTTTAAGC
AATCCTCAGGAGGGGACCCAGAAATTGTAACGCACAGTTTTAATTGTGGA
GGGGAATTTTTCTACTGTAATTCAACACAACTGTTTAATAGTACTTGGTT
TAATAGTACTTGGAGTACTGAAGGGTCAAATAACACTGAAGGAAGTGACA
CAATCACACTCCCATGCAGAATAAAACAATTTATAAACATGTGGCAGGAA
GTAGGAAAAGCAATGTATGCCCCTCCCATCAGCGGACAAATTAGATGTTC
ATCAAATATTACAGGGCTGCTATTAACAAGAGATGGTGGTAATAACAACA
ATGGGTCCGAGATCTTCAGACCTGGAGGAGGAGATATGAGGGACAATTGG
AGAAGTGAATTATATAAATATAAAGTAGTAAAAATTGAACCATTAGGAGT
AGCACCCACCAAGGCAAAGAGAAGAGTGGTGCAGAGAGAAAAAAGAGCAG
TGGGAATAGGAGCTTTGTTCCTTGGGTTCTTGGGAGCAGCAGGAAGCACT
ATGGGCGCAGCGTCAATGACGCTGACGGTACAGGCCAGACAATTATTGTC
TGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGA
ATCCTGGCTGTGGAAAGATACCTAAAGGATCAACAGCTCCTGGGGATTTG
GGGTTGCTCTGGAAAACTCATTTGCACCACTGCTGTGCCTTGGAATGCTA
GTTGGAGTAATAAATCTCTGGAACAGATTTGGAATCACACGACCTGGATG
GAGTGGGACAGAGAAATTAACAATTACACAAGCTTAATACACTCCTTAAT
TGAAGAATCGCAAAACCAGCAAGAAAAGAATGAACAAGAATTATTGGAAT
TAGATAAATGGGCAAGTTTGTGGAATTGGTTTAACATAACAAATTGGCTG
TGGTATATAAAATTATTCATAATGATAGTAGGAGGCTTGGTAGGTTTAAG
AATAGTTTTTGCTGTACTTTCTGTAGTGAATAGAGTTAGGCAGGGATATT
CACCATTATCGTTTCAGACCCACCTCCCAATCCCGAGGGGACCCGACAGG
CCCGAAGGAATAGAAGAAGAAGGTGGAGAGAGAGACAGAGACAGATCCAT
TCGATTAGTGAACGGATCCTTAGCACTTATCTGGGACGATCTGCGGAGCC
TGTGCCTCTTCAGCTACCACCGCTTGAGAGACTTACTCTTGATTGTAACG
AGGATTGTGGAACTTCTGGGACGCAGGGGGTGGGAAGCCCTCAAATATTG
GTGGAATCTCCTACAATATTGGAGTCAGGAGCTAAAGAATAGTGCTGTTA
GCTTGCTCAATGCCACAGCTATAGCAGTAGCTGAGGGGACAGATAGGGTT
ATAGAAGTAGTACAAGAAGCTTATAGAGCTATTCGCCACATACCTAGAAG
AATAGGACAGGGCTTGGAAAGGATTTTGCTATAAGATGGGTGGCAAGTGG
TCAAAAAGTAGTGTGGTTGGATGGCCTGCTGTAAGGGAAAGAATGAGACG
AGCTGAGCCAGCAGCAGATGGGGTGGGAGCAGCATCTCGAGACCTAGAAA
AACATGGAGCAATCACAAGTAGCAACACAGCAGCTAACAATGCTGCTTGT
GCCTGGCTAGAAGCACAAGAGGAGGAGAAGGTGGGTTTTCCAGTCACACC
TCAGGTACCTTTAAGACCAATGACTTACAAGGCAGCTGTAGATCTTAGCC
ACTTTTTAAAAGAAAAGGGGGGACTGGAAGGGCTAATTCACTCCCAACGA
AGACAAGATATCCTTGATCTGTGGATCTACCACACACAAGGCTACTTCCC
TGATTGGCAGAACTACACACCAGGACCAGGGATCAGATATCCACTGACCT
TTGGATGGCGCTACAAGCTAGTACCAGTTGAGCCAGAGAAGTTAGAAGAA
GCCAACAAAGGAGAGAACACCAGCTTGTTACACCCTGTGAGCCTGCATGG
AATGGATGACCCGGAGAGAGAAGTGTTAGAGTGGAGGTTTGACAGCCGCC
TAGCATTTCATCACGTGGCCCGAGAGCTGCATCCGGAGTACTTCAAGAAC
TGCTGATATCGAGCTTGCTACAAGGGACTTTCCGCTGGGGACTTTCCAGG
GAGGCGTGGCCTGGGCGGGACTGGGGAGTGGCGAGCCCTCAGATCCTGCA
TATAAGCAGCTGCTTTTTGCCTGTACTGGGTCTCTCTGGTTAGACCAGAT
CTGAGCCTGGGAGCTCTCTGGCTAACTAGGGAACCCACTGCTTAAGCCTC
AATAAAGCTTGCCTTGAGTGCTTCAAGTAGTGTGTGCCCGTCTGTTGTGT
GACTCTGGTAACTAGAGATCCCTCAGACCCTTTTAGTCAGTGTGGAAAAT
CTCTAGCAGT
```

Exemplary nucleotide sequences encoding human CCR5 can also be found, e.g., in Samson et al. Biochemistry 35:3362-3367(1996), Raport et al. J. Biol. Chem. 271:

17161-17166(1996); Combadiere et al. J. Leukoc. Biol. 60:147-152(1996); Zhang et al. AIDS Res. Hum. Retroviruses 13:1357-1366(1997), the contents of which are herein specifically incorporated by reference in its entirety.

Exemplary nucleotide sequences encoding HIV (e.g., HIV-1) Gap Env, Tat, Pol2, Pol1, or Vif can also be found in HIV Sequence Compendium 2013 Foley B, Leitner T, Apetrei C, Hahn B, Mizrachi I, Mullins J, Rambaut A, Wolinsky S, and Korber B, Eds. Published by Theoretical Biology and Biophysics Group, Los Alamos National Laboratory, NM, LA-UR 13-26007, the contents of which are herein specifically incorporated by reference in its entirety Exemplary Modified Pri-miRNA-Like Molecules The nucleotide sequences of the exemplary modified pri-miRNA-like molecules are shown in Table 4 (Seq ID No. 8, Seq ID No. 9, Seq ID No. 10, Seq ID No. 11, Seq ID No. 12, Seq ID No. 13, Seq ID No. 14), with the mature siRNA sequences are shown in bold. The exemplary 5' flanking region, guide strand, terminal loop region, passenger strand, and 3' flanking region sequences are summarized in Table 5 (Seq ID No. 15, Seq ID No. 16, Seq ID No. 17, Seq ID No. 18, Seq ID No. 19, Seq ID No. 20, Seq ID No. 21, Seq ID No. 22, Seq ID No. 23, Seq ID No. 24, Seq ID No. 25, Seq ID No. 26, Seq ID No. 27, Seq ID No. 28, Seq ID No. 29, Seq ID No. 30, Seq ID No. 31, Seq ID No. 32, Seq ID No. 33, Seq ID No. 34, Seq ID No. 35, Seq ID No. 36, Seq ID No. 37, Seq ID No. 38, Seq ID No. 39, Seq ID No. 40, Seq ID No. 42, Seq ID No. 42, Seq ID No. 43, Seq ID No. 44, Seq ID No. 45, Seq ID No. 46, Seq ID No. 47, Seq ID No. 48, and Seq ID No. 49).

TABLE 4

| | |
|---|---|
| CCR5-miR-30a | AGGUAUAUUGCUGUUGACAGUGAGCGAC**UGUAAACUGAGCUUGCUCUACU**GUGAAGCCACAGAUGGG**UAGAGCAAGCACAGUUUACC**GCUGCCUACUGCCUCGGACUUCAAGGGGCUUGCGGCCGC |
| Gag-miR-21 | CAUCUCCAUGGCUGUACCACCUUGUCGG**CCUGCUAUGUCACUUCCCCUAC**UGUUGAAUCUCAUGG**AGGGGAAGUGCCAUAGCAGC**UCUGACAUUUUGGUAUCUUUCAUCUGACCA |
| Pol-1-miR-185 | GGGCCUGGCUCGAGCAGGGGGCGAGGGAU**UGACUUUGGGGAUUGUAGGGGA**UGGUCCCCUCCCC**CCCUACAAUCGCCAAAGUC**CGUCCUUCCCUCCCAAUGACCGCGUCUUCGUC |
| Vif-miR-150 | CAGCGGCGGCUCCUCUCCCCAUGGCCCUG**GGGAUGUGUACUUCUGAACUUG**CUGGGCUCAGACC**AGUUCAGAAGAACACAUCCG**CAGGGACCUGGGGACCCCGGCACCGGCAGGCC |
| Env-miR-20a | CUCUAUCUGAUGUGACAGCUUCUGUAGCAC**UUCUUCUGCUAGACUGCCAUAG**UGUUUAGUUAUCU**AUGGCAGUCUCGCAGAAGAC**GUACUGCUAGCUGUAGAACUCCAGCUUCGGCCUU |
| Tat-miR-16-1 | AACUUAUGAUAGCAAUGUCAGCAGUGCCUUCCGCUUCUUCCUGCCAUAGCGUUAAGAUUCUAAAAUUAU**CUCUAUGGCAGGCAGAAGCGGC**AAGUAAGGUUGACCAUACUCUACAGUUGUU |
| Pol2-miR-122 | UUCGUGGCUACAGAGUUUCCUUAGCAGAGCUGUAUCAUCUGCUCCUGUAUCUUGUGUUAAACUAUCA**AGAUACAGGACCAGAUGAUC**UAGCUACUGCUAGGCAAUCCUUCCCUCGAUAAAUG |

TABLE 5

| Modified pri-miRNA-like Molecule | 5' flanking region | Guide strand | Terminal loop region | Passenger strand | 3' flanking region |
|---|---|---|---|---|---|
| CCR5-miR-30a | AGGUAUAUUGCUGUUGACAGUGAGCGAC | **UGUAAACUGAGCUUGCUCUACU** | GUGAAGCCACAGAUGGGGCUGCCUACUGCC | **UAGAGCAAGCACAGUUUACC** | UCGGACUUCAAGGGGCUUGCGGCCGC |
| Gag-miR-21 | CAUCUCCAUGGCUGUACCACCUUGUCGG | **CCUGCUAUGUCACUUCCCCUAC** | UGUUGAAUCUCAUGG | **AGGGGAAGUGCCAUAGCAGC** | UCUGACAUUUUGGUAUCUUUCAUCUGACCA |
| Pol 1-MiR-185 | GGGCCUGGCUCGAGCAGGGGGCGAGGGAU | **UGACUUUGGGGAUUGUAGGGGA** | UGGUCCCCUCCCC | **CCCUACAAUCGCCAAAGUC** | CGUCCUUCCCUCCCAAUGACCGCGUCUUCGUC |
| Vif-miR-150 | CAGCGGCGGCUCCUCUCCCCAUGGCCCUG | **GGGAUGUGUACUUCUGAACUUG** | CUGGGCUCAGACC | **AGUUCAGAAGAACACAUCCG** | CAGGGACCUGGGGACCCCGGCACCGGCAGGCC |
| Env-miR-20a | CUCUAUCUGAUGUGACAGCUUCUGUAGCAC | **UUCUUCUGCUAGACUGCCAUAG** | UGUUUAGUUAUCU | **AUGGCAGUCUCGCAGAAGAC** | GUACUGCUAGCUGUAGAACUCCAGCUUCGGCCUU |
| Tat-miR-16- | AACUUAUGAUAGCAAUGUCAGCAGUGCCU | **UCCGCUUCUUCCUGCCAUAGCG** | UUAAGAUUCUAAAAUUAUCU | **CUAUGGCAGGCAGAAGCGGC** | AAGUAAGGUUGACCAUACUCUACAGUUGUU |

TABLE 5-continued

| Modified pri-miRNA-like Molecule | 5' flanking region | Guide strand | Terminal loop region | Passenger strand | 3' flanking region |
|---|---|---|---|---|---|
| Pol2-miR-122 | UUCGUGGCUACAGAGUUUCCUUAGCAGAGCUG | **UAUCAUCUGCUCCUGUAUCUUG** | UGUCUAAACUAUCA | **AGAUACAGGACCAGAUGAUC** | UAGCUACUGCUAGGCAAUCCUUCCCUCGAUAAAUG |

Pharmaceutical Compositions and Kits

This disclosure provides compositions, e.g., pharmaceutical compositions, which can include a nucleic acid molecule (e.g., an shRNA cluster or artificial miRNA cluster), an artificial RNA molecule (e.g., RNAi molecule), a cell, or a viral particle, as described herein, formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable, e.g., for intravenous, intramuscular, subcutaneous, parenteral, rectal, spinal, or epidermal administration (e.g., by injection or infusion). In certain embodiments, the shRNA clusters, nucleic acid molecules (e.g., artificial miRNA molecules), artificial RNA molecules (e.g., RNAi molecules), cells, or viral particles are at least about 90%, e.g., at least about 95%, 96%, 97%, 98%, 99%, 99.5%, or 99.9% pure in the pharmaceutical composition.

The compositions, e.g., pharmaceutical compositions, described herein may include a "therapeutically effective amount", "prophylactically effective amount", or "diagnostically effectively amount" of shRNA clusters, nucleic acid molecules (e.g., artificial miRNA clusters), cells, or viral particles.

A "therapeutically effective amount" refers to an amount effective, at dosages and for periods of time necessary, to achieve the desired therapeutic result. A therapeutically effective amount of nucleic acid molecule (e.g., shRNA cluster or artificial miRNA cluster), artificial RNA molecule (e.g., RNAi molecule), cell, or viral particle may vary according to factors such as the disease state, age, sex, and weight of the individual, and the ability of the antibody or antibody portion to elicit a desired response in the individual. A therapeutically effective amount is also one in which any toxic or detrimental effects of nucleic acid molecule (e.g., shRNA cluster or artificial miRNA cluster), cell, or viral particle is outweighed by the therapeutically beneficial effects. A "therapeutically effective dosage" typically inhibits a measurable parameter by at least about 20%, e.g., by at least about 40%, by at least about 60%, or by at least about 80% relative to untreated subjects. The measurable parameter may be, e.g., viral load, fever, headache, muscle or joint pains, skin rash, bleeding, reduced platelet levels, and reduced blood pressure. The ability of a nucleic acid molecule (e.g., shRNA cluster or artificial miRNA cluster), cell, or viral particle to inhibit a measurable parameter can be evaluated in an animal model system predictive of efficacy in reducing, inhibiting, or preventing an HIV infection. Alternatively, this property of a composition can be evaluated by examining the ability of a nucleic acid molecule (e.g., shRNA cluster or artificial miRNA cluster), cell, or viral particle to inhibit or reduce the viability of HIV, e.g., by an in vitro assay described herein.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A "diagnostically effective amount" refers to an amount effective, at dosages and for periods of time necessary, to achieve the desired diagnostic result. Typically, a diagnostically effective amount is one in which a disorder (e.g., an HIV infection or AIDS) can be diagnosed in vitro, ex vivo, or in vivo.

Also within this disclosure is a kit that comprises a nucleic acid molecule (e.g., shRNA cluster or artificial miRNA cluster), artificial RNA molecule (e.g., RNAi molecule), cell, or viral particle, described herein. The kit can include one or more other elements including: instructions for use; other reagents, e.g., a label (e.g., a radioactive label), a therapeutic agent, or an agent useful for chelating, or otherwise coupling, nucleic acid molecule (e.g., shRNA cluster or artificial miRNA cluster), artificial RNA molecule (e.g., RNAi molecule), cell, viral particle; devices or other materials for preparing the nucleic acid molecule (e.g., shRNA cluster or artificial miRNA cluster), artificial RNA molecule (e.g., RNAi molecule), cell, or viral particle for administration; pharmaceutically acceptable carriers; and devices or other materials for administration to a subject.

Methods of Treatment or Prevention

The disclosure provides methods for inhibiting HIV infection, e.g., using a nucleic acid molecule (e.g., shRNA cluster or artificial miRNA cluster), artificial RNA molecules (e.g., RNAi molecules), cell, or viral particle, as described herein. The disclosure also provides methods for treating or preventing HIV infection and/or AIDS, e.g., using a nucleic acid molecule (e.g., shRNA cluster or artificial miRNA cluster), artificial RNA molecule (e.g., RNAi molecule), cell, or viral particle, as described herein.

A nucleic acid molecule (e.g., shRNA cluster or artificial miRNA cluster), cell, or viral particle, as described herein, can be formulated for in vivo administration to a subject, such as a human or veterinary subject. A composition so formulated can comprise a nucleic acid molecule (e.g., shRNA cluster or artificial miRNA cluster), cell, or viral particle, as described herein, designed to express artificial RNA molecules (e.g., RNAi molecules) to decrease the expression of a target gene, e.g., a target gene described herein. A composition can also comprise a pharmaceutically acceptable excipient.

For example, artificial RNA molecules can be reliably expressed in vivo in a variety of cell types. In some embodiments, a nucleic acid molecule (e.g., shRNA cluster or artificial miRNA cluster) expressing an artificial RNA molecule is introduced (e.g., transduced or transfected) into a cell, e.g., a cell isolated from a subject. In certain embodiments, the transduced or transfected cell is administered to the subject in order to treat a condition. There are a variety of mechanisms by which transduced or transfected cells can be useful for treating HIV and AIDS. For example, a condition can be caused, in part, by a population of cells expressing an undesirable gene. These cells can be ablated and replaced with administered cells expressing an artificial RNA molecule that decreases expression of the undesirable gene. The artificial RNA molecules described herein can be targeted to essentially any gene, the decreased expression of which can be helpful in treating or preventing HIV infection and/or AIDS.

Any suitable cell can be used. For example, cells to be transfected or transduced can be essentially any type of cell for implantation into in a subject. The cell having the target gene can be germ line or somatic, totipotent or pluripotent, dividing or non-dividing, parenchymal or epithelial, immortalized or transformed, or the like. The cell can be a stem cell or a differentiated cell. After transduction or transfection, stem cells can be administered to a subject, or cultured to form differentiated stem cells (e.g., embryonic stem cells cultured to form neural, hematopoietic, or pancreatic stem cells) or cultured to form differentiated cells.

Stem cells can be stem cells recently obtained from a donor, and in certain embodiments, the stem cells are autologous stem cells. Stem cells can also be from an established stem cell line that is propagated in vitro. Suitable stem cells include embryonic stems and adult stem cells, whether totipotent, pluripotent. multipotent, or of lesser developmental capacity. Stem cells can be derived from mammals, such as rodents (e.g., mouse or rat), primates (e.g., monkeys, chimpanzees, or humans), pigs, or ruminants (e.g., cows, sheep, and goats). Examples of mouse embryonic stem cells include: the JM1 ES cell line described in M. Qiu et al., Genes Dev 9, 2523 (1995), and the ROSA line described in G. Friedrich, P. Soriano, Genes Dev 5, 1513 (1991), and mouse ES cells described in U.S. Pat. No. 6,190,910. Many other mouse ES lines are available from Jackson Laboratories (Bar Harbor, Me.). In addition, examples of embryonic stem cells are described in the following patents and published patent applications: U.S. Pat. Nos. 8,647,872, 6,245,566; 6,200,806; 6,090,622; 6,331,406; 6,090,622; 5,843,780; US 2002/0045259; US 2002/0068045. Examples of human adult stem cells include those described in the following patents and patent applications: U.S. Pat. No. 8,999,706. U.S. Pat. Nos. 7,259,011, 6,387,367; 6,265,175; 6,242,252; 6,184,035; 6,129,911; 5,968,829; 5,958,767; 5,958,767; 5,958,767; 5,958,767; 5,958,767; 5,789,246; 5,766,948; 5,486,359; US 2014/0170122, US 2002/0016002; US 2002/0076400; US 2002/0098584; and, for example, in International Publication No. WO 01/11011. Examples of making and using hematopoietic stem cells are described, e.g., in U.S. Pat. Nos. 8,617,885, 8,383,404, 7,927,785, 7,807,464, 7,767,453, 5,763,197, U.S. Publication No. 2012/0071397, International Publication Nos. WO 1996/033281 and WO 1996/022693. In certain embodiments, a suitable stem cell can be derived from a cell fusion or dedifferentiation process, such as described in U.S. Publication No. US 2002/0090722, in International Publication Nos. WO 02/38741, WO 01/51611, WO 99/63061, and WO 96/07732.

Transduced or transfected cells can also be used in the manufacture of a medicament for the treatment of subjects. Examples of pharmaceutically acceptable excipients include matrices, scaffolds, or other substrates to which cells can attach (optionally formed as solid or hollow beads, tubes, or membranes), as well as reagents that are useful in facilitating administration (e.g., buffers and salts), preserving the cells (e.g., chelators such as sorbates, EDTA, EGTA, or quaternary amines or other antibiotics), or promoting engraftment. Cells can be encapsulated in a membrane or in a microcapsule. Cells can be placed in microcapsules composed of alginate or polyacrylates. (Sugamori et at (1989) Trans. Am. Soc. Artif. Intern. Organs 35:791; Levesque et al. (1992) Endocrinology 130:644; and Lim et al. (1992) Transplantation 53:1180).

Additional methods for encapsulating cells are known in the art. (Aebischer et al. U.S. Pat. No. 4,892,538; Aebischer et al. U.S. Pat. No. 5,106,627; Hoffman et al. (1990) Expt. Neurobiol. 110:39-44; Jaeger et al. (1990) Prog. Brain Res. 82:4146; and Aebischer et al. (1991) J. Biomech. Eng. 113:178-183, U.S. Pat. Nos. 4,391,909; 4,353,888; Sugamori et al. (1989) Trans. Am. Artif Intern. Organs 35:791-799; Sefton et al. (1987) Biotehnol. Bioeng. 29:1135-1143; and Aebischer et al. (1991) Biomaterials 12:50-55).

The site of implantation of cell compositions can be selected by one skilled in the art depending on the type of cell and the therapeutic objective. Exemplary implantation sites include intravenous or intra-arterial administration, administration to the liver (via portal vein injection), the peritoneal cavity, the kidney capsule, or the bone marrow.

In certain embodiments, the disclosure provides for modification of nucleic acids and delivery (e.g., ex vivo or in vivo delivery) of modified nucleic acids. These modified nucleic acids can include a nucleic acid molecule (e.g., shRNA cluster or artificial miRNA cluster) described herein. These modified nucleic acids can also include, e.g., shRNA-like molecules, modified pri-miRNA-like molecules, and artificial RNA molecules, as described herein. Modification and delivery of modified nucleic acids, including RNAs incorporating modified nucleotides, such as those with chemical modifications to the 2'-OH group in the ribose sugar backbone, such as 2'-O-methyl (2'OMe), 2'-fluoro (2'F) substitutions, and those containing 2'OMe, or 2'F, or 2'-deoxy, or "locked nucleic acid" (LNA) modifications can be accomplished as described in U.S. Pat. Nos. 6,627,616, 6,897,068, 6,379,966; in U.S. Patent Application Publication Nos. US. 2005/0107325, US 2007/0281900 and US 2007/0293449; and in Vorhies and Nemunaitis J J, Methods Mol Biol. 2009; 480:11-29. Lopez-Fraga M et al., Infect Disord Drug Targets. 2008 December; 8(4):262-73, Watts et al., Drug Discov Today. 2008 October; 13(19-20):842-55. Lu and Woodle, Methods Mol Biol. 2008; 437:93-107, de Fougerolles et al., Hum Gene Ther, 2008 February; 19(2):125-32, Rossi J J, Hum Gene Ther. 2008 April; 19(4):313-7, Belting M and Wittrup A. Methods Mol Biol. 2009; 480:1-10, Pushparaj et al., J. Dent. Res. 2008; 87: 992-1003, Shrivastava and Srivastava, Biotechnol J. 2008 March; 3(3):339-53, and Raemdonck K. et al., Drug Discov Today, 2008 November; 13(21-22):917-31. CastanottoD & Rossi J J, Nature 2009 January; 457:426-433, Davis M et al., Nature 464, 1067-1070 (15 Apr. 2010), each of which are incorporated by reference in their entireties.

Combination Therapies

The nucleic acid molecules (e.g., shRNA clusters or artificial miRNA clusters), artificial RNA molecules (e.g., RNAi molecules), cells, viral particles, and compositions (e.g., pharmaceutical compositions) described herein can be used in combination with other therapies. For example, the combination therapy can include a nucleic acid molecule (e.g., shRNA duster or artificial miRNA cluster), artificial RNA molecule (e.g., RNAi molecule), cell, and composition described herein co-formulated with, and/or co-administered with, one or more additional therapeutic agents, e.g., anti-HIV agents, vaccines, or agents that enhance an immune response. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject before or during the course of the subject's affliction with a disease, e.g., an HIV infection or AIDS. In one embodiment, two or more treatments are delivered prophylactically, e.g., before the subject is infected or diagnosed with HIV. In another embodiment, the two or more treatments are delivered after the subject has been infected or diagnosed with HIV infection or AIDS. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to an infection or disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Exemplary HIV or AIDS therapies that can be combined with an shRNA cluster, nucleic acid molecule (e.g., artificial miRNA cluster), artificial RNA molecule (e.g., RNAi molecule), cell, viral particle, and composition (e.g., pharmaceutical composition) described herein include, but are not limited to, a non-nucleoside reverse transcriptase inhibitor (NNRTI) (e.g., nevirapine, delavirdine, efavirenz, etravirine, rilpivirine, IDX899, RDEA-428, or lersivirine), a nucleoside reverse transcriptase inhibitor (NRTI) (e.g., zidovudine, didanosine, zalcitabine, stavudine, lamivudine, abacavir, emtricitabine, or entecavir), a nucleotide reverse-transcriptase inhibitor (NtRTI) (e.g., tenofovir), a protease inhibitor (PI) (e.g., saquinavir, ritonavir, indinavir, nelfinavir, amprenavir, lopinavir, fosamprenavir, atazanavir, tipranavir, or darunavir), a fusion inhibitor (e.g., enfuvirtide), a CCR5 antagonist (also called an entry inhibitor) (e.g., maraviroc), an integrase strand transfer inhibitor (INSTI) (e.g., elvitegravir, dolutegravir, or raltegravir), or any combination thereof.

In certain embodiments, the additional therapeutic agent is a second shRNA cluster, nucleic acid molecule (e.g., artificial miRNA cluster), artificial RNA molecule (e.g., RNAi molecule), cell, viral particle, or composition (e.g., pharmaceutical composition), as described herein.

Screening Methods

Constructs containing a nucleic acid molecule (e.g., shRNA cluster or artificial miRNA cluster) described herein, or libraries of such constructs can be introduced into intact cells/organisms and can be used in screening, such as high throughput screening (HTS). For example, potential targets for pharmaceuticals can be identified or studied using such constructs or libraries. A panel of nucleic acid molecules (e.g., shRNA clusters or artificial miRNA clusters) that affect target gene expression by varying degrees may be used. In particular, it may be useful to measure any correlation between the degree of gene expression decrease and a particular phenotype.

Libraries of nucleic acid molecules (e.g., shRNA clusters or artificial miRNA clusters) can be produced using methods known in the art. For example, libraries of nucleic acid molecules (e.g., shRNA clusters or artificial miRNA clusters) can be based on existing libraries, such as existing shRNA libraries. Existing materials and methods for design and construction of expression cassettes, selection and modification of vectors and vector backbones, library construction, design of target sequences, and library validation, as applied to conventional shRNA libraries may be applied in the construction of libraries comprised of the shRNA clusters or nucleic acid molecules (e.g., artificial miRNA dusters) of the present disclosure. As non-limiting examples, such materials and methods are described in Chang et al. Nature Meth. 3:707-714 (2006), International Publication No. WO12009/055724, the contents of which are specifically incorporated herein by reference.

In certain aspects, the disclosure provides methods for screening/evaluating gene function in vivo. A cell containing a construct for expression of an shRNA-like molecule, modified pri-miRNA-like molecule, or artificial RNA molecule may be introduced into an animal and a phenotype may be assessed to determine the effect of the decreased gene expression. An entire animal may be generated from such cells (e.g., ES cells) containing the construct of the nucleic acid molecule (e.g., shRNA cluster or artificial miRNA cluster) described herein. A phenotype of the animal may be assessed. The animal may be essentially any experimentally tractable animal such as a non-human primate, a rodent, a canine, a feline, etc. Populations of animals expressing different members of a library of nucleic acid molecules (e.g., shRNA clusters or artificial miRNA clusters) may also be generated. The phenotypes of such animals may be assessed to determine, for example, the effect of a target gene on a disease phenotype, stem cell differentiation, drug sensitivity, susceptibility to a viral infection, or any other phenotype of interest.

EXAMPLES

Example 1: Multiplexing Seven miRNA-Based shRNAs to Suppress HIV Replication This example describes a strategy to express a large number of shRNA-miRs using optimal flanking sequences from multiple endogenous miRNAs. It was found that a sequence of 30 nucleotides flanking the miRNA duplex was sufficient for efficient processing of shRNA-miRs. Multiple shRNAs were inserted in tandem, each containing minimal flanking sequence from a different miRNA. Deep sequencing of transfected cells showed accurate processing of individual shRNA-miRs and that their expression did not decrease with the distance from the promoter. Moreover, each shRNA was as functionally competent as its singly expressed counterpart. This system was used to express one shRNA-miR targeting CCR5 and six shRNA-miRs targeting the HIV-1 genome. The lentiviral construct was pseudotyped with HIV-1 envelope to allow transduction of both resting and activated primary CD4 T cells. Unlike one shRNA-miR, the seven shRNA-miR transduced T cells nearly abrogated HIV-1 infection in vitro. Additionally, when PBMCs from HIV-1 seropositive individuals were transduced and transplanted into NOD/SCID/IL-2R γc−/− mice (Hu-PBL model), efficient suppression of endogenous HIV-1 replication with restoration of CD4 T cell counts was observed. Thus, our multiplexed shRNA appears to provide a promising gene therapeutic approach for HIV-1 infection.

Design of Multiplexed shRNA-miRs

Figure 1B:
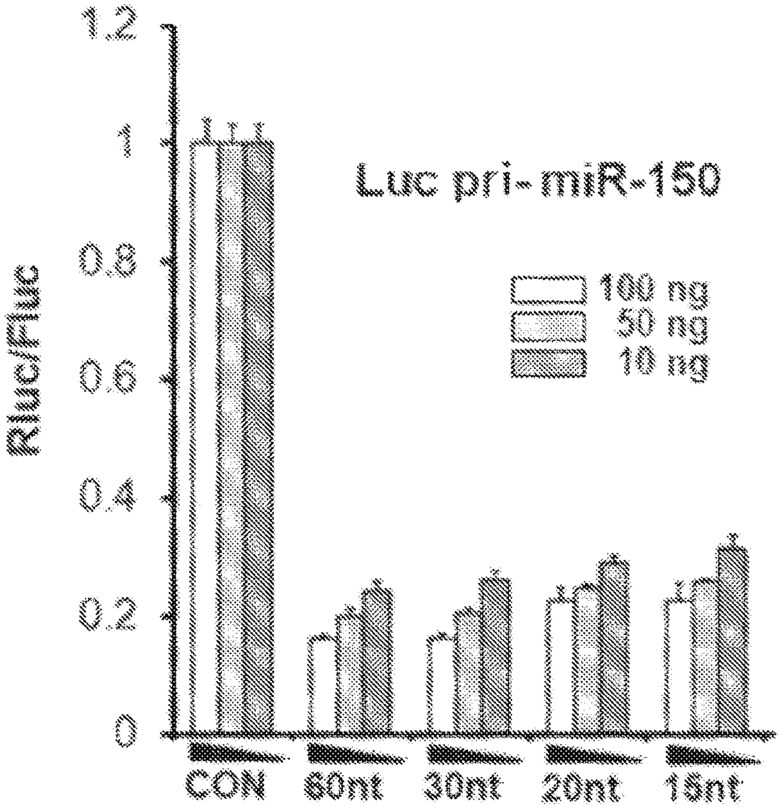

The essential difference between conventional shRNA and shRNA-miR is that while the former resembles pre-miRNA that is processed by Dicer in the cytoplasm, the latter resembles pri-miRNA that is first processed by Drosha/DGCR8 in the nucleus (Han et al., *Genes Dev* 18: 3016-3027; Yi et al. Genes Dev 17: 3011-3016; Chendrimada Nature 436: 740-744). Although based on in vitro processing of select miRNAs, it has been suggested that Drosha cuts the pri-miRNA ~11 nt from the lower stem-single stranded RNA (ssRNA) junction, this may not always hold true for all miRNAs, particularly in vivo (Ma et al., Proc Natl Acad Sci USA 110: 20687-20692). Moreover, whether including just these flanking sequences will enable pri-miRNA processing is not known. Thus, the minimal flanking sequences required for processing of different miRNAs were examined. Starting with miR-30a backbone with 150-nt flanking sequences, the flanking sequence length was shortened to 30, 20, and 15-nt and tested the impact on the functionality of the miRNA. For this, plasmids expressing miRNA were co-transfected with different flank lengths along with psiCHECK vector containing the relevant target site in the 3' UTR of Rluc and measured activity by dual luciferase assay 24 h later. FIG. 1A shows that the functionality of pri-miR-30a with 150-nt flanking sequence is similar to that with 30 or 20-nt flanking sequence, while a 15-nt flanking sequence slightly diminishes functionality. The functionality of pri-miR-150 was also tested with 60- or 30-, 20-, or 15-nt flanking sequences and no difference between 60 and 30 nt flanks was detected (FIG. 1B), suggesting that a 30-nt flanking sequence is long enough to ensure proper Drosha processing to retain the full functionality of miRNA. Thus, 30-nt flanks were used for all miRNA backbones.

Figure 1C:
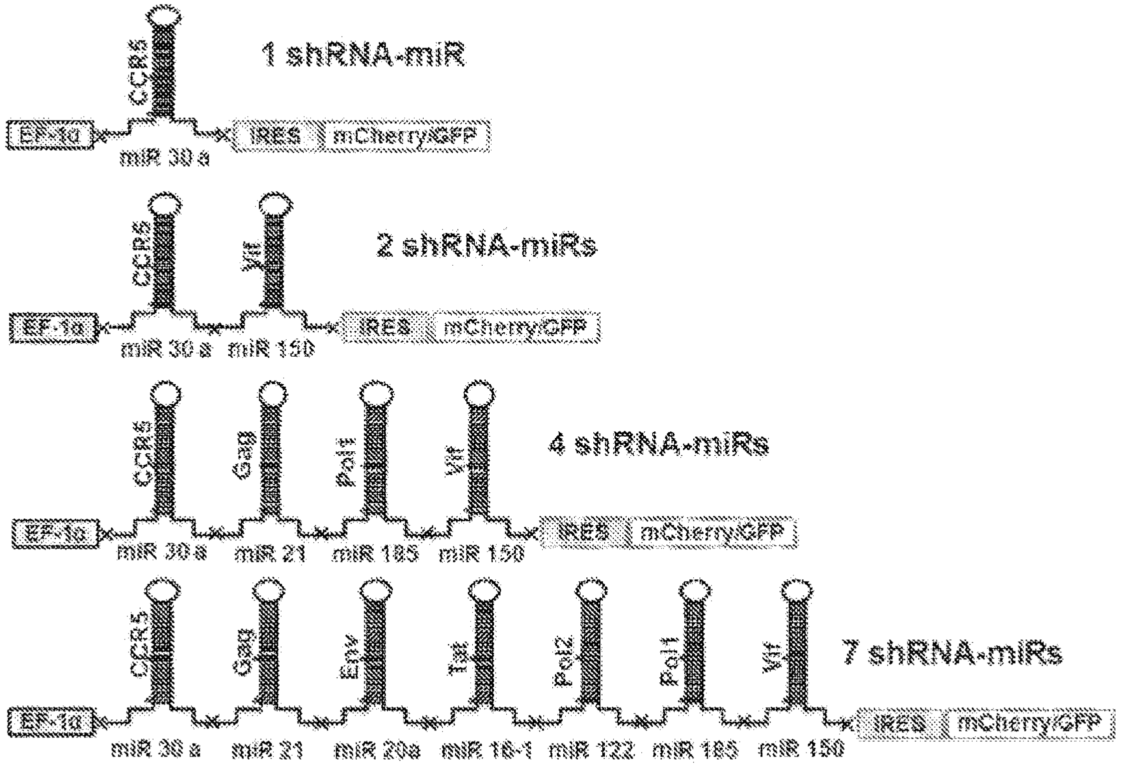
Figure 1D:
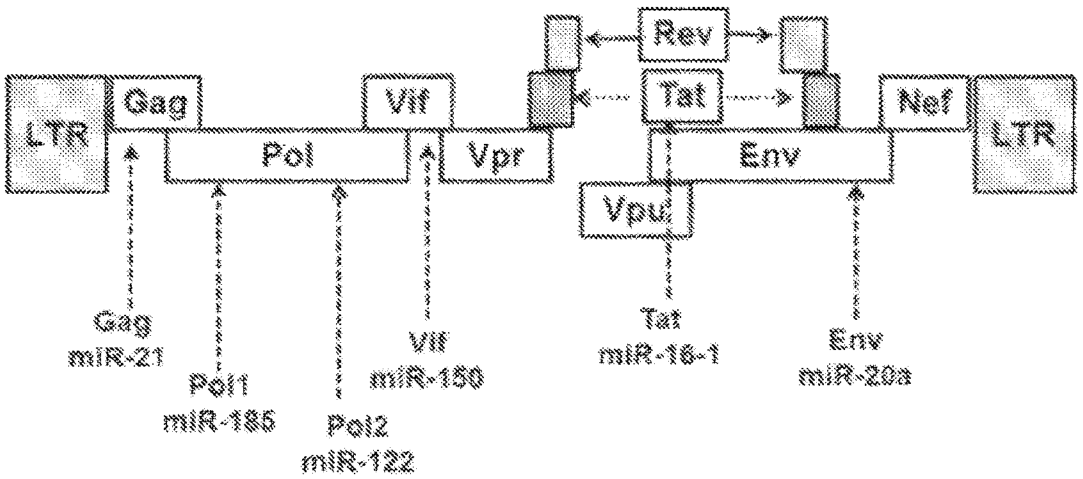

Multiplexing seven shRNA-miRs into a single construct without decreasing functionality of individual shRNAs. Multiple shRNAs cannot be expressed using tandem repeats of the same miRNA backbone because homologous recombination at the flanking sequences is likely to eliminate the insert. An artificial miRNA cluster was designed to multiplex shRNA-miRs under different miRNA backbones. First, it was determined that tandem expression of 2 shRNA-miRs with or without a spacer sequence between them did not affect the shRNA functionality, indicating that 2 tandem miRNAs can be directly combined. Thus, different numbers (1, 2, 4, and 7) of shRNA-miRs were expressed, each with a different miRNA backbone (without any spacer sequence between the individual miRNAs) under the control of EF-1 a promoter, as illustrated in FIG. 1C. The shRNA sequences were picked as they had shown the efficacy of conventional shRNAs targeting the CCR5 gene and highly conserved regions in the HIV-1 genome.

Figure 7:
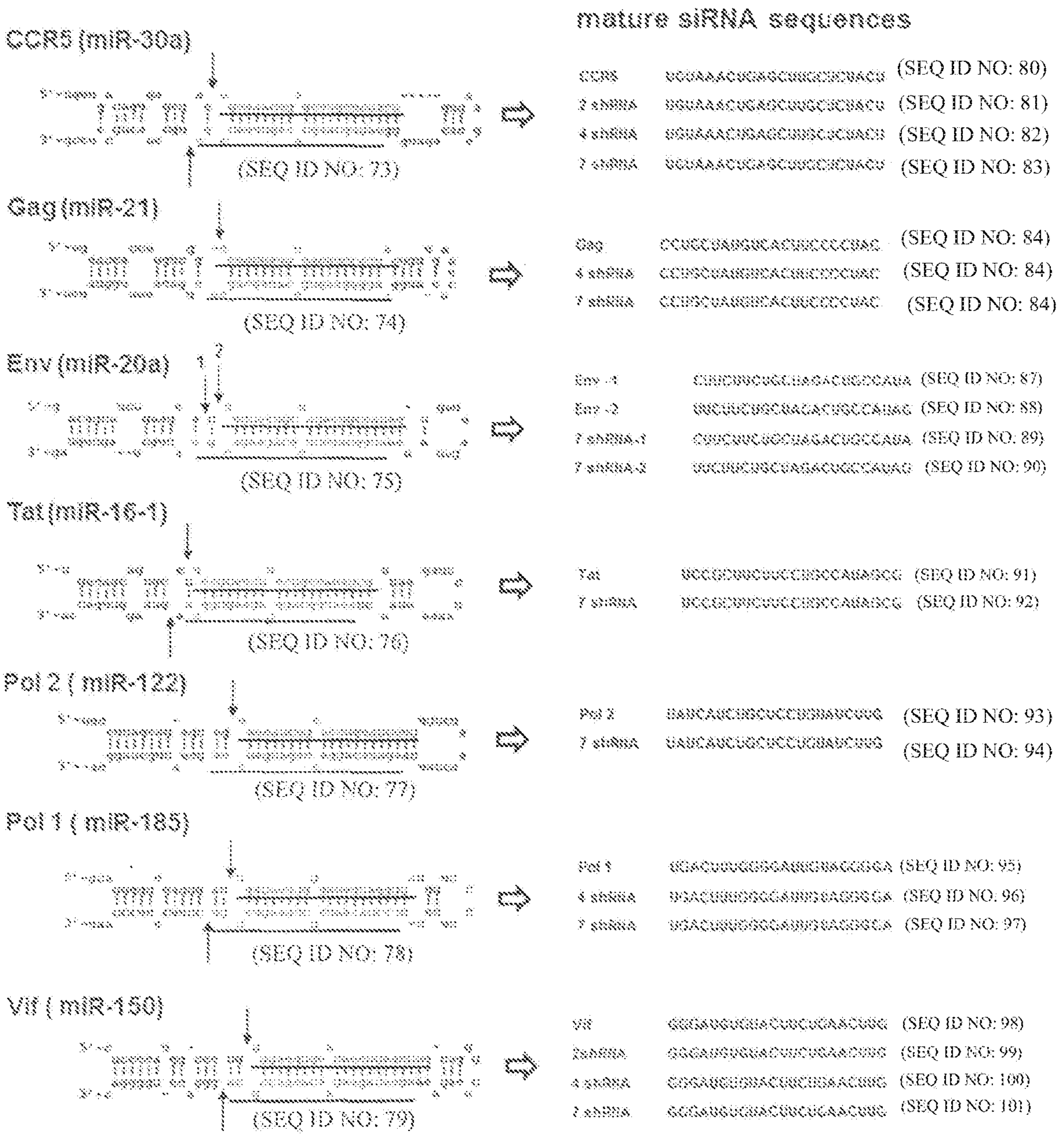
FIG. 7 shows exemplary shRNA-miRNA structures and sequences, (Seq ID No. 80, Seq ID No. 81, Seq ID No. 82, Seq ID No. 83, Seq ID No. 84 Seq ID No. 87, Seq ID No. 88, Seq ID No. 89, Seq ID No. 90, Seq ID No. 91, Seq ID No. 92, Seq ID No. 93, Seq ID No. 94, Seq ID No. 95, Seq ID No. 96, Seq ID No. 97, Seq ID No. 98, Seq ID No. 99, Seq ID No. 100, and Seq ID No. 101). Left panel shows each shRNA-miR hairpin (Seq ID No. 73, Seq ID No. 74, Seq ID No. 75, Seq ID No. 76, Seq ID No. 77, Seq ID No. 78, and Seq ID No. 79). The predicted sequence is underlined. Arrows indicate the Drosha cleavage sites. Right panel represents dominant small RNA sequences obtained by deep sequencing of individual or multiplexed shRNA-miR constructs.

First it was tested if the shRNA-miRs in the multiplex are correctly processed and whether their expression is affected by the position of each individual shRNA-miR with respect to the promoter. siRNAs produced from single, 2, 4, or 7 shRNA-miRs were determined using deep sequencing. For this, 293 T cells were transfected with either of the single, 2, 4, or 7 shRNA-miR expression constructs and small RNAs isolated 48 h later were cloned and deep sequenced. siRNAs were detected for each unit in all the constructs. Moreover, analysis of the dominant reads show accurate and predicted processing of 6/7 shRNAs (FIG. 7). Only in 1 (Env), there were 2 forms, one as predicted, but one with 1 bp shift. However, even with some of the endogenous miRNAs, alternative processing is known to occur. Thus, the siRNAs generated appears to be the right ones.

Figure 8:
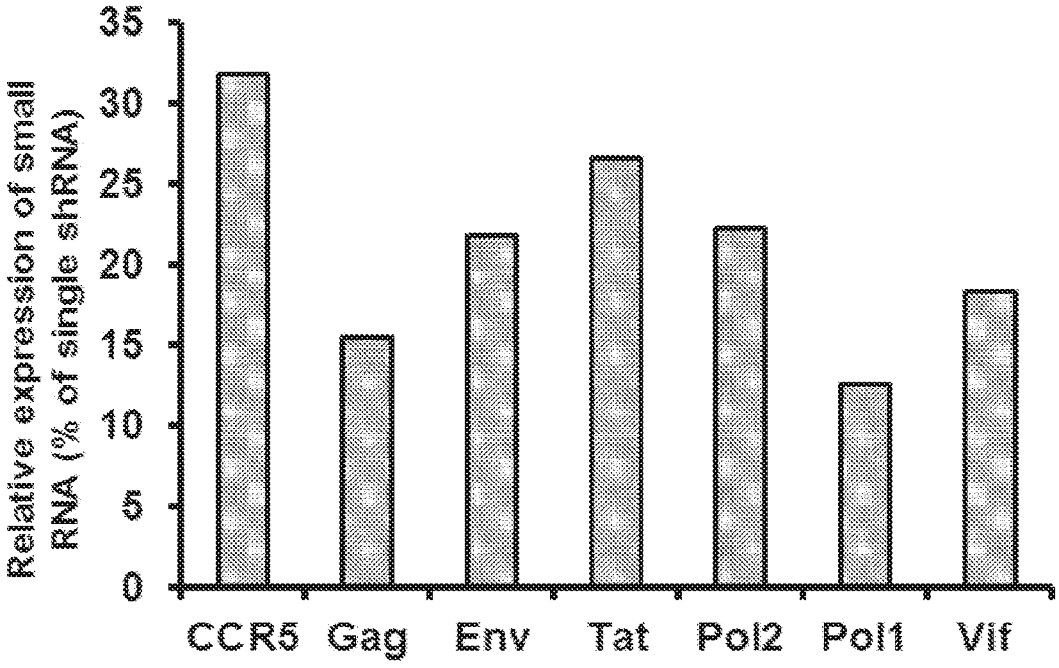
FIG. 8 depicts the frequency of individual siRNA reads generated from 7 shRNA-miRs. 293 T cells were transfected with indicated single or 7 shRNA-miRs and 48 h later small RNAs obtained from cell lysates cloned and deep sequenced. Small RNA reads were normalized by dividing the read numbers by the endogenous miR-16 (Table 3). Relative expression was calculated using the formula: (small RNA reads for indicated shRNA-miRs in 7 shRNA-miR transfected cell/small RNA reads for endogenous miR-16)/(small RNA read number for individual shRNA-miRs in single shRNA-miR transfected cell/small RNA reads for endogenous miR-16)×100.

Analysis of the read number frequencies revealed that the expression of individual shRNA-miRs in the multiplex is not affected by the position of that shRNA-miR with respect to the promoter. Although the small RNA reads showed 3-8-fold lower from the 7 shRNA-miR construct as compared to single shRNA-miR (FIG. 8, Table 1), the reads of all siRNAs in the construct (CCR5, Gag, Env, Tat, Pol1, Pol2, and Vif) were significantly higher than one of the most abundant endogenous miRNA, miR-16. Thus, the level of each of the 7 shRNAs appears to be adequate to suppress all targeted genes.

Figure 2A:
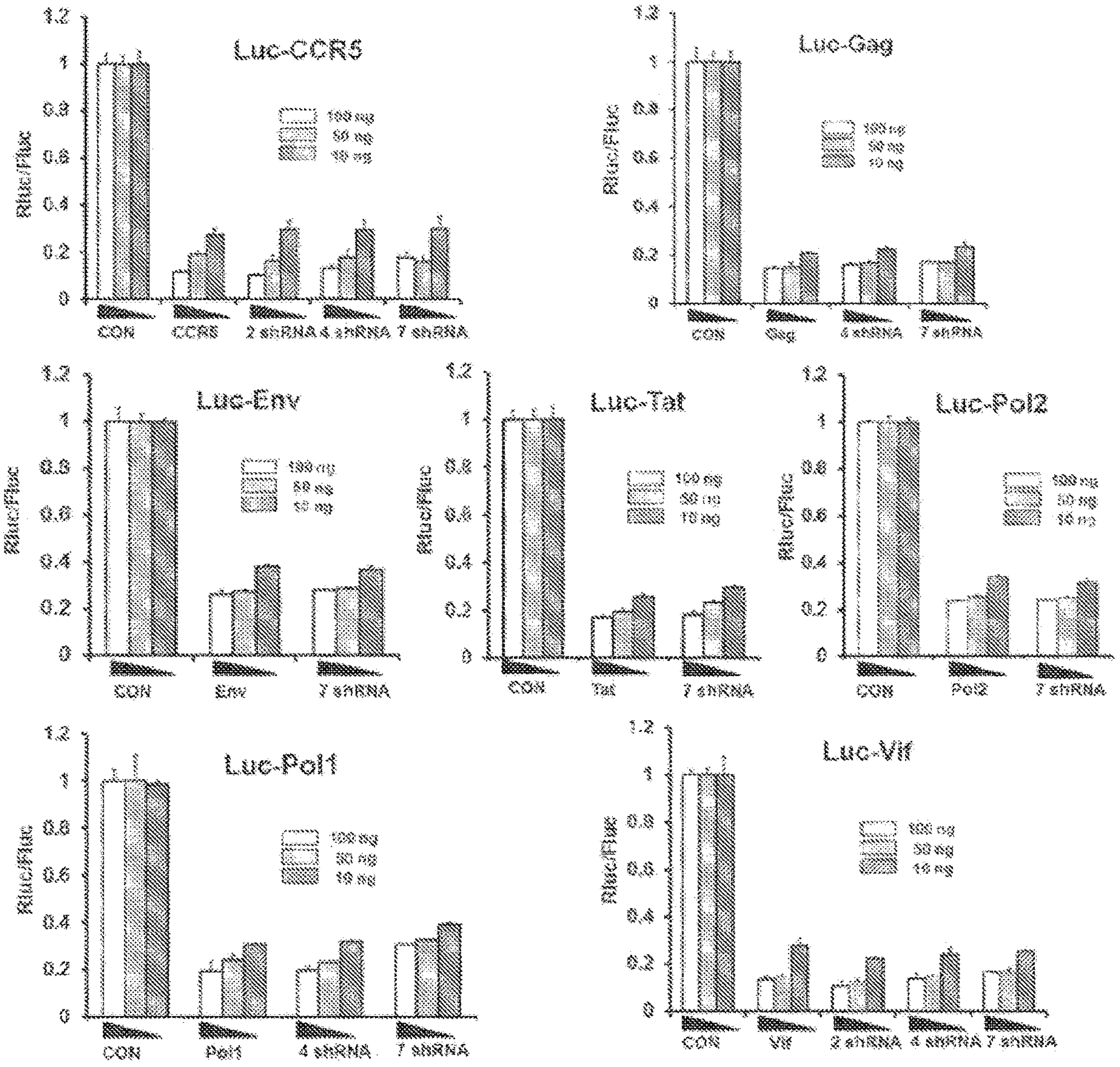
FIGS. 2A-2C illustrate competency of shRNA-miR expressed from multiplexed shRNA-miRs contruct, in accordance with the disclosed embodiments.
Figure 2B:
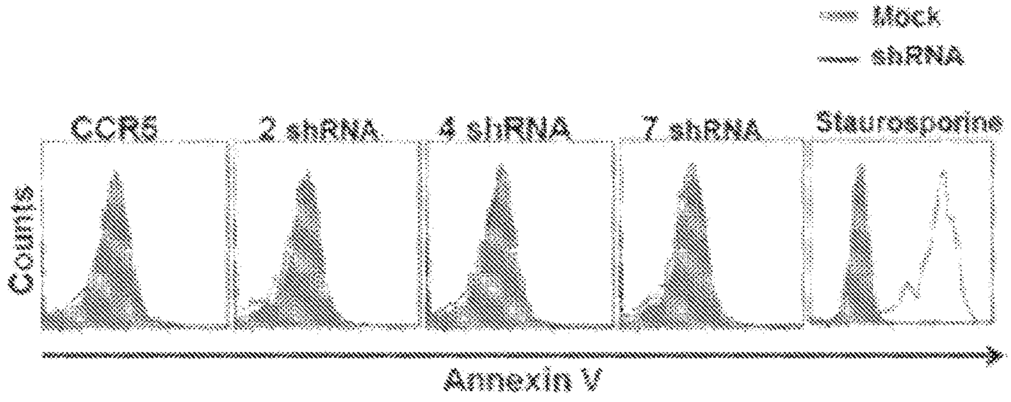

Next, individual shRNA-miR functionality in the multiplex was tested. For this, plasmids expressing single or multiple shRNA-miRs were co-transfected along with psiCHECK vector containing relevant shRNA-miR target sites in the 3' UTR of Rluc and measured activity by dual luciferase assay 24 h later. All individual shRNA-miRs within all multiplexed vectors (expressing 2, 4, or 7 shRNA-miRs) showed similar functionality compared to plasmids expressing only the individual shRNA-miRs (FIG. 2A). This was seen at all different concentration of plasmids used for transfection. The toxicity of single, dual, and multiple shRNA-miR constructs was also evaluated. Transfection of Jurkat cells with multiple shRNA-miR expression construct was not toxic to the cells as determined by annexin V staining (FIG. 2B).

The different shRNA-miR expression cassettes (expressing 1, 2, 4, and 7 shRNAs) were cloned in a lentiviral vector that also expresses mCherry or Zs Green as markers. The vectors were pseudotyped with HIV-1 envelope and the resultant lentivirus was used for transduction of primary CD4 T cells. The lentiviral titer with multiplexed shRNA-miRs was around 10 fold lower than single shRNA-miRs, but still sufficient to perform experiments after concentration by ultracentrifugation.

Figure 2C:
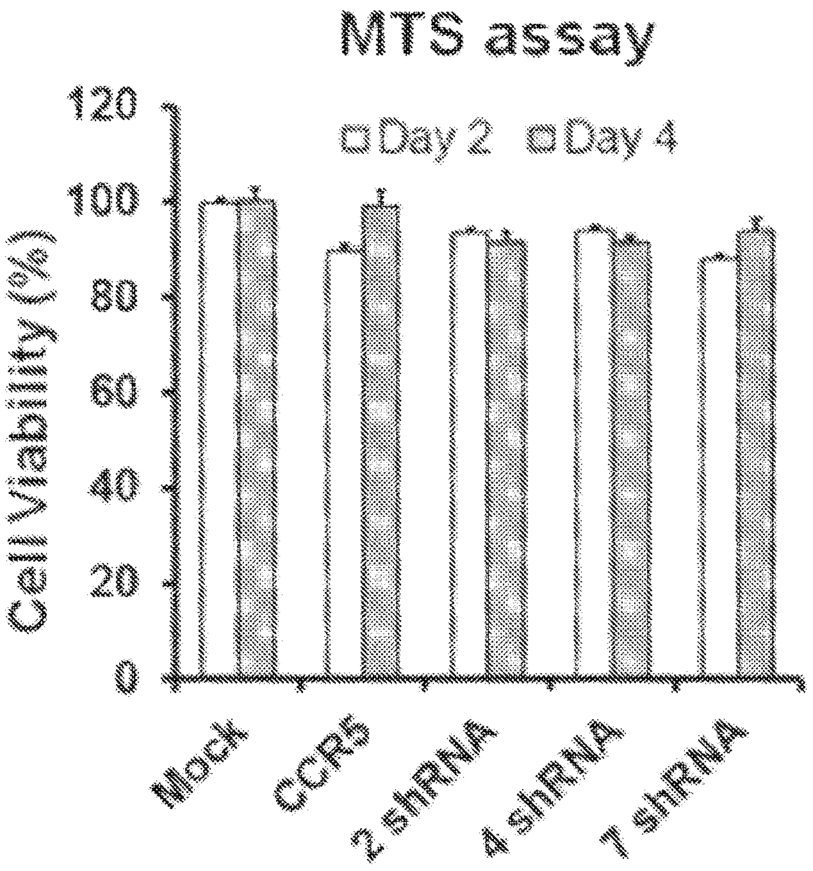
Figure 9:
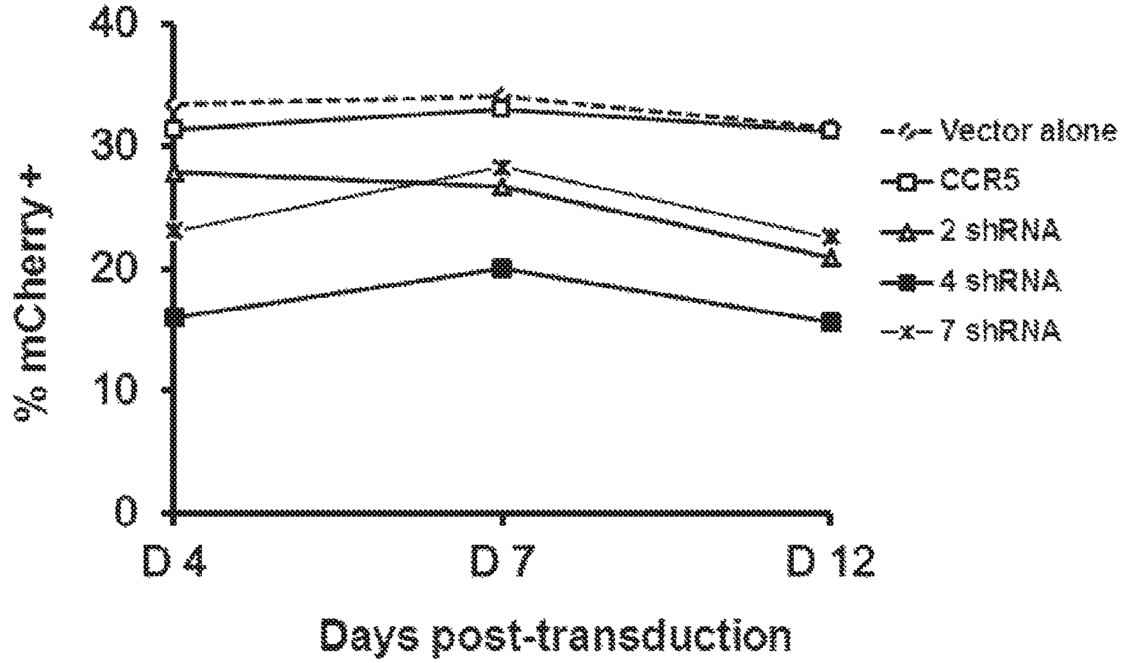
FIG. 9 is a graphical representation of data showing mCherry (vector alone, single, and multiplex shRNA-miRs) expression in vector transduced PBMCs over time.

To monitor toxicity, the cells were cultured for 4, 7, and 12 days after lentivirus transduction and followed the percentage of mCherry+ cells by flow cytometry. Although mCherry expression levels varied between different constructs, the expression levels did not decline with time for any of the constructs (FIG. 9). Cell viability of the transduced CD4 T cells was also tested by the MTS assay on days 2 and 4 after transduction. No decrease in the viability of transduced cells was observed (FIG. 2C). Thus, these data indicate that single and multiple shRNA-miR constructs were stable and had no obvious adverse effects on cell viability in vitro.

Functionality of shRNA-miRs targeting CCR5 and multiple HIV-1 genes in cell lines.

Figure 3A:
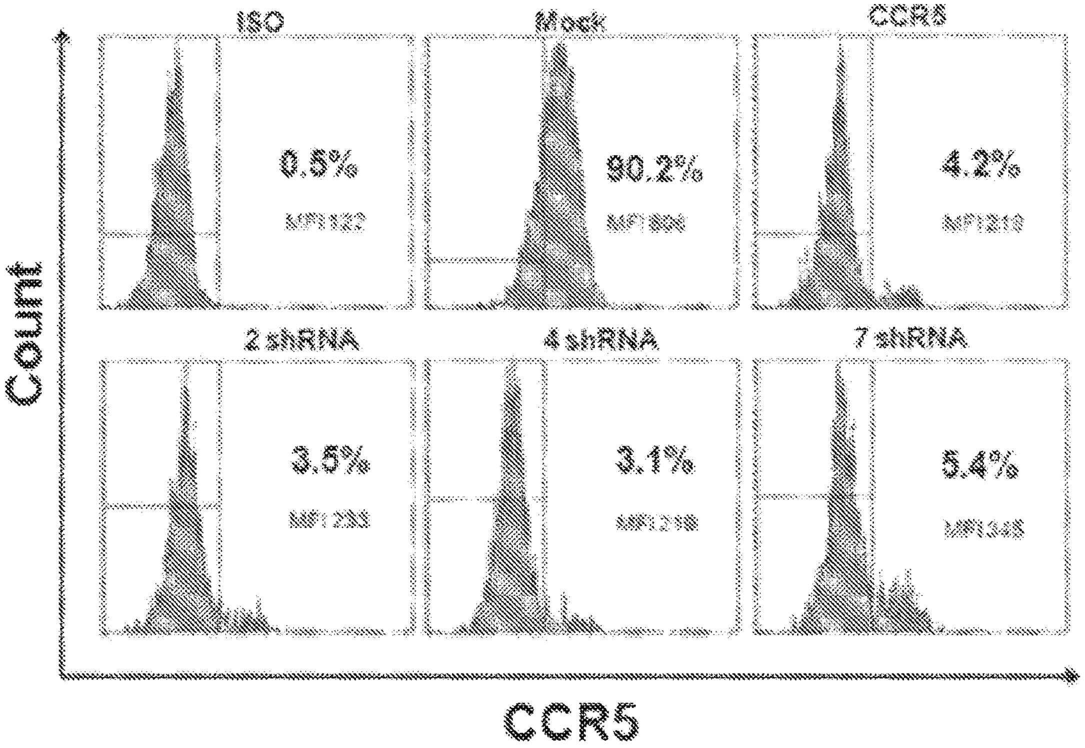
FIGS. 3A-3C illustrate the effect of multiplexed shRNA-miR on CCR5, in accordance with disclosed embodiments.
Figure 3B:
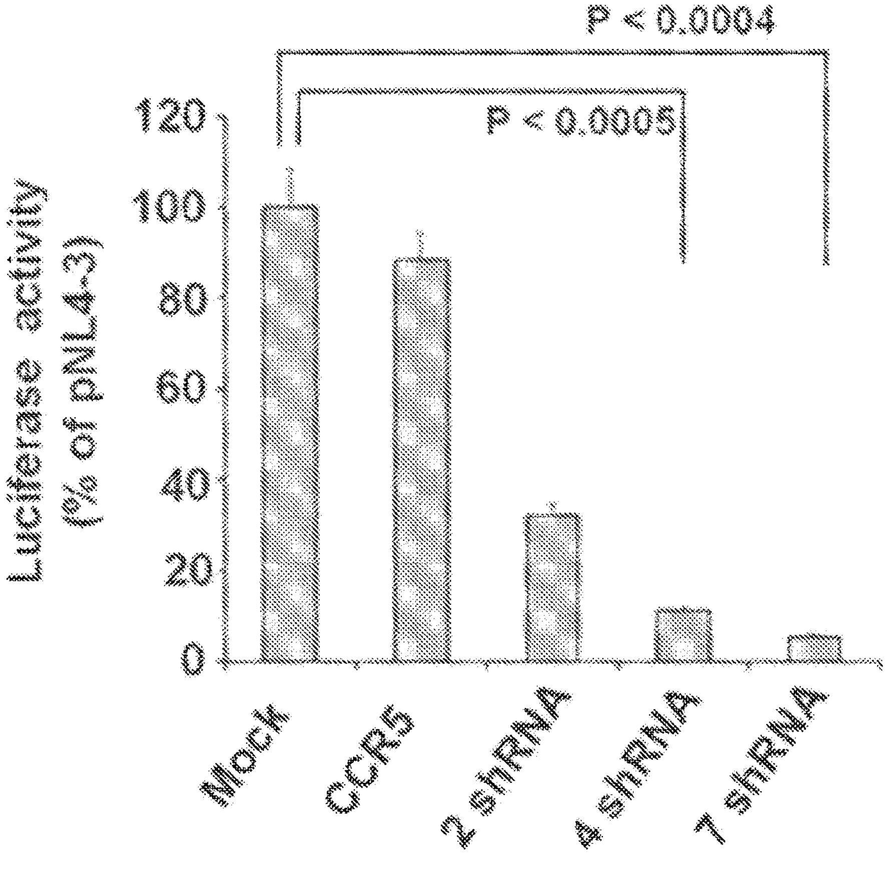
Figure 3C:
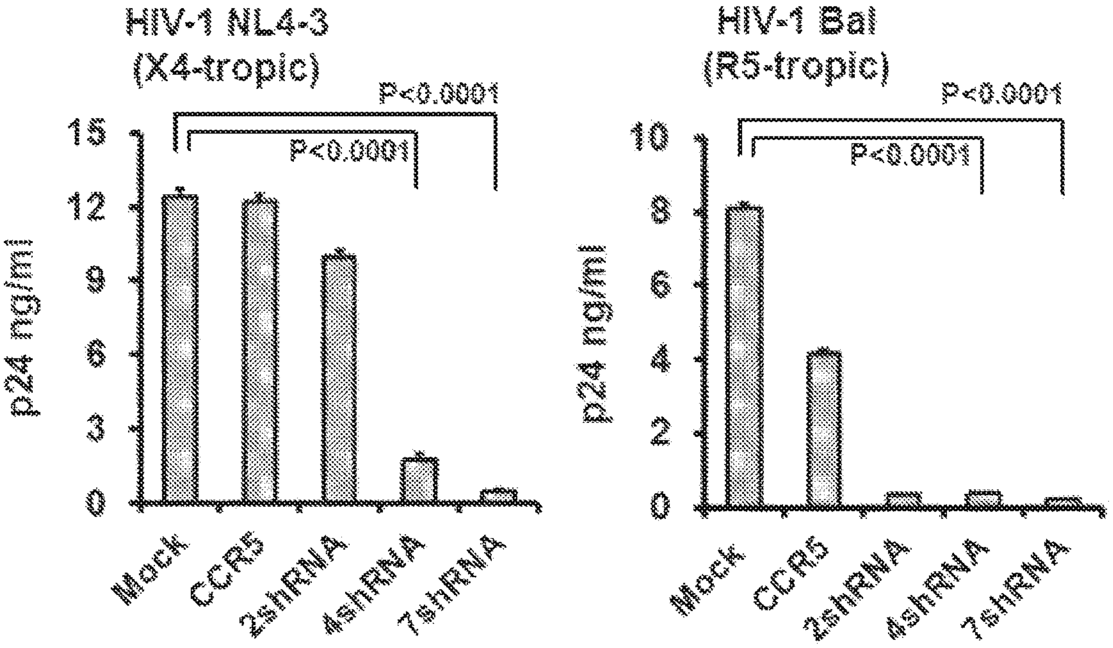

The ability of single, dual, and multiple shRNA-miR constructs to knockdown CCR5 was tested in the TZM-bl cells. Cells were transduced with lentiviruses encoding 2, 4, and 7 shRNA-miRs and after 48 h, CCR5 expression was tested by flow cytometry. As shown in FIG. 3A, all 3 constructs could effectively silence CCR5 expression as compared to cells transduced with lentivirus expressing mCherry alone. To test the efficacy of antiviral shRNA-miRs, 293 T cells were co-transfected with X4 tropic HIV-1 molecular clone pNL4-3 plasmid along with 2, 4, or 7 shRNA-miR encoding vectors. Culture supernatants obtained 48 h later were tested for viral replication by infecting TZM-bl cells encoding Tat-dependent luciferase. While as expected, supernatants from CCR5 shRNA-miR transfected cells had no effect on viral levels compared to control, that from antiviral shRNA treated samples showed increasingly (7shRNA-miR<4shRNA-miR<2shRNA-miR) lower levels of infectivity, suggesting antiviral shRNA-miRs were also functional (FIG. 3B). To evaluate the antiviral effect of CCR5 and antiviral shRNA-miRs in the context of lentivirus transduction, TZM-bl cells were transduced with HIV-1-pseudotyped lentiviruses encoding 1, 2, 4, or 7 shRNA-miRs and 24 h later infected with either X4-tropic NL4-3 or R5 tropic HIV-1Bal at an MOI of 0.01. p24 levels in culture supernatants were tested 9 days after infection. Again, CCR5 shRNA-miR transduction had no effect on X4 tropic virus, but inhibited R5 tropic virus by 50% and antiviral shRNA-miRs showed increasing levels of inhibition, with 7shRNA-miR virtually abrogating infection with both X4 tropic and R5 tropic viruses (FIG. 3C). Thus, the artificial miRNA clusters appears to be capable of expressing multiple functional shRNA-miRs and therefore can serve as good candidates for anti-HIV-1 therapy.

Figure 4A:
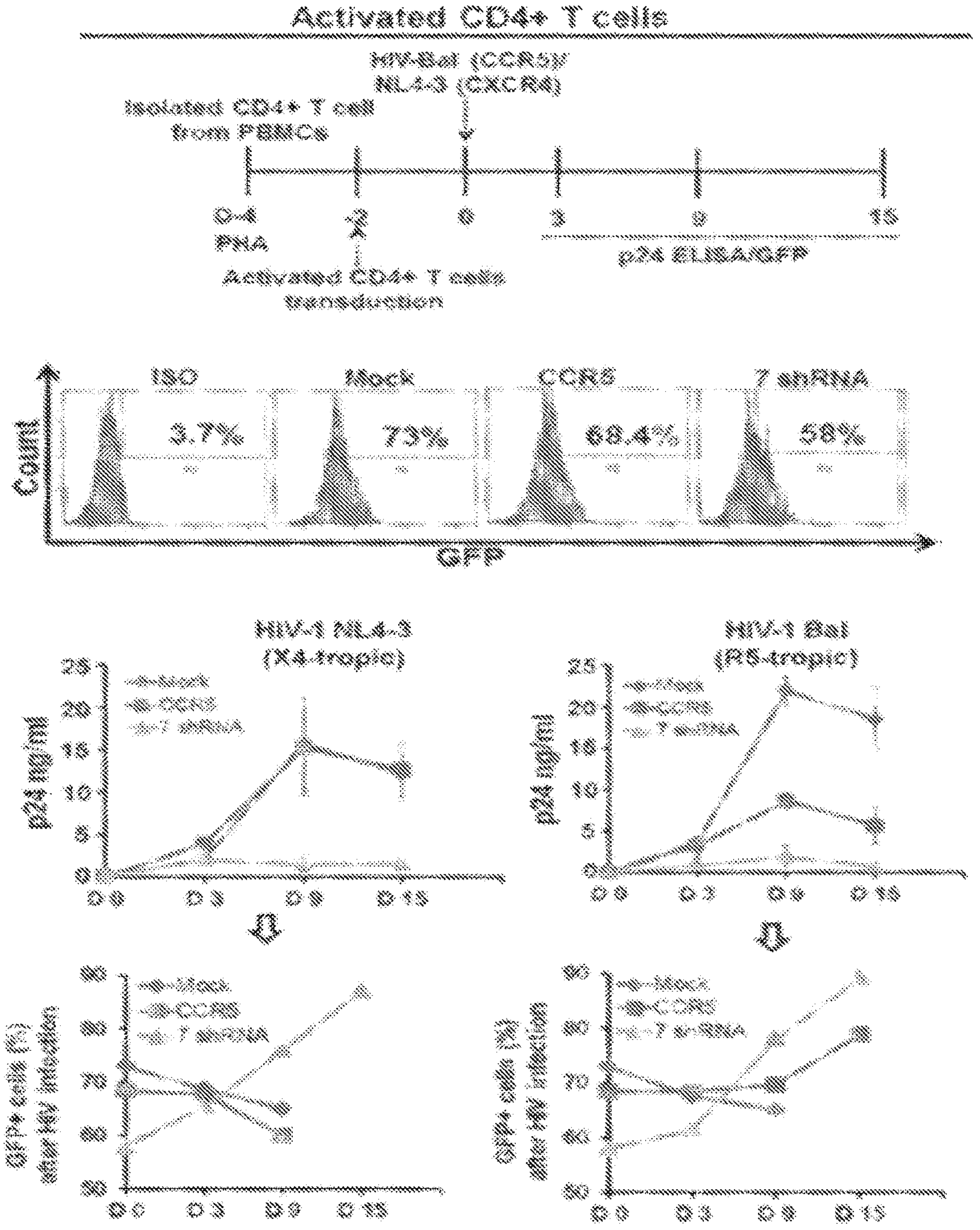
FIGS. 4A-4B illustrate transduction and protection of resting and activated T cells by HIV-1 env-pseudotyped lentiviral vector expressing multiplexed shRNA-miRs, in accordance with disclosed embodiments.
Figure 4B:
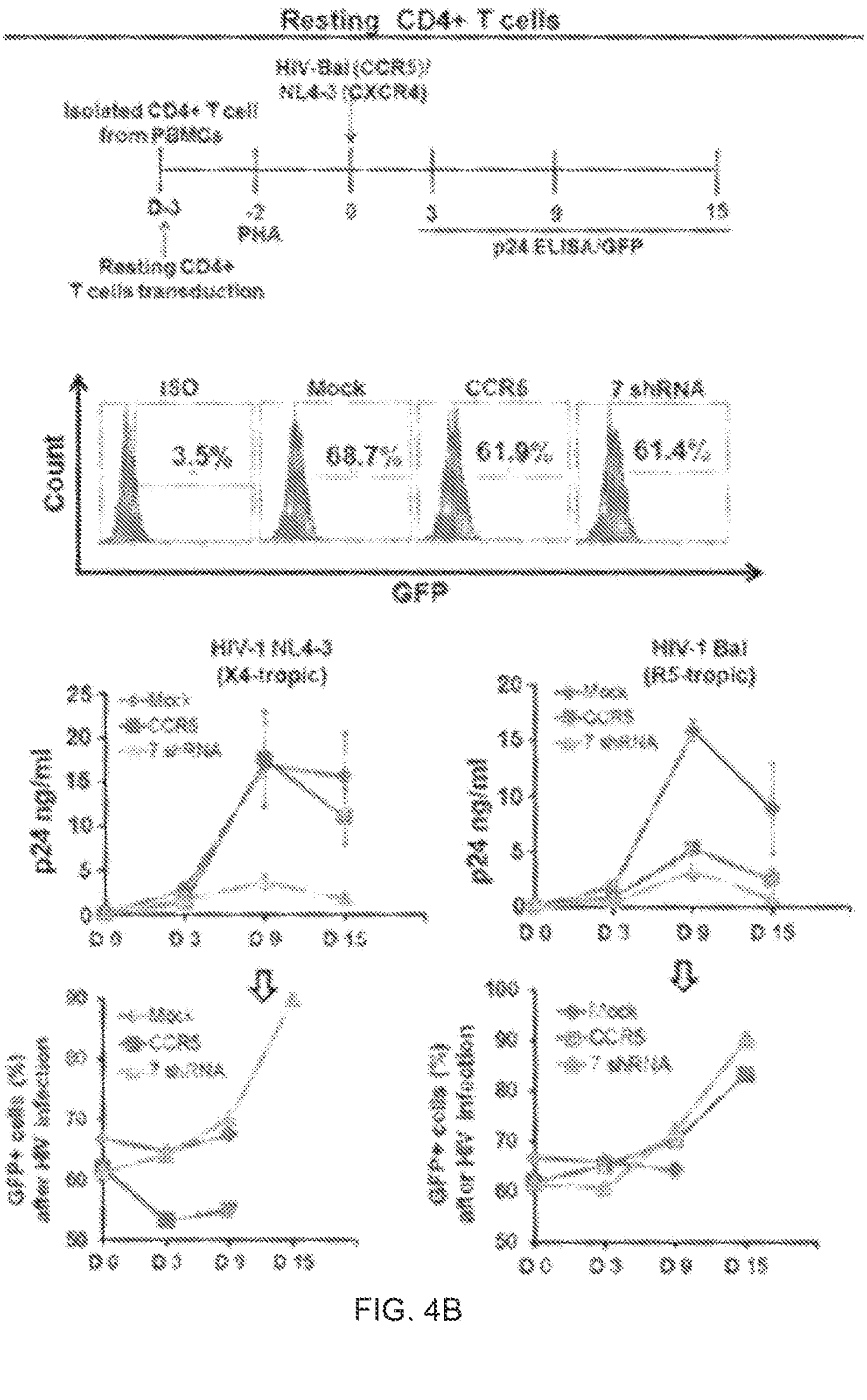
Figure 10:
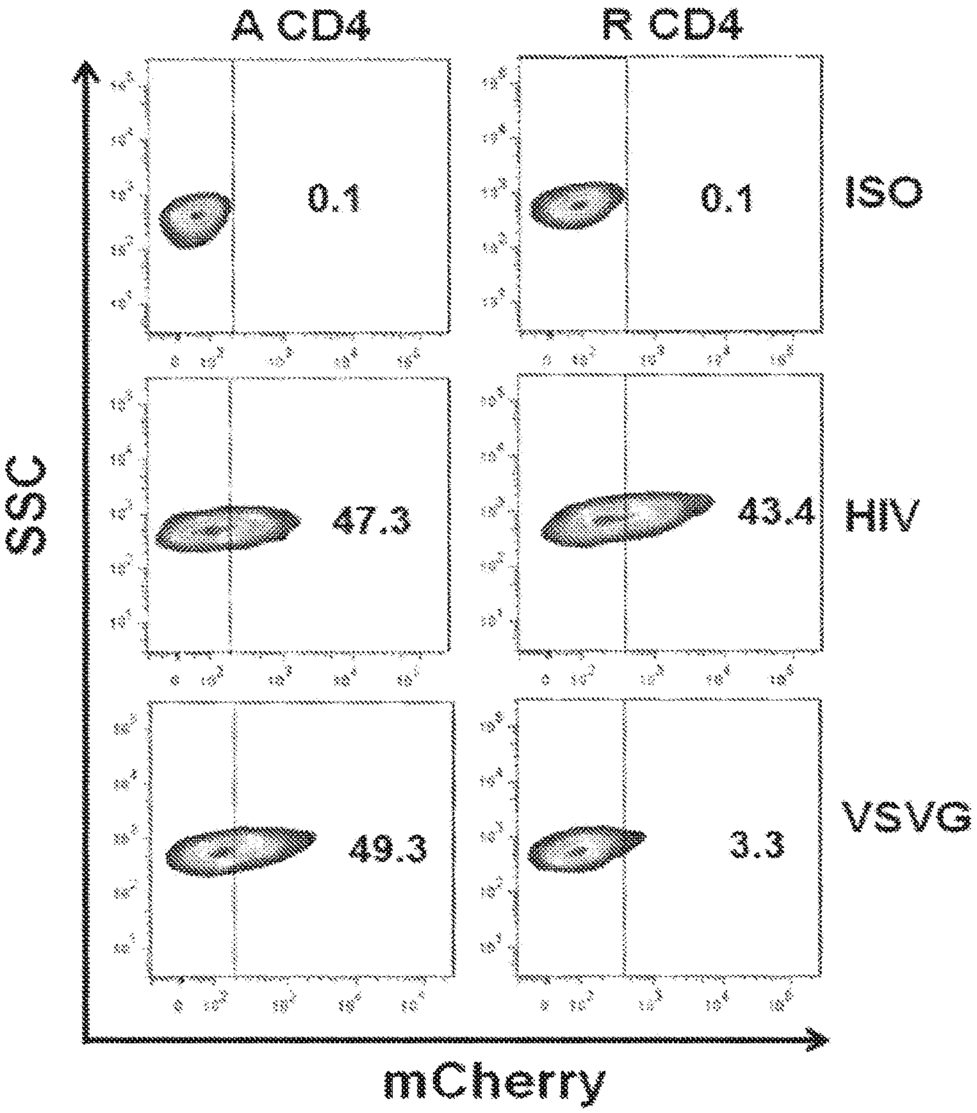
FIG. 10 depicts that activated (A CD4) and resting CD4 T (R CD4) cells were transduced with VSV-G or HIV env-pseudotyped lentivirus and mCherry expression determined 48 hours later by flow cytometry.

Resting T Cells can be Effectively Transduced with HIV-1-Env Pseudotyped shRNA-miR Expressing Lentivirus Having established that multiplexed shRNA-miRs are functional, the efficacy of CCR5 only versus CCR5+6 antiviral shRNA-miRs was next tested to resist HIV-1 infection in activated and resting primary CD4 T cells. The goal was to develop a method to confer HIV-1 resistance to all T cells, regardless of activation status. Thus, the transduction efficiency of VSV-G and HIV-1 env-pseudotyped lentiviruses expressing mCherry was first tested. Primary CD4 T cells were transduced either before or after activation with PHA for 2 days and examined for mCherry expression 2 days after transduction. Flow cytometric analysis revealed that while both VSV-G and HIV-1 envelope-pseudotyped viruses transduced activated T cells with equal efficiency, effective transduction of resting T cell could be achieved only with the latter (FIG. 10). Thus, the HIV-1 envelope pseudotyped virus was used for testing antiviral efficacy. To evaluate the shRNA-miRs, resting or activated CD4 T cells were transduced with HIV-1 pseudotyped lentiviruses expressing no shRNA-miR, CCR5 shRNA-miR alone, or CCR5+6 antiviral shRNA-miRs. In this experiment, GFP-expressing lentivirus was used to track the transduced cells. After 48 h, the cultures were infected with HIV-1 strains, NL4-3, or Bal (transduced resting T cells were activated with PHA before infection). Culture supernatants harvested on days 0, 3, 9, and 15 were tested for released virus levels by p24 ELISA. The transduction levels were comparable between the three LV constructs in both activated and resting CD4 T cells (FIGS. 4A-4B). Again, similar to results obtained for TZM-bl cells, while CCR5 shRNA-miR was effective only against R5 virus, the 7 shRNA-miR expressing LV was able to nearly abrogate infection of both X4 and R5 tropic viruses in both activated and resting T cells (FIGS. 4A-4B). Moreover, GFP expressing cells increased over time in the protected CCR5 shRNA-miR and 7 shRNA-miR transduced cultures. The high enrichment of viable GFP positive cells and the well preserved cell viability at the end of the experiment on day 15 points to a clear survival advantage of the shRNA-miR transduced cells following HIV-1 infection (FIGS. 4A-4B). It was concluded that 7 shRNA-miR expressing lentivirus, pseudotyped with HIV-1 envelope provides a means to confer HIV-1 resistance in primary CD4 T cells.

Figure 5A:
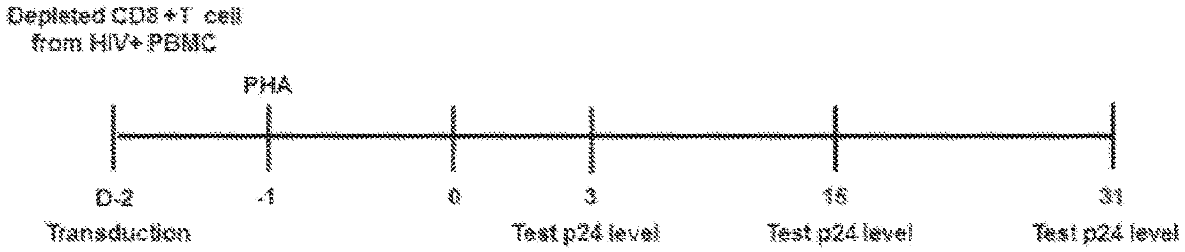
Figure 5B:
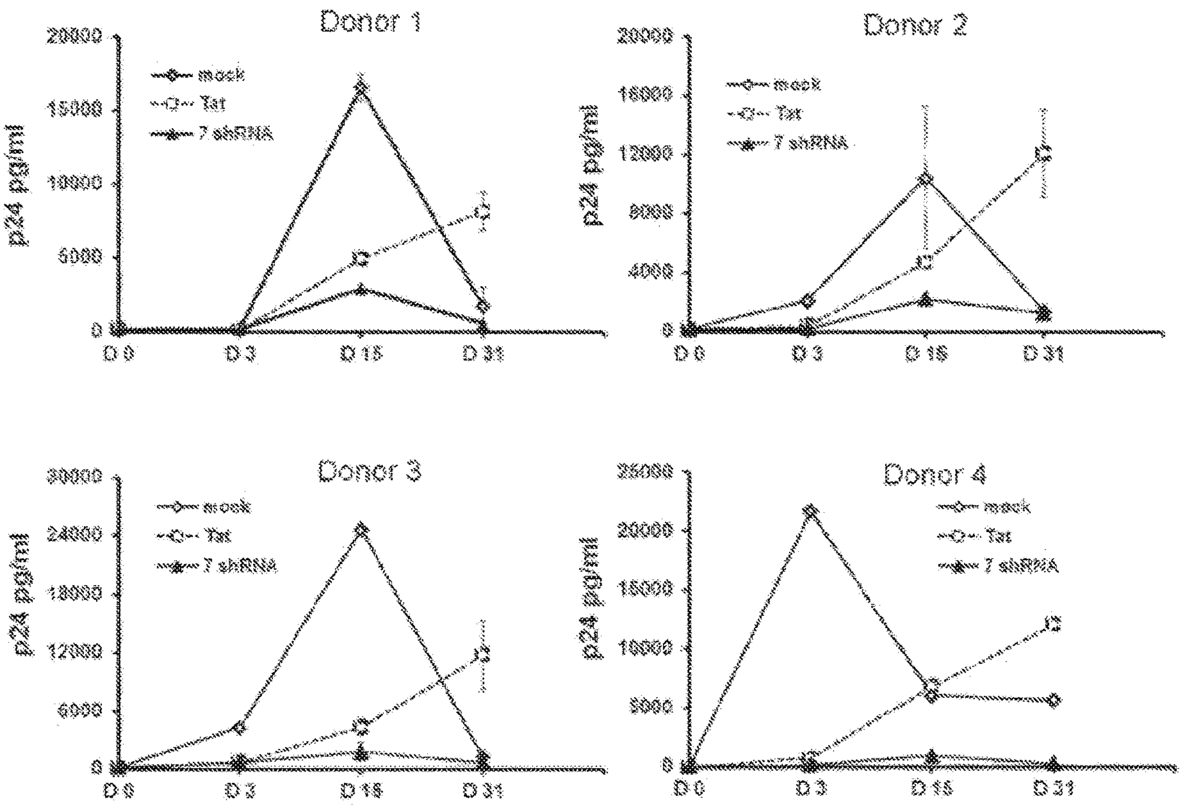

Inhibition of HIV-1 Replication in HIV-Seropositive Donor PBMCs Transduced with HIV-1 Env-Pseudotyped 7 shRNA-miR Encoding Lentivirus In addition to the effectiveness of shRNA-miRs to prevent infection, it was next tested if the replication of HIV-1 can be inhibited from already infected cells. For this, PBMC obtained from HIV-1 seropositive individuals, either treatment naïve or on ART were used. Since in this case, antiviral shRNA-miRs are mainly relied on, shRN-miR targeting Tat only or 7shRNA-miRs were used to test efficacy. First, it was ensured that the transduction efficacy of all the vectors to be similar by determining mCherry expression by flow cytometry. To test shRNA efficacy, PBMCs from HIV-1 seropositive donors were depleted of CD8 T cells, transduced with shRNA-miR encoding lentiviruses, and activated the next day (FIG. 5A). The cells were cultured for 31 days and p24 antigen levels determined on days 0, 3, 15, and 31. As shown in FIG. 5B, in the control lentivirus (expressing no shRNA-miR) transduced cells, HIV-1 replication showed a peak on day 15 and declined by day 31, presumably due to depletion of CD4 T cells by infection. In contrast, in the 7 shRNA-miR transduced cultures, HIV-1 replication by day 15 was dramatically reduced in all 4 donor PMBCs and by day 31, p24 was virtually undetectable, even though the cultures contained healthy looking cells. In the Tat shRNA-miR only transduced cells, at day 15 HIV-1 replication was reduced in all four donors PBMCs. However at later time points, Tat shRNA-miR transduced cell cultures showed increased HIV-1 replication (FIG. 5B), indicating either inadequacy of Tat shRNA-miR antiviral activity or emergence of escape mutants. The presence of HIV-1 escape mutants were tested by sequencing Tat shRNA-miR target regions in the virus present in the supernatants. Of the 4 donors, cultures from two showed emergence of viral escape mutants. Donor 2 had a mutation at nucleotide position 18 and donor 4 had mutation at position 4 of the Tat-targeted sequence (FIG. 5C). In the 7shRNA-miR treated cultures, virus could not be recovered to perform similar studies.

Figure 6A:
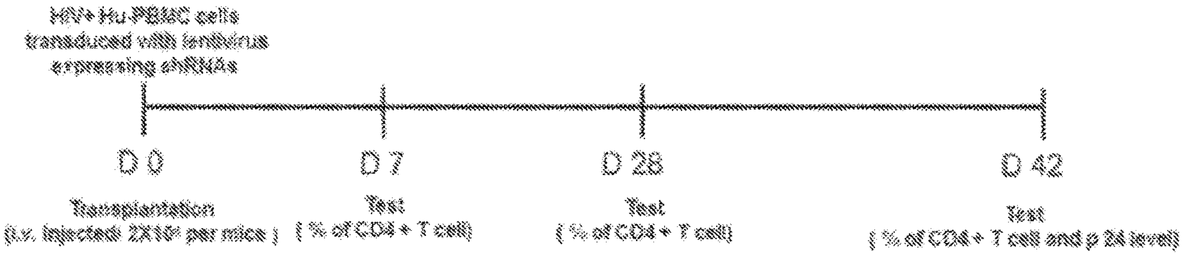
FIGS. 6A-6C illustrate prevention of CD4 T cell loss and endogenous HIV-1 replication in 7 shRNA-miR treated HIV seropositive PBMC transplanted Hu-PBL mice, in accordance with disclosed embodiments.
Figure 6B:
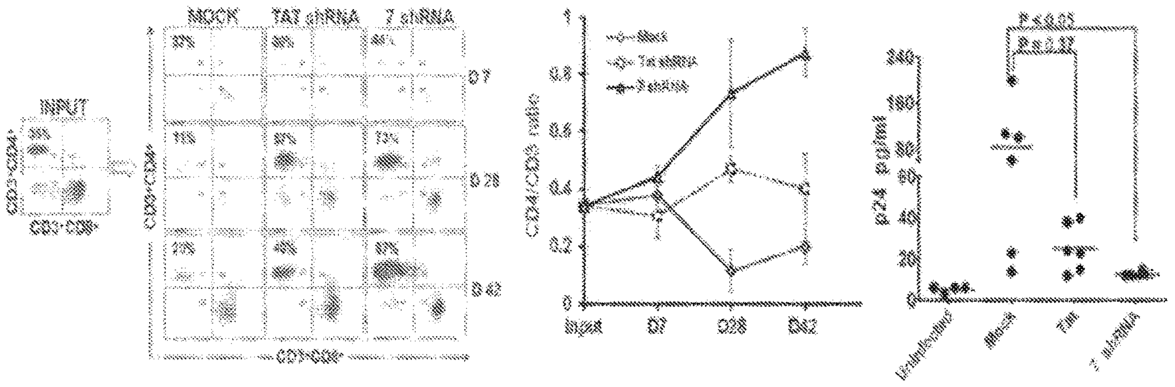
Figure 6C:
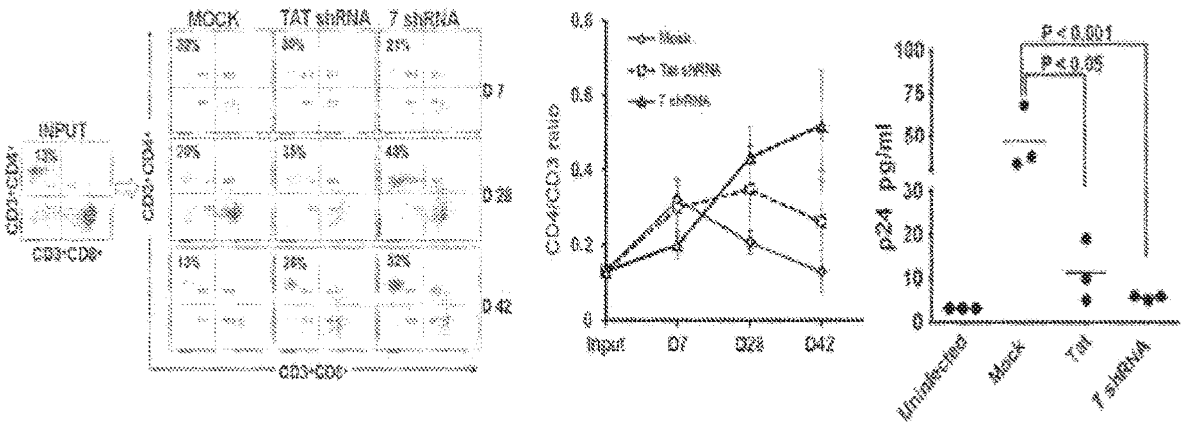

Multiplexed miRNA-Based 7 shRNA-miRs Prevent CD4 T Cell Loss and HIV-1 Replication in Hu-PBL Mice Reconstituted with PBMCs from HIV-1+ Patients Transplantation of gene modified T cells is being tried as a potential treatment in HIV-1 infected individuals (Surabhi and Gaynor (2002). J Virol 76: 12963-12973. Thus, it was next tested if reinfusion of 7 shRNA-miR treated cells provides a therapeutic possibility by preclinical testing in the Hu-PBL mouse model. For this, 2 HIV-1 infected individuals, one on ART (donor #1, viral load<20 copies/ml; CD4/CD3 ratio=0.34) and the other, treatment naïve (donor #4, viral load: 67,420 copies/ml; CD4/CD3 ratio=0.13), were selected. PBMCs were transduced with HIV-1 env-pseudotyped lentivirus expressing either no shRNA-miR (mock), only Tat shRNA-miR or 7 shRNA-miRs and injected into NODISCID/IL2-Ryc−/− mice to evaluate their ability to engraft, expand and resist HIV-1 replication. CD4 T cell counts were monitored on days 7, 28, and 42 and serum p24 levels on day 42 (FIG. 6A). In mice reconstituted with lentivirus only (no shRNA-miR) transduced T cells, for both donors, few CD4 T cells were found at all-time points tested and the cell numbers progressively declined over time, consistent with HIV-1 mediated depletion of xenogenically activated CD4 T cells that became productively infected with endogenous virus. In the Tat shRNA-miR only transduced group, CD4 T cells expanded (particularly noticeable in donor #1 on ART) by day 28, but declined by day 42, reflecting the initial effectiveness of a single antiviral shRNA-miR that failed at later time points. In contrast in the 7shRNA-miR transduced group, for both donors, CD4 T cells continued to increase and by day 42, constituted 87% (donor #1, on ART) and 52% (donor #4, treatment naïve) of PBMCs. Correspondingly, viral load was highest in no shRNA-miR control, intermediate in Tat shRNA-miR only and lowest in the 7 shRNA-miR group (FIG. 6B,C). Taken together, these results show that multiplexed miRNA-based 7shRNA can control HIV-1 replication and reverse CD4 T cell loss, thus providing a potential clinically viable treatment strategy.

In summary, a general platform to easily express large numbers of shRNA-miRs using minimal flanking sequences from different endogenous miRNAs was developed to express individual shRNA-miRs. Using this system, seven shRNA-miRs targeting CCR5 and six regions in the HIV-1 genome were expressed and it was shown that this affords better protection in vitro as well as in vivo in Hu-PBL mice.

To confer HIV-1 resistance in a therapeutic setting in any meaningful manner, it is desired to silence host factors and HIV-1 genes simultaneously. However, because HIV-1 is known to escape by mutating the target sites, it is important to be able to target multiple, highly conserved viral regions. If seven shRNAs are simultaneously expressed, it could cover nearly all HIV-1-strains by ensuring that at least four shRNAs are active against any given viral strain.

Advances in understanding Drosha processing of pri-miRNA should allow for rational design of shRNA-miRs. Although Drosha cleavage was previously reported to occur ~11 nt from the lower stem-ssRNA junction (Han et al. Cell 125: 887-901), it was recently found that the microprocessor measures the distances from both the lower and upper stem-ssRNA junctions to determine the cleavage site in human cells, and optimal distances from both structures are critical to the precision of Drosha processing (Ma et al. Proc Natl Acad Sci USA 110: 20687-20692). The results shown in this Example suggest that incorporation of ~30 nt of flanking sequences can be enough to ensure processing of different shRNA-miRs. In this example, efficacy was seen for all seven shRNA-miRs in the backbone of other miRNA flanks of ~30 nt. This finding allows easy multiplexing by expression of shRNA-miRs in different miRNA backbones in tandem. Here, each shRNA-miR will be an independent module that can be easily changed and manipulated. Importantly, the functionality of individual shRNA-miRs within the multiplexed constructs did not decrease compared with constructs containing only single, nonmultiplexed shRNAmiR. In addition, the multiplexed shRNA-miRs were stable and had no obvious adverse effects on cells. More importantly, the seven shRNA-miR transduced resting T cells from HIV-1 seropositive individuals, when reconstituted in Hu-PBL mice led to restoration of CD4 T cell decline, indicating the feasibility of using such therapy in humans. Thus, the lentiviral platform to express seven shRNA-miRs provides a significant advancement towards using RNAi for HIV-1 gene therapy.

Conventionally, VSV-G is used for pseudotyping lentiviruses because of its broad tropism for many different cell types. Nonetheless, cells in the G0 stage of the cell cycle, such as resting CD4 T cells are highly recalcitrant to transduction with VSV-G pseudotyped lentivirus (Agosto, et al. (2009). J Virol 83: 8153-8162). This study shows that lentivirus packaged with X4-tropic envelope from LAI efficiently delivered shRNAs into resting CD4 T cells. This is particularly important since in HIV-1 infection, resting memory CD4 T cells are the well-known reservoirs of latent HIV-1 infection and delivery of shRNAs might prevent viral reactivation in these cells. In addition, less differentiated T cells can persist longer after transfer because they have longer telomeres and are not prone to activation-induced cell death. Furthermore, in the absence of prolonged culture, perturbation of the T cell repertoire is also likely to be minimized. As ex vivo transduction is the only external manipulation required, the approach described herein would allow immediate reinfusion of the gene modified cells into the patient, which simplifies the therapy for wider clinical application.

Thus, this example illustrates a compact and flexible design to express multiple shRNAs without inducing toxic effects or compromising their expression and efficacy. This system was used to express seven shRNA-miRs targeting the CCR5 gene and six regions in the viral genome and showed its effectiveness in suppressing HIV-1 infection in vitro and in vivo in the Hu-PBL model. This strategy provides a clinically viable approach for gene therapy in HIV-1 infection.

Materials and Methods

Plasmids and Constructs

Figure 11:
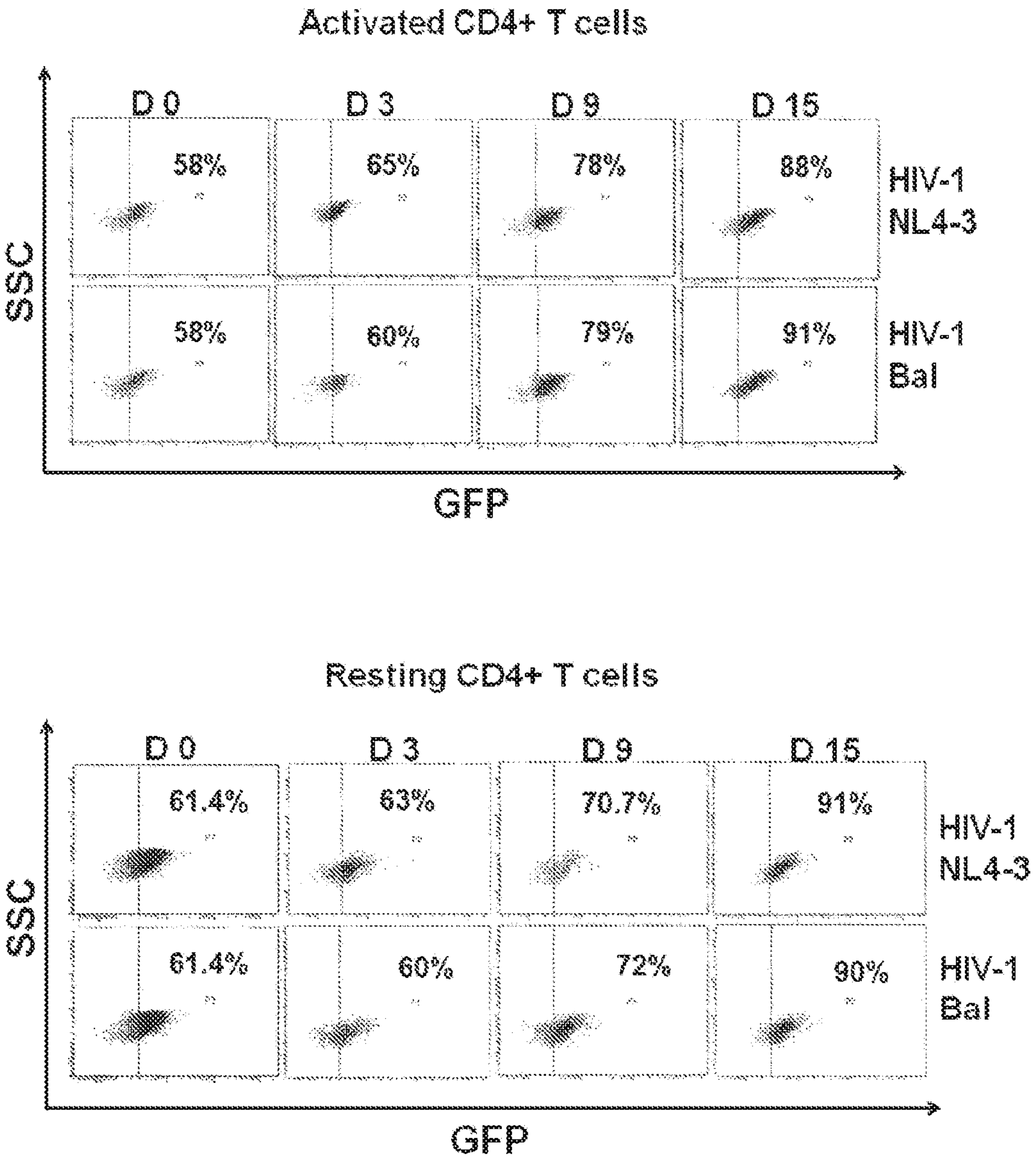
FIG. 11 depicts that activated and resting CD4 T cells transduced with HIV-1 env-pseudotyped lentivirus encoding 7 shRNA-miRs in FIG. 4 were monitored for GFP expression on days 0, 3, 9, and 15 after infection to determine enrichment of HIV-resistant cells.
Figure 12:
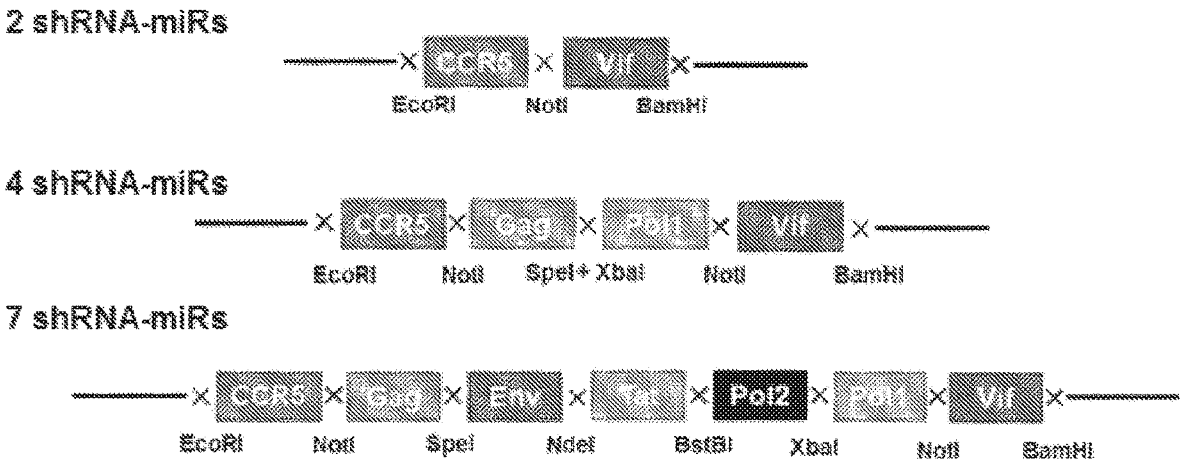
FIG. 12 is schematic of multiplexed shRNA-miRs. Synthesized Ultramer oligos were cloned into pLVX vector with indicated restriction enzyme sites. The inserted sequences can be found in Table 3.

PsiCHECK2 vectors were modified to express shRNA target sites in the *Renilla* luciferase 3' UTR. For this, synthetic oligonucleotides for the forward and reverse strands of the target sequences were annealed and cloned into psiCHECK2 at the XhoI and NotI site. The oligonucleotide target sequences are listed in Table 2 (Seq ID No. 50, Seq ID No. 51, Seq ID No. 52, Seq ID No. 53, Seq ID No. 54, Seq ID No. 55, Seq ID No. 56, Seq ID No. 57, and Seq ID No. 58). To determine the minimal flanking sequence required for efficient processing, we cloned miR-150 and miR-30a with different length of flanking sequences into pLB vector (Addgene plasmid vectors are shown in Table 3 (Seq ID No. 59, Seq ID No. 60, Seq ID No. 61, Seq ID No. 62, Seq ID No. 63, Seq ID No. 64, Seq ID No. 65, and Seq ID No. 66). The shRNAs were inserted into pLVX vector (Clontech plasmid 631987) at the EcoRI and BamHI site. Multiplexed shRNAs were synthesized as ultramers (IDT Technologies) and cloned into pLVX vectors (FIG. 11). The sequences inserted into the vectors are shown in Table 3.

Cell Culture

293 FT/T and TZM-bl cells were cultured as described elsewhere (Perez et al., J Virol 83: 7397-7410). PBMCs were obtained from healthy and HIV infected adult volunteers under an IRB approved protocol. CD4 T cells were isolated from PBMCs using CD4 T cell enrichment kits (Stem cell Technologies, Vancouver, BC, Canada). CD8 Dynabeads (Invitrogen) were used for depleting CD8 T cells from PBMCs. The CD8 depleted PBMCs and isolated CD4 T cells were stimulated with PHA after transduction with lentivirus and were cultured at 37° C. in RPMI 1640 medium supplemented with 10% FBS, 100 U/ml of penicillin-streptomycin with recombinant IL-2 (20 U/ml).

DNA Transfection and Dual-Luciferase Reporter Assay

293 FT cells were co-transfected using 10, 50, and 100 ng shRNA vector and 100 ng of psiCHECK2 plasmid harboring the target regions using Lipofectamine 2000. Dual luciferase assay was performed 24 hours later as reported earlier.

Generation of lentiviral vector and transduction

The lentiviral vector, pLVX-IRES-mCherry, was purchased from Clontech. Oligonucleotides targeting viral Gag, Env, Tat, Pol, Vif, and cellular co-receptor CCR5 were cloned into the EF-1a promoter-expressing lentiviral vector pLVX-IRES-mCherry. 293 T cells were plated to 70-80% confluence in 150 mm dishes one day before transfection. The lentiviral vector and the helper pHR8.9VPR and env plasmids pCMV-VSV-G or HIV LAI envelope (kindly donated by Dr. Una O'Doherty at University of Pennsylvania) were co-transfected in 293 T cells using calcium phosphate precipitation (Promega). Medium was replaced after 4 h and supernatants were harvested as described (Lee et al. (2005). Blood 106: 818-826; Agosto, et al. (2009). J Virol 83: 8153-8162). TZM-bl cells, resting/activated CD4 T cells, and CD8 depleted PBMC from healthy and HIV infected patients were transduced at a multiplicity of infection (MOI) of 5-50 as described earlier (Lee et al. (2005). Blood 106: 818-826). After transduction, the cells were washed twice with PBS and cultured in media for 48 h. Transduction efficiency was determined by examining for mCherry expression by flow cytometry.

Assay for HIV Replication in TZM-bl Reporter Cells

2 μg of shRNA expression vectors and 100 ng of HIV-1 NL4-3 plasmid (NIH AIDS Research and Reference Reagent Program) were co-transfected into 293 T cells using Lipofectamine 2000 reagent. The supernatants harvested two days after transfection was used for infecting equivalent number of TZM-bl cells in presence of 10 μg/ml DEAE-D. Tat-induced luciferase activities were determined in cell lysates 48 h post-infections using the Luciferase assay system (Promega) as previously described.

Assay for Toxicity of Micro-RNA Based shRNAs

To determine the toxicity of shRNA constructs, Jurkat cells were transfected with single, dual, and multiple shRNA constructs by Neon transfection system (Life Technology). Transfected cells were harvested after 48 h, stained with anti-Annexin V FITC antibody analyzed by flow cytometry. To determine vector cytotoxicity in CD4 T cells, mCherry expression was followed in transduced cells over time by flow cytometry. Lentivirally transduced CD8+depleted PBMCs were stimulated with PHA and cultured in presence of IL-2 and were monitored on day 0, 4, 7, and 12 for mCherry expression by flow cytometry. Lentivirus transduced cells harvested two and four days post-transduction were also subjected to MTS Assay (Promega) according to manufactures instructions.

HIV-1 Challenge Assays

Untransduced and lentiviral vector transduced TZM-bl cells were infected with R5-tropic BaL and X4-tropic NL4-3 strains of HIV-1 at an MOIs 0.01 for 4 hours at 37° C. $2\times10^5$ resting CD4 T cells and CD8 depleted PBMCs from normal and HIV seropositive donors were activated with PHA (2 μg/ml) after transduction with corresponding lentiviruses and cultured in the presence of IL2. Cells were infected 48 h post activation with HIV BaL and NL4-3, at MOIs of 0.01 and 0.001, respectively. Supernatants from TZM-bl cells and T cells/PBMCs were collected and analyzed for HIV replication by p24 ELISA assay (Perkin Elmer) as described previously.

Sequence Analysis of the Tat shRNA Target Region of HIV-1

Viral RNAs from four different HIV-seropositive donors were analyzed for shRNA-induced mutations in the Tat-shRNA target region on day 15 (mock) or 31(Tat/7shRNA) postinfection as previously described (Schopman et al. (2010). Retrovirology 7: 52; Sugiyama et al. (2011). Nucleic Acids Res 39: 589-598). Viral RNA was extracted using the QIAamp RNA Kit (Qiagen) and first strand cDNA was synthesized using Superscript III First Strand Synthesis System for RT-PCR (Invitrogen, USA) as per the manufacturer's instructions. DNA sequences were PCR amplified using Tat targeted primers sense 5'-TGT TGC TTT CAT TGC CAA GT-3' and antisense primer 5'-TGA TGA GTC TGA CTG CCT TGA-3'. PCR was performed using the following thermal program: 95° C. for 2 min and then 35 cycles at 95° C. for 30 s. 57.8° C. for 30 s, and 72° C. for 30 s, followed by 72° C. for 5 min. The PCR products were gel purified and cloned into the pCR2.1 TOPO vector and subsequently sequenced with the M13R primers.

NOD/SCID-Hu PBL Mouse Model

NOD/SCID IL2rγcnull mice were purchased from Jackson Laboratory (Bar Harbor, Me.) and maintained in specific pathogen free conditions at the Paul L. Foster School of Medicine, TTUHSC animal facility. Hu-PBL mice were generated as described (Kumar et al. (2008). Cell 134: 577-586). In brief, mice were conditioned with sublethal (2 Gy) whole-body irradiation. Lentivirus transduced HIV-seropositive donor PBMCs ($2\times10^6$) were intravenously injected via the tail vein (in 0.2 ml PBS) into 6 to 7 week-old mice. Cell engraftment was tested 7, 28, and 42 days after transplantation by staining mouse PBMCs with human CD45, CD3, CD4, and CD8 antibodies. All mouse experiments had been approved by the TTUHSC IACUC and animal infection experiments were performed in bio-safety level 2 animal facility at TTUHSC.

Flow Cytometry

Flow cytometry was performed to determine cell surface antigen expression by 30-min incubation on ice with pertinent antibodies. The following monoclonal antibodies were used: human-specific monoclonal antibodies used were anti-CCR5 conjugated with FITC or APC (2D7/CCR5; BD Pharmingen), anti-human CD45 (PE), CD3 (FITC). CD4 (PB), CD8 (APC), and corresponding isotype control mAbs (BD Pharmingen). Data were acquired by BD FACS Canto II and analyzed on BD FACS Diva software v3.0. Overlays were made using FlowJo software v3.0 where ever applicable.

Small RNA Deep Sequencing

Small RNA libraries were constructed and sequenced in a similar manner as described previously (Ma et al. (2013). Proc Natl Acad Sci USA 110: 20687-20692; Ma et al. (2014). Mol Ther Nucleic Acids 3: e161). Briefly, 48 hours after the constructs were transfected into 293FT cells, the small RNAs were purified with the miRNeasy kit (Qiagen, Valencia, Calif.) as per the manufacturer's instructions. Small RNA (50 ng) was ligated with 3' and 5' linkers (with barcode) using an improved ligation method that was optimized comprehensively to minimize the ligation bias between different small RNAs. The ligated small RNAs were reverse transcribed and amplified with the KAPA library amplification kit (KAPA Biosystems, Woburn, Mass.) for 10 cycles, and the library sequenced using the Illumina MiSeq, Salt Lake City, Utah. All reads that were sequenced only once were discarded to lower the noise level.

This example is also illustrated in Choi et al. Mol Ther. 2015; 23(2):310-320, titled "Multiplexing seven miRNA-Based shRNAs to suppress HIV replication," which is incorporated by reference in its entirety.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

All publications, patents, and accession numbers mentioned herein are hereby incorporated by reference in their entirety as if each individual publication or patent was specifically and individually indicated to be incorporated by reference.

EQUIVALENTS

While specific embodiments of the compositions and methods herein have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. An artificial miRNA cluster encoding seven modified pri-miRNA-like molecules, the artificial miRNA cluster comprising:

a first nucleotide sequence encoding a first modified pri-miRNA-like molecule derived from a naturally-occurring pri-miRNA that gives rise to miR-30a, a second nucleotide sequence encoding a second modified pri-miRNA-like molecule derived from a naturally occurring pri-miRNA that gives rise to miR-21, a third nucleotide sequence encoding a third modified pri-miRNA-like molecule derived from a naturally-occurring pri-miRNA that gives rise to miR-20a, a fourth nucleotide sequence encoding a fourth modified pri-miRNA-like molecule derived from a naturally occurring pri-miRNA that gives rise to miR-16-1, a fifth nucleotide sequence encoding a fifth modified pri-miRNA-like molecule derived from a naturally occurring pri-miRNA that gives rise to miR-122, a sixth nucleotide sequence encoding a sixth modified pri-miRNA-like molecule derived from a naturally-occurring pri-miRNA that gives rise to miR-185, a seventh nucleotide sequence encoding a seventh modified pri-miRNA-like molecule derived from a naturally occurring pri-miRNA that gives rise to miR-150, and wherein each of the seven modified pri-miRNA-like molecules comprises: a stem region comprising an artificial RNA molecule comprising a guide strand and a passenger strand, wherein the guide strand is substantially complementary to a target mRNA encoded by a gene chosen from human CCR5, HIV-1 Gag, HIV-1 Env, HIV-1 Tat, HIV-1 Pol, or HIV-1 Vif; a terminal loop region; a 5' flanking region; and a 3' flanking region, wherein each 5' flanking region and each 3' flanking region is the respective flanking sequence that is removed from each respective naturally occurring pri-miRNA by Drosha cleavage of that naturally occurring pri-miRNA.

2. The artificial miRNA cluster of claim 1, wherein the first modified pri-miRNA-like molecule comprises a guide strand that is substantially complementary to a target mRNA encoded by the human CCR5 gene.

3. The artificial miRNA cluster of claim 1, wherein the second modified pri-miRNA-like molecule comprises a guide strand that is substantially complementary to a target mRNA encoded by the HIV-1 Gag gene.

4. The artificial miRNA cluster of claim 1, wherein the third modified pri-miRNA-like molecule comprises a guide strand that is substantially complementary to a target mRNA encoded by the HIV-1 Env gene.

5. The artificial miRNA cluster of claim 1, wherein the fourth modified pri-miRNA-like molecule comprises a guide strand that is substantially complementary to a target mRNA encoded by the HIV-1 Tat gene.

6. The artificial miRNA cluster of claim 1, wherein the fifth modified pri-miRNA-like molecule comprises a guide strand that is substantially complementary to a target mRNA encoded by the HIV-1 Pol gene.

7. The artificial miRNA cluster of claim 1, wherein the sixth modified pri-miRNA-like molecule comprises a guide strand that is substantially complementary to a target mRNA encoded by the HIV-1 Pol gene.

8. The artificial miRNA cluster of claim 1, wherein the sixth modified pri-miRNA-like molecule comprises a guide strand that is substantially complementary to a target mRNA encoded by the HIV-1 Vif gene.

9. A viral vector comprising the artificial miRNA cluster of claim 1.

10. The viral vector of claim 9, which is a lentiviral vector.

11. A viral particle produced by the viral vector of claim 9.

12. A cell transduced by the viral particle of claim 11.

* * * * *